US006413776B1

(12) United States Patent
Vogels et al.

(10) Patent No.: US 6,413,776 B1
(45) Date of Patent: Jul. 2, 2002

(54) HIGH THROUGHPUT SCREENING OF GENE FUNCTION USING ADENOVIRAL LIBRARIES FOR FUNCTIONAL GENOMICS APPLICATIONS

(75) Inventors: Ronald Vogels, Linschoten; Abraham Bout, Moerkapelle; Helmuth H. G. van Es, Hoofddorp; Govert Shouten, Leiden, all of (NL)

(73) Assignee: Galapagos Geonomics N.V., Mechelen (BE)

( * ) Notice: Subject to any disclaimer, the term of this patent is extended or adjusted under 35 U.S.C. 154(b) by 0 days.

(21) Appl. No.: 09/097,239

(22) Filed: Jun. 12, 1998

(51) Int. Cl.$^7$ .............................. C12N 5/10; C12N 15/66

(52) U.S. Cl. ................... 435/462; 435/463; 435/235.1; 435/325

(58) Field of Search ................................ 435/462, 463, 435/235.1, 325

(56) References Cited

U.S. PATENT DOCUMENTS

| | | | |
|---|---|---|---|
| 4,405,712 A | 9/1983 | Vande Woude et al. | |
| 4,497,796 A | 2/1985 | Salser et al. | |
| 4,727,028 A | 2/1988 | Santerre et al. | |
| 4,740,463 A | 4/1988 | Weinberg et al. | |
| 5,190,931 A | 3/1993 | Inouye | |
| 5,208,149 A | 5/1993 | Inouye | |
| 5,518,913 A | 5/1996 | Massie et al. | |
| 5,837,511 A | 11/1998 | Falck-Pedersen et al. | |
| 5,871,982 A | * 2/1999 | Wilson et al. | ........... 435/172.3 |
| 5,994,106 A | 11/1999 | Kovesdi et al. | |
| 5,994,128 A | 11/1999 | Fallaux et al. | |
| 6,033,908 A | * 3/2000 | Bout et al. | ................... 435/325 |
| 6,040,174 A | 3/2000 | Imler et al. | |
| 6,057,427 A | 5/2000 | Smith et al. | ........... 530/388.23 |
| 6,110,735 A | 8/2000 | Chartier et al. | .......... 435/320.1 |
| 6,197,502 B1 | 3/2001 | Renner et al. | ................. 435/6 |

FOREIGN PATENT DOCUMENTS

| | | |
|---|---|---|
| AU | 28533/95 | 3/1996 |
| CA | 2053187 | 4/1993 |
| CA | 2117668 | 9/1995 |
| EP | 0 707 071 A1 | 4/1996 |
| EP | 0 955 373 A2 A3 | 11/1999 |
| FR | 2 707 664 | 1/1995 |
| WO | WO 94/12649 | 6/1994 |
| WO | WO 94/28152 | 12/1994 |
| WO | WO 95/02697 | 1/1995 |
| WO | WO 95/34671 | 12/1995 |
| WO | WO 96/17070 | 6/1996 |
| WO | WO 97/00326 | 1/1997 |
| WO | WO-97/25446 | * 7/1997 |
| WO | WO 97/27212 | 7/1997 |
| WO | WO 97/27213 | 7/1997 |
| WO | WO99/32618 | 7/1999 |

OTHER PUBLICATIONS

Shepherd et al., "Preparation and screening of an arrayed human genomic library generated with the P1 cloning system," *Proc. Natl. Acad. Sci. USA*, vol. 91, pp. 2629–2633 (Mar. 1994)+.
Woon et al., "Construction and characterization of a 10–fold genome equivalent Rat P1–derived artificial chromosome library," *Genomics*, vol. 50, pp. 306–316 (1998)+.
Crouzet et al., *Proc. Natl. Acad. Sci. USA*, vol. 94, pp. 1414–1419 (1997).
Vogelstein et al., *Proc. Natl. Acad. Sci. USA*, vol. 95, pp. 2509–2514 (1998).
Davis et al., *Gene Therapy*, vol. 5, pp. 1148–1152 (1998).
Ketner et al., *Proc. Natl. Acad. Sci. USA*, vol. 91, pp. 6186–6190 (1994).
Okada et al., *Nucleic Acids Research*, vol. 26, No. 8, pp. 1947–1950 (1998).
Chartier et al., *J. Virology*, vol. 70, pp. 4805–4810 (1996).
Fu et al., *Human Gene Therapy*, vol. 8, pp. 1321–1330 (1997).
Tashiro et al.,*Human Gene Therapy*, vol. 10, pp. 1845–1852 (1999).
Bett et al., *Proc. Natl. Acad. Sci. USA*, vol. 91, pp. 8802–8806 (1994).
He et al.,*Proc. Natl. Acad. Sci. USA*, vol. 95, pp. 2509–2514 (1998).
Vollmer et al., "Efficient cloning of genes of Neurospora crassa," *Proc. Natl. Acad. Sci. USA*, vol. 83, pp. 4869–4873 (Jul. 1986).
Hall et al., *Genome Research*, (1996) 6: 781–790.
Jayawickreme and Kost, *Current Opinion in Biotechnology* (1997) 8: 629–634.
Stein et al., *Nucleic Acids Research* (1997) 25: 2598–2602.
Paper entitled "Restricted Changes in the Adenovirus DNA–Binding Protein That Lead to Extended Host Range or Temperature–Sensitive Phenotypes" by D.E. Brough, S.A. Rice, S. Sell and D.F. Kelessig—Journal of Virology, Jul. 1985, pp. 206–212.
Paper entitled "Multiplication of Viruses—An Overview" by B. Roizman—Virology, Second Edition 1990 —pp. 28, 29, 87 & 88.
Paper entitled "Ablation of E2A in Recombinant Adenoviruses Improves Transgene Persistence and Decreases Inflammatory Response in Mouse Liver" by J.F. Engelhard, X. Ye, B. Doranz and J.M. Wilson—Proc. Nat. Acad. Sci. USA vol. 91, pp. 6196–6200.

* cited by examiner

*Primary Examiner*—James Ketter
(74) *Attorney, Agent, or Firm*—Synnestvedt & Lechner LLP

(57) ABSTRACT

Novel adenovirus vectors and methods for their use are provided to determine the function of the product(s) of one or more sample nucleic acids. The sample nucleic acids are synthetic oligonucleotides, DNA, or cDNA and encode polypeptides, antisense nucleic acids or GSEs. The sample nucleic acids are expressed in a host by recombinant adenovirus vectors to alter at least one phenotype of the host. The altered phenotype(s) is identified as a means to assign a biological function to the product(s) encoded by the sample nucleic acid(s).

36 Claims, 29 Drawing Sheets

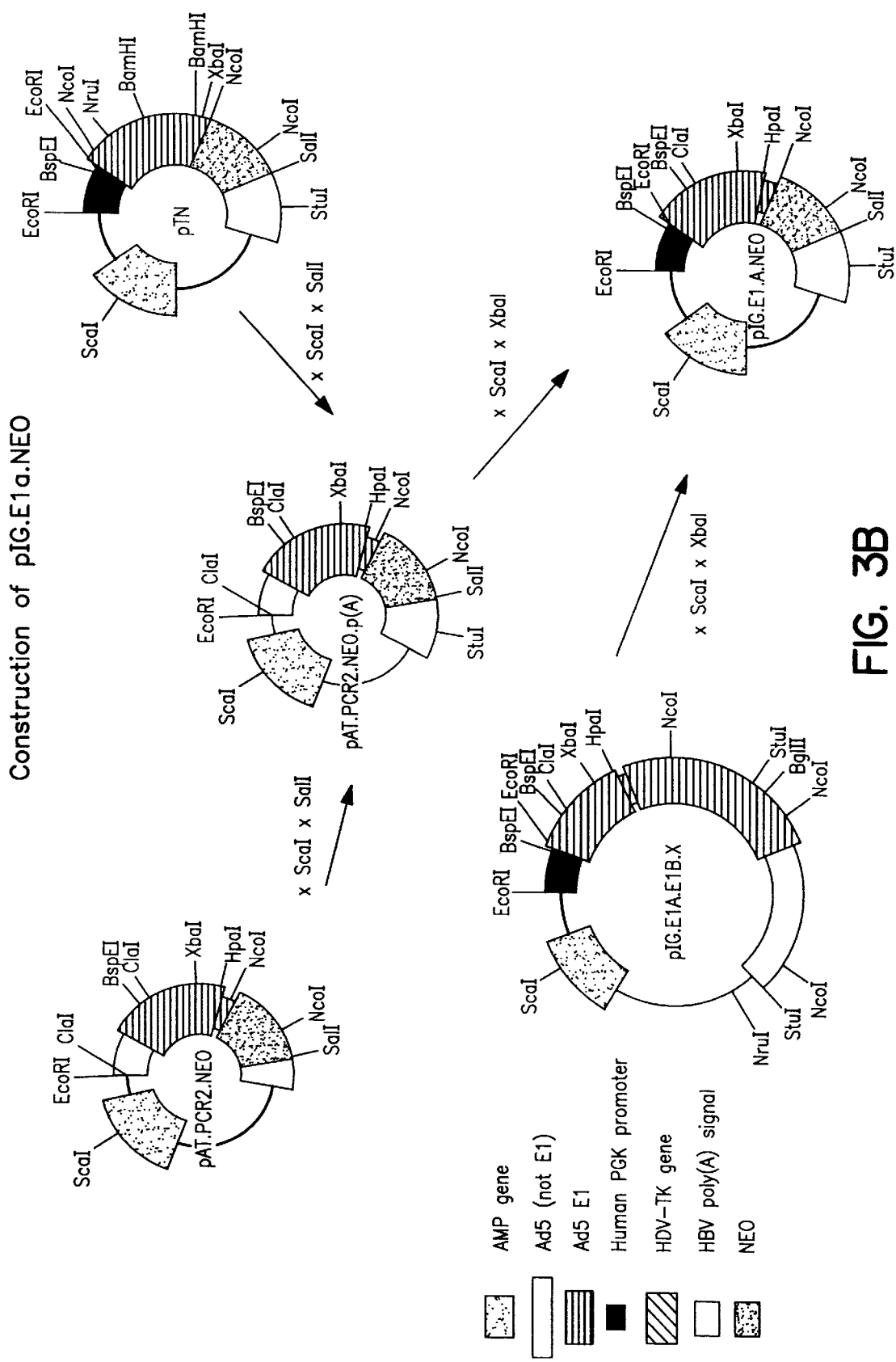

Transfection efficiency of PER.C3, PER.C5, PER.C6 and 911 cells. Cells were cultured in 6-well plates and transfected (n=2) with 5 μg pRSV.lasZ by calcium-phosphate co-precipitation. Forty-eight hours later the cells were stained with X-GAL. The mean percentage of blue cells is shown.

Packaging system based on primary cells

Packaging system based on established cell lines: transfection with E1a and selection with G418

The potential hairpin conformation of a single-stranded
DNA molecule that contains the HP/asp sequences used in these
studies. Restriction with the restriction endonucleases *Asp718I*
of plasid pICLHa, containing the annealed oligonucleotide pair
HP/asp1 en HP/asp2 will yield a linear double-stranded DNA
fragment. In cells in which the required adenovirus genes are
present, replication can initiate at the terminus that contains
the ITR sequence. During the chain elongation, the one of the
strands will be displaced. The terminus of the single-stranded
displaced-strand molecule can adopt the conformation depicted
above. In this conformation the free 3'-terminus can serve as a
primer for the cellular and/or adenovirus DNA polymerase,
resulting in conversion of the displaced strand in a double-
stranded form.

```
5'-GTACACTGACCTAGTGCCGCCCGGGCA
          ||||||||||||||||| A
   3'-GATCACGGCGGGCCCGA
```

FIG. 15

HIGH THROUGHPUT SCREENING OF GENE FUNCTION USING ADENOVIRAL LIBRARIES FOR FUNCTIONAL GENOMICS APPLICATIONS

FIELD OF THE INVENTION

The invention is related to high-throughput methods for identifying the function of sample nucleic acids and their products. The invention is exemplified by the use of the E1-complementing adenoviral packaging cell line PER.C6 in combination with an E1-deleted plasmid-based generation system to produce recombinant adenovirus vectors in a high throughput setting to functionate the product of a sample nucleic acid.

BACKGROUND

The ultimate goal of the Human Genome Project is to sequence the entire human genome. The expected outcome of this effort is a precise map of the 70,000–100,000 genes that are expressed in man. However, a fairly complete inventory of human coding sequences will most likely be publicly available sooner. Since the early 1980s, a large number of Expressed Sequence Tags (ESTs; partial DNA sequences read from the ends of cDNA molecules) have been obtained by both government and private research organizations. A hallmark of these endeavors, carried out by a collaboration between Washington University Genome Sequencing Center and members of the IMAGE (Integrated Molecular Analysis of Gene Expression) consortium (http://www-bio.llnl.gov/bbrp/image/image.html), has been the rapid deposition of the sequences into the public domain and the concomitant availability of the sequence-tagged cDNA clones from several distributors (Marra, et al. (1998) *Trends Genet*. 14 (1):4–7). At present, the collection of cDNAs is believed to represent approximately 50,000 different human genes expressed in a variety of tissues including liver, brain, spleen, B-cells, kidney, muscle, heart, alimentary tract, retina, hypothalamus, and the number is growing daily.

Recent initiatives like that of the Cancer Genome Anatomy project support an effort to obtain full-length sequences of clones in the Unigene set (a set of cDNA clones that is publicly available) by the year 1999. At the same time, commercial entities propose to validate (re-sequence) 40,000 full-length cDNA clones by 1999 and the individual clones will be available to any interested party. The speed by which the coding sequences of novel genes are identified is in sharp contrast to the rate by which the function of these genes is elucidated. Assigning functions to the cDNAs in the databases, or "functional genomics", is a major challenge in biotechnology today.

For decades, novel genes were identified as a result of research designed to explain a biological process or hereditary disease and the function of the gene preceded its identification. In functional genomics, coding sequences of genes are first cloned and sequenced and the sequences are then used to find functions. Although other organisms such as Drosophila, *C. elegans*, and Zebrafish are highly useful for the analysis of fundamental genes, for complex mammalian physiological traits (blood glucose, cardiovascular disease, inflammation) animal model systems are inevitable. However, the slow rate of reproduction and the high housing costs of the animal models are a major limitation to high-throughput functional analysis of genes. Although labor-intensive efforts are made to establish "libraries" of mouse strains with chemically or genetically mutated (tagged) genes in a search for phenotypes that allow the elucidation of gene function or that are related to human diseases, a systematic analysis of the complete spectrum of mammalian genes, be it human or animal, is a significant task.

In order to keep pace with the volume of sequence data, the field of functional genomics needs the ability to perform high-throughput analysis of true gene function. Recently, a number of techniques have been developed that are designed to link tissue and cell specific gene expression to gene function. These include cDNA microarraying and gene chip technology and differential display mRNA. Serial Analysis of Gene Expression (SAGE) or differential display of messenger RNA can identify genes that are expressed in tumor tissue but are absent in the respective normal or healthy tissue. In this way, potential genes with regulatory functions can be selected from the excess of ubiquitously expressed genes that have a less-likely chance to be useful for small drug screening or gene therapy projects. Gene chip technology has the potential to allow the monitoring of gene expression through the measurement of mRNA expression levels in cells of a large number of genes in only a few hours. Cells cultured under a variety of conditions can be analyzed for their mRNA expression patterns and compared. Currently, DNA microarray chips with 40,000 non-redundant human genes are produced and are planned to be on the market in 1999 (Editorial (1998) *Nat. Genet*. 18 (3):195–7.). However, these techniques are primarily designed for screening cancer cells and not for screening for specific gene functions.

Double or triple hybrid systems also are used to add functional data to the genomic databases. These techniques assay for protein-protein, protein-RNA, or protein-DNA interactions in yeast or mammalian cells (Brent and Finley (1997) *Annu. Rev. Genet*. 31:663–704). However, this technology does not provide a means to assay for a large number of other gene functions such as differentiation, motility, signal transduction, enzyme and transport activity. Yeast expression systems have been developed which are used to screen for naturally secreted and membrane proteins of mammalian origin (Klein, et al. (1996) *Proc. Natl. Acad. Sci. USA* 93 (14):7108–13). This system also allows for collapsing of large libraries into libraries with certain characteristics which aid in the identification of specific genes and gene products. A disadvantages of this system is that genes encoding secreted proteins primarily are selected. Secondly, this technology is based on yeast as a heterologous expression system and therefore there will be gene products that are not appropriately folded resulting in a biased library.

Other current strategies include the creation of transgenic mice or knockout mice. A successful example of gene discovery by such an approach is the identification of the osteoprotegerin gene. DNA databases were screened to select ESTs with features suggesting the cognate genes encoded secreted proteins. The biological functions of the genes were assessed by placing the corresponding full-length cDNAs under the control of a liver-specific promoter. Transgenic mice created with each of these constructs consequently have high plasma levels of the relevant protein. Subsequently, the transgenic animals were subjected to a battery of qualitative and quantitative phenotypic investigations. One of the genes that was transfected into mice produced mice with an increased bone density, which led subsequently to the discovery of a potent anti-osteoporosis factor (Simonet, et al. (1997) *Cell*. 89 (2):309–19). Such a method has the disadvantages that it is costly and highly time consuming.

The challenge in functional genomics is to develop and refine all the above-described techniques and integrate their results with existing data in a well-developed database that provides for the development of a picture of how gene function constitutes cellular metabolism and a means for this knowledge to be put to use in the development of novel medicinal products. The current technologies have limitations and do not necessarily result in true functional data. Therefore, there is a need for a method that allows for direct measurement of function of a single gene from a collection of genes (gene pools or individual clones) in a high-throughput setting in appropriate in vitro assay systems and animal models.

RELEVANT LITERATURE

The development of high throughput screens is discussed in Jayawickreme and Kost, (1997) *Curr. Opin. Biotechnol.* 8:629–634. A high throughput screen for rarely transcribed differentially expressed genes is described in von Stein et al., (1997) *Nucleic Acids Res.* 35: 2598–2602. High throughput genotyping is disclosed in Hall et al., (1996) *Genome Res.* 6:781–790. Methods for screening transdominant intracellular effector peptides and RNA molecules are disclosed in Nolan, WO97/27212 and WO/9727213.

SUMMARY OF THE INVENTION

Methods, and compositions for use therein, are provided for directly, rapidly and unambiguously measuring in a high throughput setting the function of sample nucleic acids of unknown function, using a plasmid-based E1-deleted adenoviral vector system and an E1-complementing host cell. The method includes the steps of constructing a set of adapter plasmids by inserting a set of cDNAs, DNAs, ESTs, genes, synthetic oligonucleotides or a library of nucleic acids into E1-deleted adapter plasmids, cotransfecting an E1-complementing cell line with the set or library of adapter plasmids and a plasmid(s) having sequences homologous to sequences in the set of adapter plasmids and which also includes all adenoviral genes not provided by the complementing cell line or adapter plasmids necessary for replication and packaging to produce a set or library of recombinant adenoviral vectors preferably in a miniaturized, high throughput setting. To identify and assign function to product(s) encoded by the sample nucleic acids, a host is transduced in a high throughput setting with the recombinant adenoviral vectors which express the product(s) of the sample nucleic acids and thereby alter a phenotype of a host. The altered phenotype is identified and used as the basis to assign a function to the product(s) encoded by the sample nucleic acids. The plasmid-based system is used to rapidly produce adenovirus vector libraries that are preferably RCA-free for high throughput screening. Each step of the method can be performed in a multiwell format and automated to further increase the capacity of the system. This high throughput system facilitates expression analysis of a large number of sample nucleic acids from human and other organisms both in vitro and in vivo and is a significant improvement over other available techniques in the field.

BRIEF DESCRIPTION OF THE DRAWINGS

FIG. 3B: Construction of pIG.E1A.NEO. pIG.E1A.NEO encodes Ad5 nucleotides 459–1713 operatively linked to the human PGK promoter. Also encoded is the E1B promoter functionally linked to the neomycin resistance gene (Neo$^R$) and the hepatitis B virus (HBV) poly(A) signal. In this construct, the AUG codon of the E1B 21 kDa protein functions as the initiation codon of Neo$^R$. The HBV poly(A) signal of pAT-PCR2-NEO (see FIG. 3A) was completed by replacing the Sca I-Sal I fragment of pAT-PCR2-NEO with the corresponding fragment of pTN, producing pAT.PCR2.NEO.p(A), and replacing the Sca I-Xba I fragment of pAT.PCR2.NEO.p(A) with the corresponding fragment of pIG.E1A.E1B.X, producing pIG.E1A.NEO.

Cells were cultured in 6-well plates and transfected in duplicate with 5 μg pRSV.lacZ by calcium-phosphate co-precipitation. Forty-eight hours post-transfection, cells were stained with X-Gal and blue cells were counted. Results shown are the mean percentage of blue cells per well.

Figure 10:
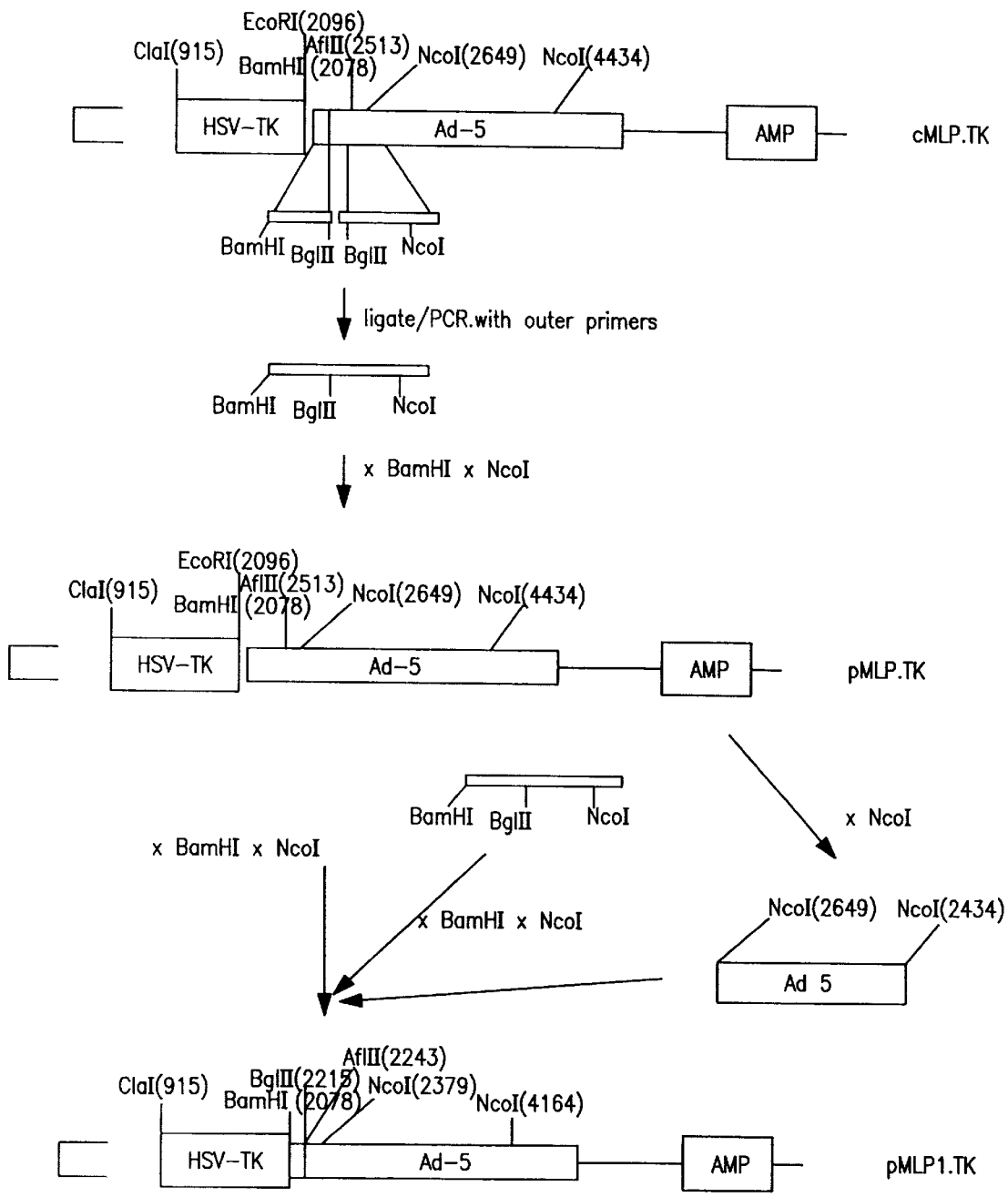

FIG. 10: Construction of adenovirus vector, pMLPI.TK. pMLPI.TK was designed to have no sequence overlap with the packaging construct pIG.E1A.E1B. pMLPI.TK was derived from pMLP.TK by deletion of the region of sequence overlap with pIG.E1A.E1B and deletion of non-coding sequences derived from lacZ. SV40 poly(A) sequences of pMLP.TK were PCR amplified with primers SV40-1 (SEQ ID NO:33), which introduces a BamH I site and SV40-2 (SEQ ID NO:34), which introduces a Bgl II site. pMLP.TK Ad5 sequences 2496 to 2779 were PCR amplified with primers Ad5-1 (SEQ ID NO:35), which introduces a Bgl II site and Ad5-2 (SEQ ID NO:36). Both PCR products were Bgl II digested, ligated, and PCR amplified with primers SV40-1 and Ad5-2. This third PCR product was BamH I and Afl III digested and ligated into the corresponding sites of pMLP.TK, producing pMLPI.TK.

Figure 11A:
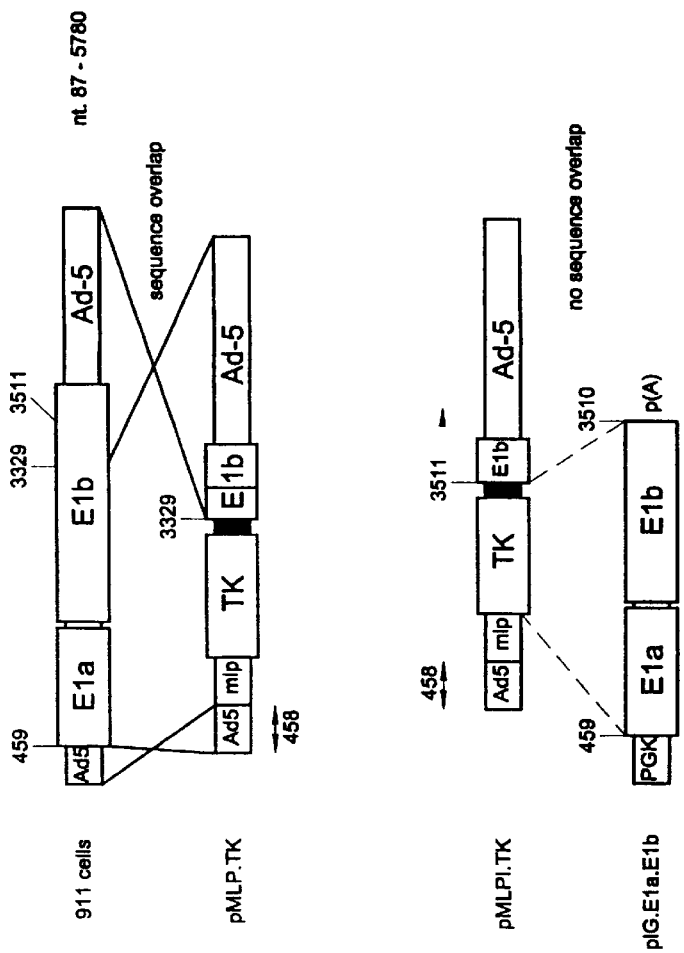
Figure 1B:
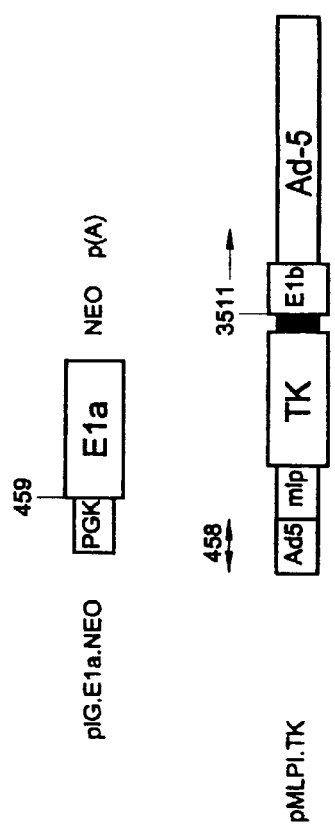

FIG. 11A: New adenovirus packaging construct, pIG.E1A.E1B, does not have sequence overlap with new adenovirus vector, pMLPI.TK. Regions of sequence overlap between the packaging construct, pAd5XhoIC expressed in 911 cells and adenovirus vector, pMLP.TK, that can result in homologous recombination and the formation of replication competent adenovirus are shown. In contrast, there are no regions of sequence overlap between the new packaging construct, pIG.E1A.E1B, expressed in PER.C6 cells, and the new adenovirus vector, pMLPI.TK.

FIG. 11B: New adenovirus packaging construct, pIG.E1A.NEO, does not have sequence overlap with new adenovirus vector, pMLPI.TK. There are no region of sequence overlap between the new packaging construct, pIG.E1A.NEO and the new adenovirus vector, pMLPI.TK, that can result in homologous recombination and the formation of replication competent adenovirus.

Figure 12:
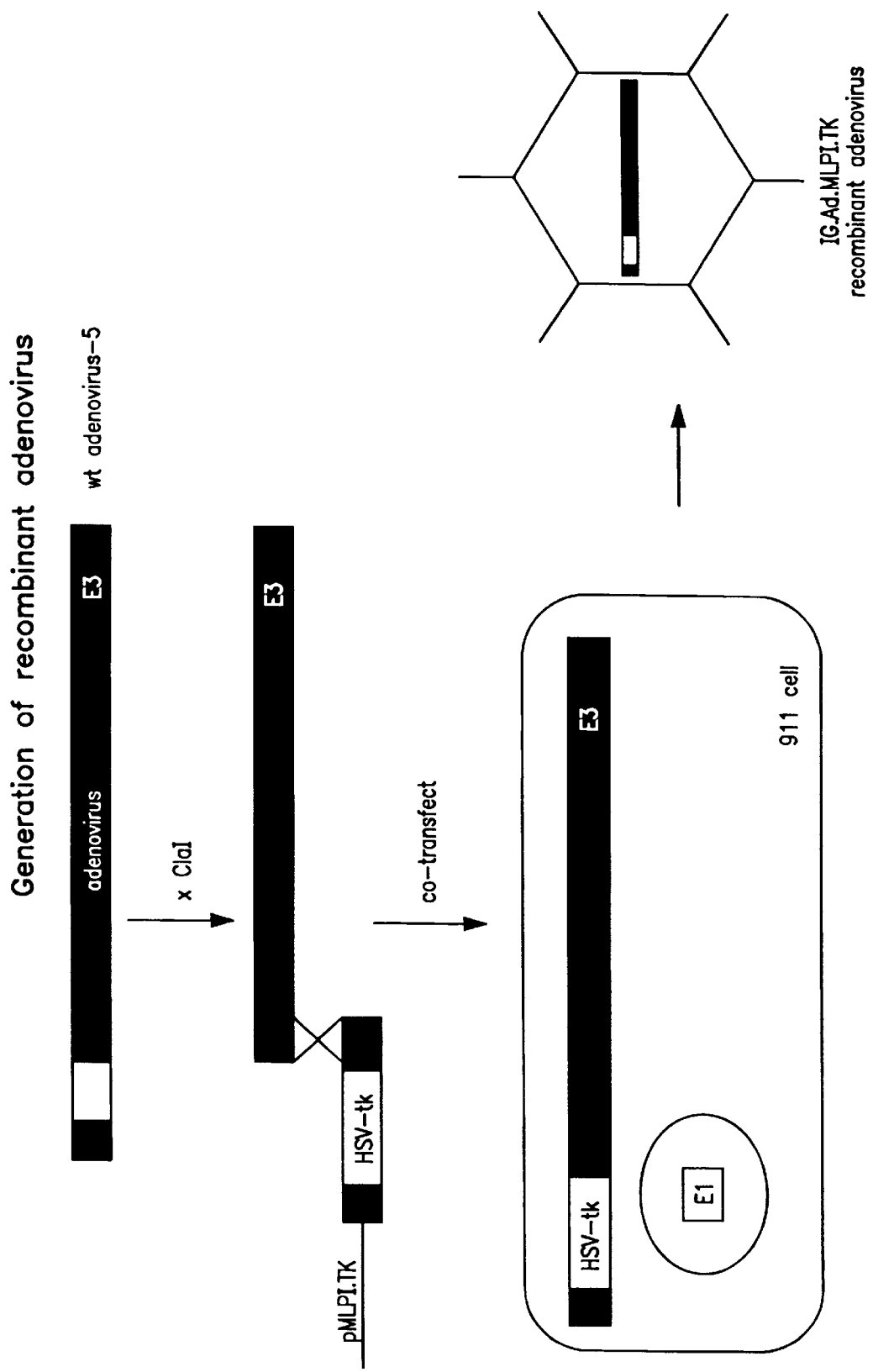

FIG. 12: Generation of recombinant adenovirus, IG.Ad.MLPI.TK. Recombinant adenovirus, IG.Ad.MLPI.TK, was generated by co-transfection of 293 cells, with Sal I linearized pMLPI.TK and the right arm of Cla I digested, wild-type Ad5 DNA. Homologous recombination between linearized pMLPI.TK and wild-type Ad5 DNA produces IG.Ad.MLPI.TK DNA, which contains an E1 deletion of nucleotides 459–3510. 293 cells transcomplement the deleted Ad5 genome, thereby, permitting replication of the IG.Ad.MLPI.TK DNA and its packaging into virus particles.

Figure 13:
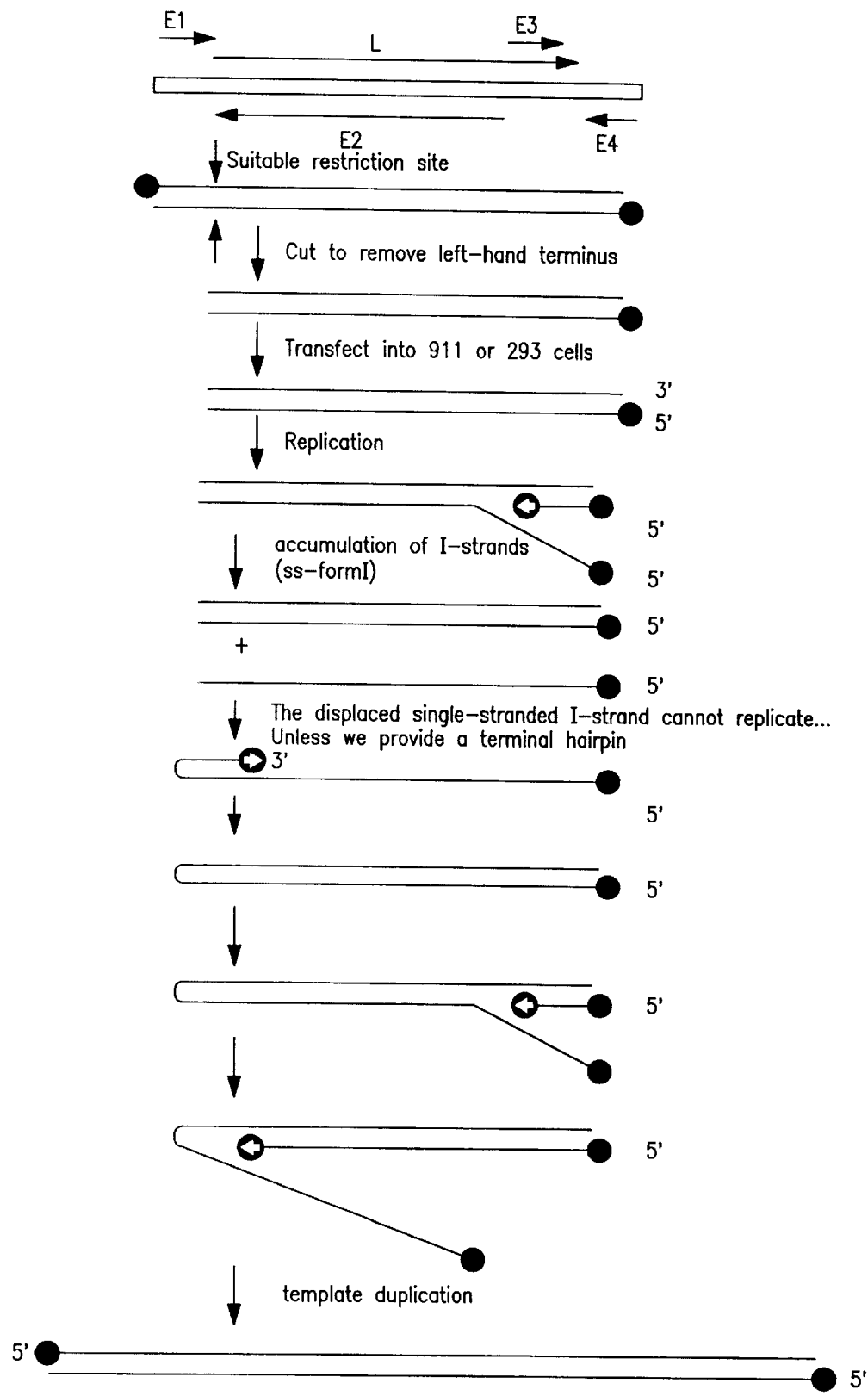

FIG. 13: Rationale for the design of adenovirus-derived recombinant DNA molecules that duplicate and replicate in cells expressing adenovirus replication proteins. A diagram of the adenovirus double-stranded DNA genome indicating the approximate locations of E1, E2, E3, E4, and L regions is shown. The terminal polypeptide (TP) attached to the 5'-termini is indicated by closed circles. The right arm of the adenovirus genome can be purified by removal of the left arm by restriction enzyme digestion. Following transfection of the right arm into 293 or 911 cells, adenoviral DNA polymerase (white arrow) encoded on the right arm, will produce only single-stranded forms. Neither the double-stranded or single-stranded DNA can replicate because they lack an ITR at one termini. Providing the single-stranded DNA with a sequence that can form a hairpin structure at the 3'-terminus that can serve as a substrate for DNA polymerase will extend the hairpin structure along the entire length of the molecule. This molecule can also serve as a substrate for a DNA polymerase but the product is a duplicated molecule with ITRs at both termini that can replicate in the presence of adenoviral proteins.

Figure 14:
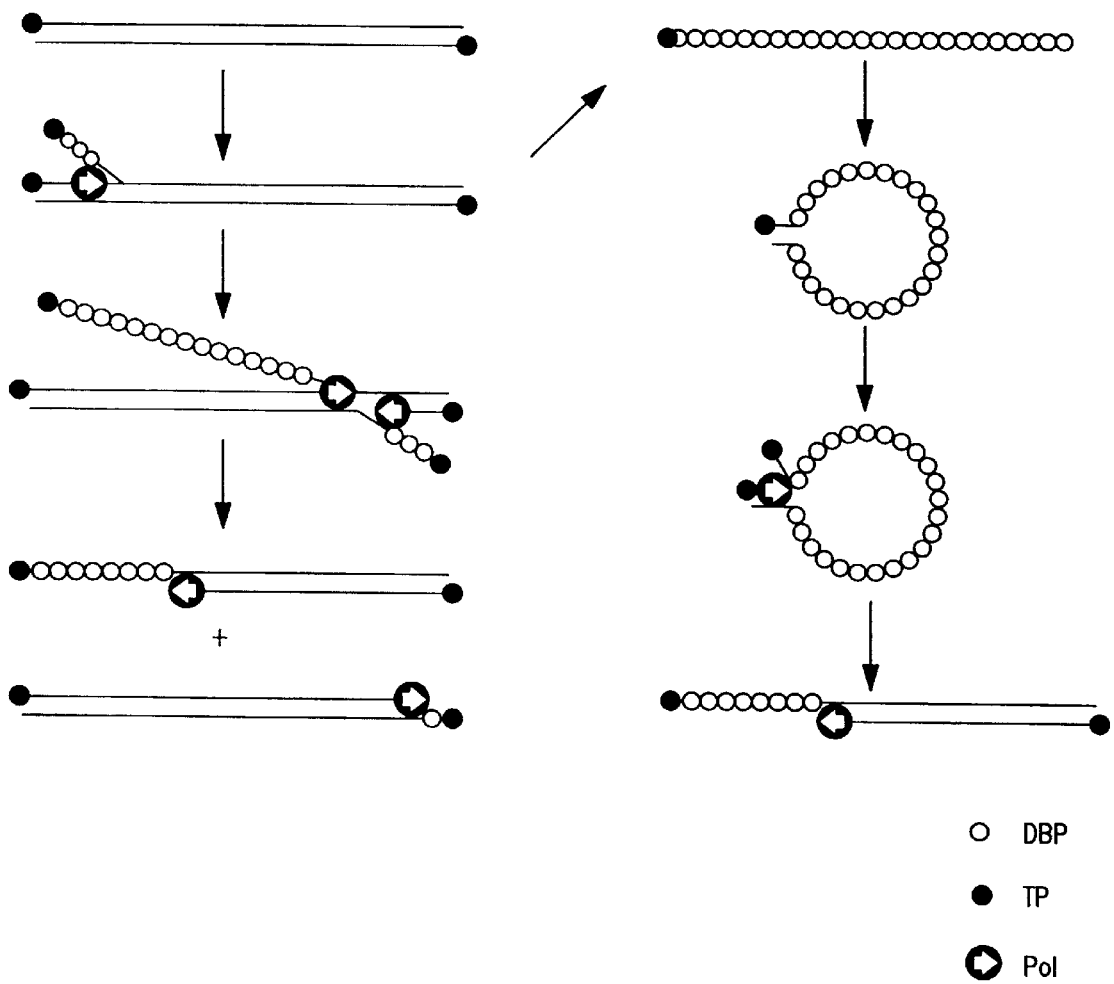

FIG. 14: Adenovirus genome replication. The adenovirus genome is shown in the top left. The origins or replication are located within the left and right ITRs at the genome ends. DNA replication occurs in two stages. Replication proceeds from one ITR generating a daughter duplex and a displaced parental single-strand which is coated with adenovirus DNA binding protein (DBP, open circles) and can form a pan-handle structure by annealing of the ITR sequences at both termini. The panhandle is a substrate for DNA polymerase (Pol: white arrows) to produce double-stranded genomic DNA. Alternatively, replication proceeds from both ITRs, generating two daughter molecules, thereby, obviating the requirement for a panhandle structure.

FIG. 15: Potential hairpin conformation of a single-stranded DNA molecule that contains the HP/asp sequence (SEQ ID NO:47). Asp718 I digestion of pICLha, containing the cloned oligonucleotides, HP/asp1 and HP/asp2 yields a linear double-stranded DNA with an Ad5 ITR at one terminus and the HP/asp sequence at the other terminus. In cells, expressing the adenovirus E2 region, a single-stranded DNA is produced with an Ad5 ITR at the 5'-terminus and the hairpin conformation at the 3'-terminus. Once formed, the hairpin can serve as a primer for cellular and/or adenovirus DNA polymerase to convert the single stranded DNA to double stranded DNA.

Figure 16:
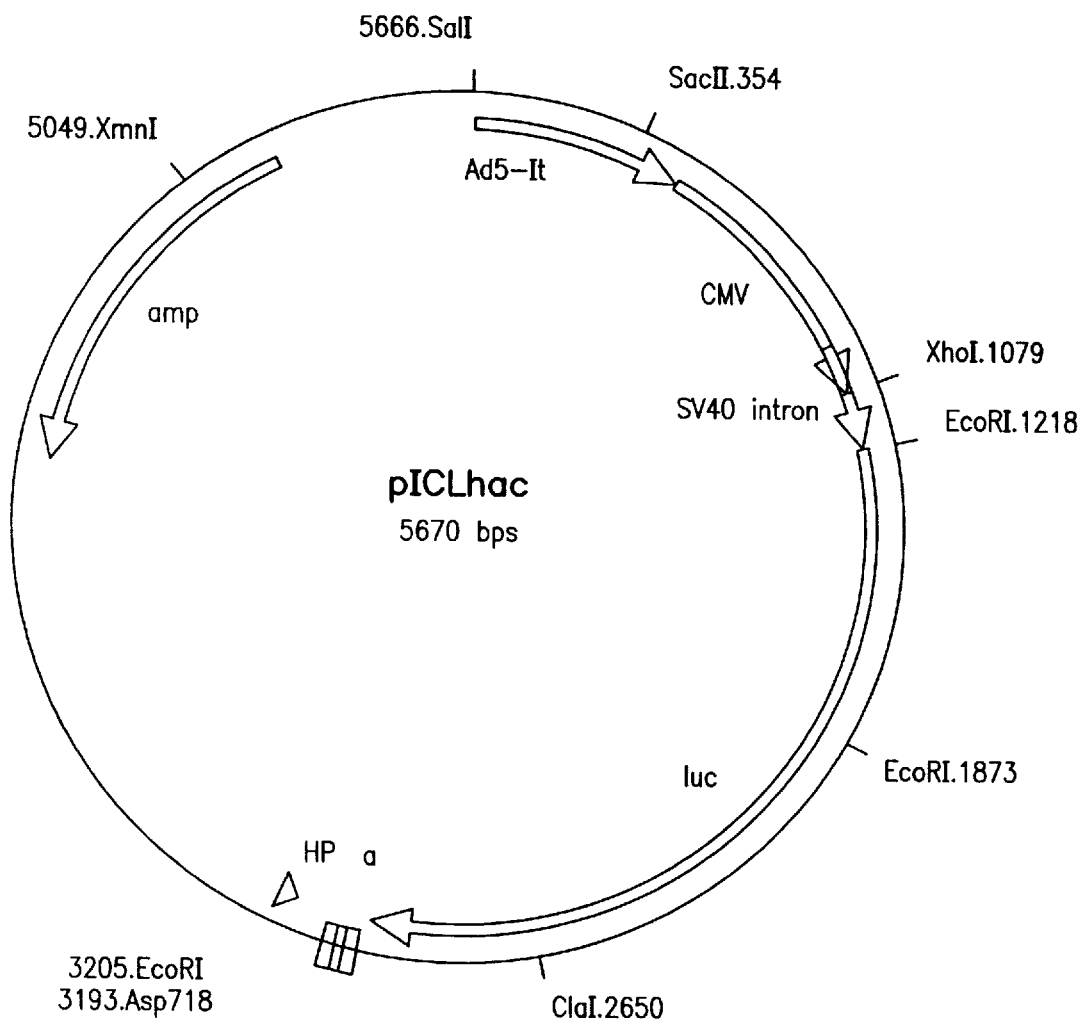

FIG. 16: Diagram of pICLhac. pICLhac contains all the elements of pICL (FIG. 19) but also contains in the Asp718 site, the HP/asp sequence in an orientation that will produce the hairpin structure shown in FIG. 15, following linearization by Asp718 digestion and transfection into cells expressing adenovirus E2 proteins.

Figure 17:
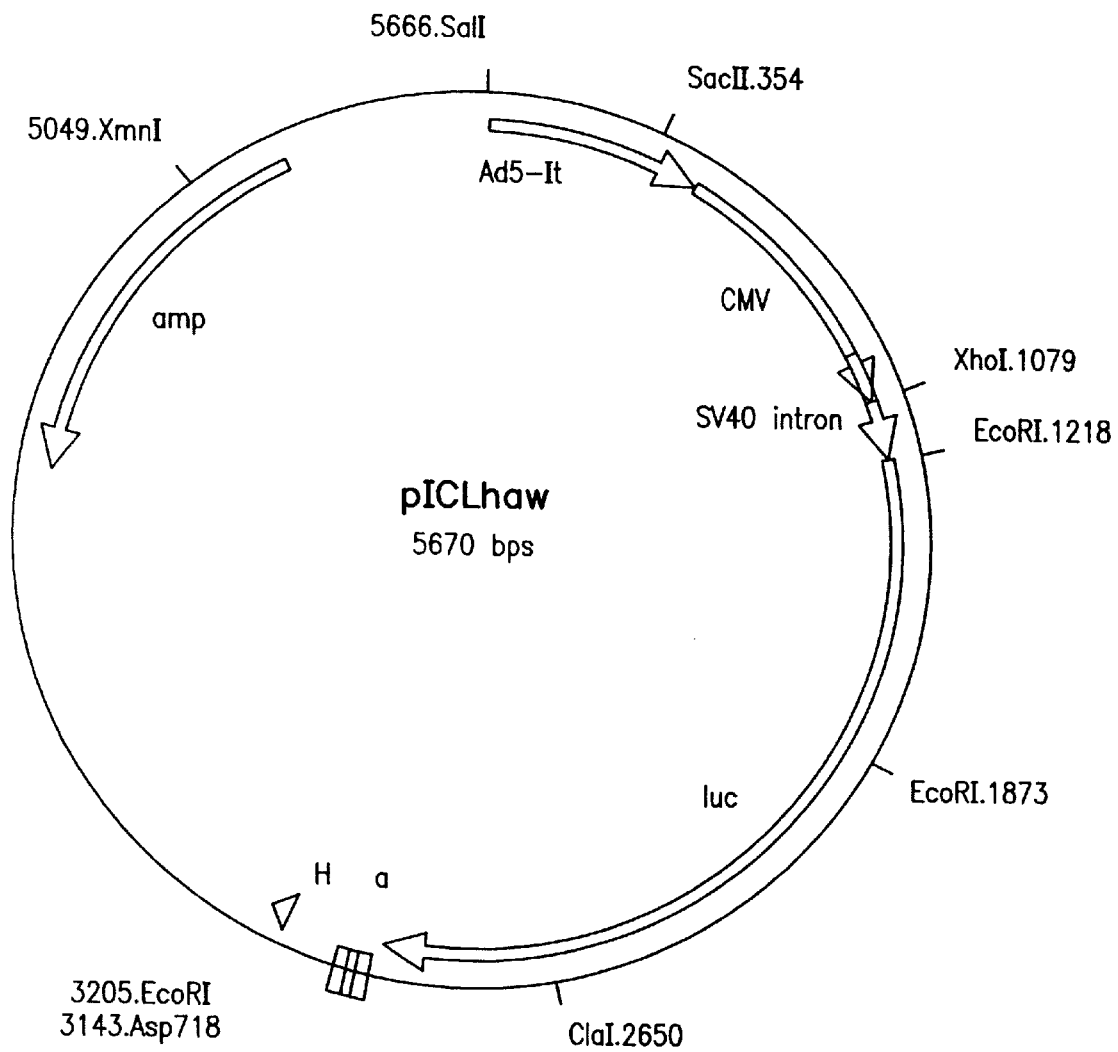

FIG. 17: Diagram of pICLhaw. pICLhaw is identical to pICLhac (FIG. 16) with the exception that the inserted HP/asp sequence is in the opposite orientation.

Figure 18:
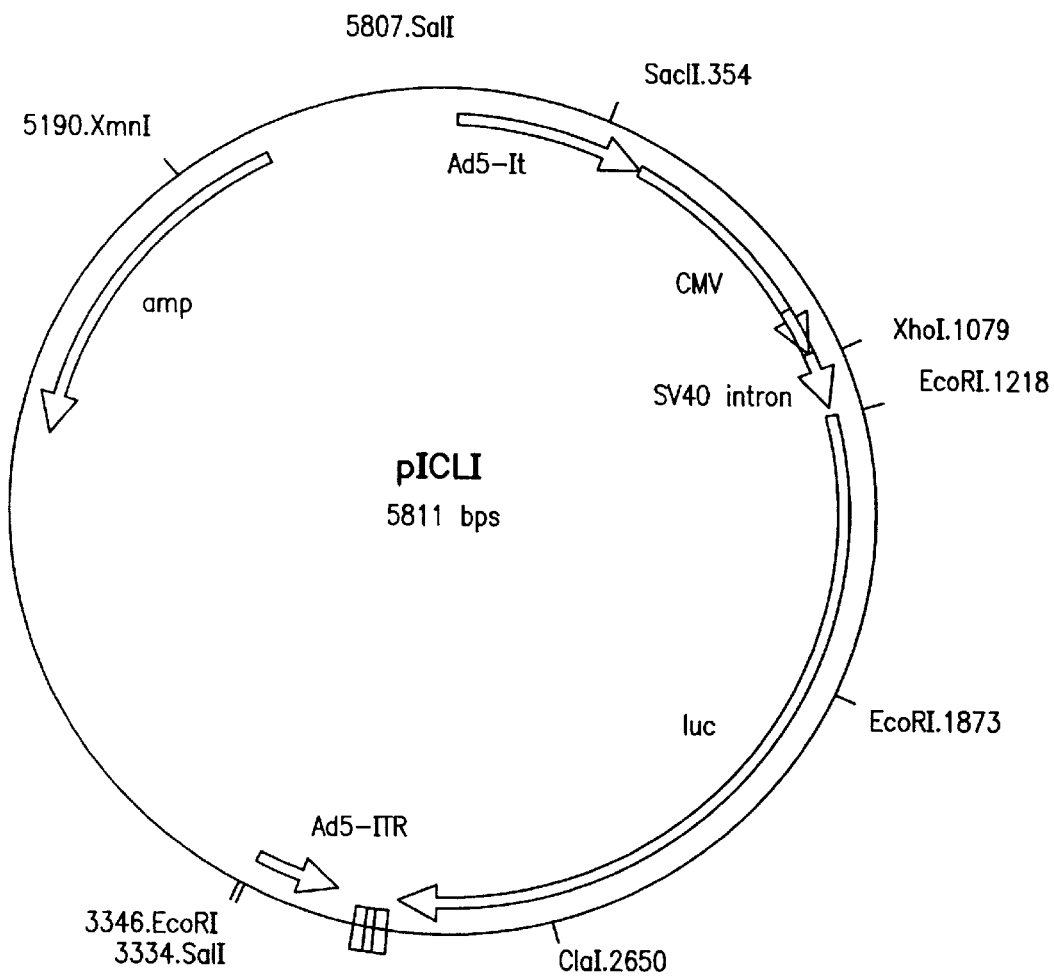

FIG. 18: Schematic representation of pICLI. pICLI contains all the elements of pICL (FIG. 19) but also contains in the Asp718 site, an Ad5 ITR.

Figure 19:
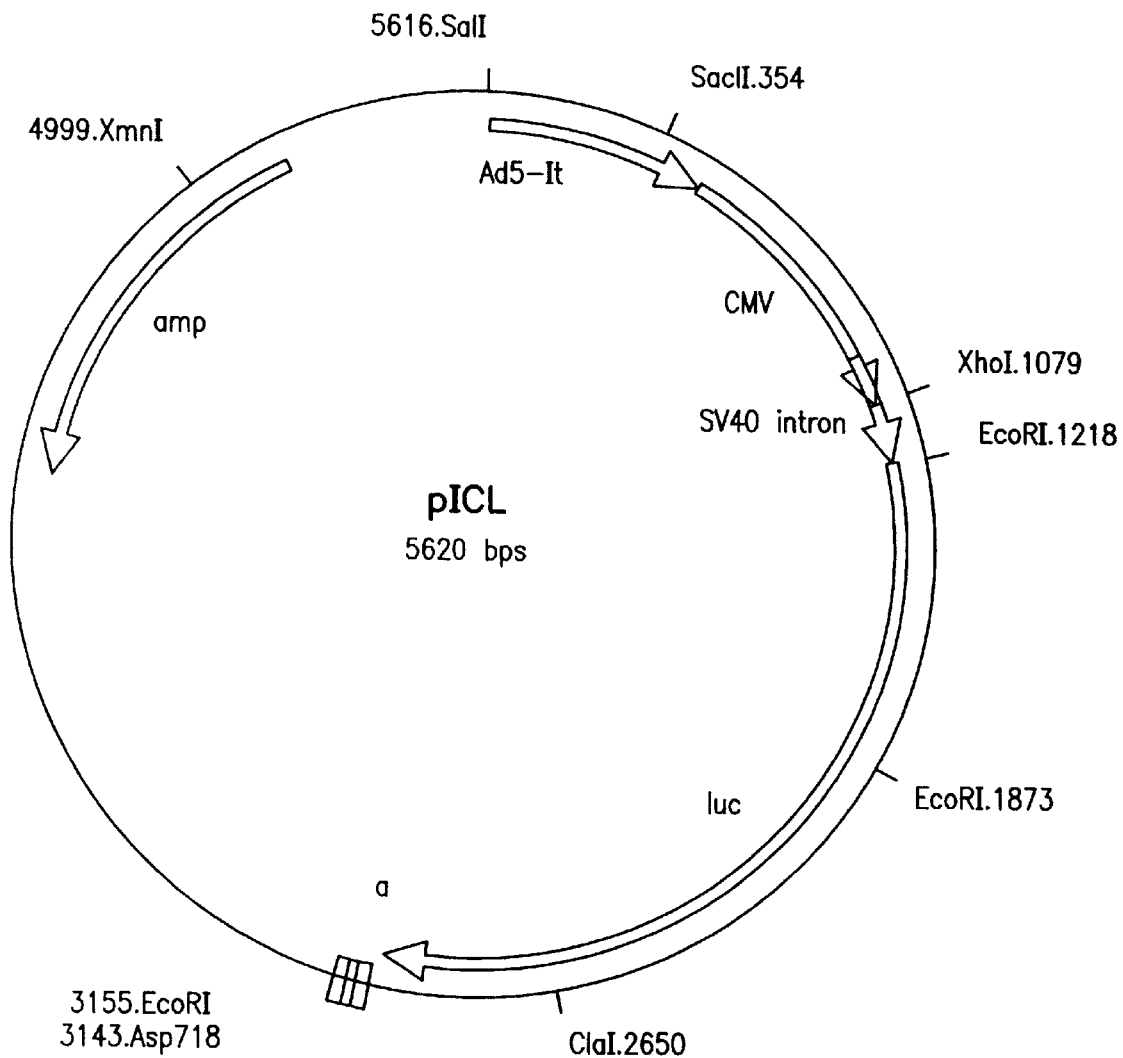

FIG. 19: Diagram of pICL. pICL is derived from the following: (i) nucleotides 1–457, Ad5 nucleotides 1–457 including the left ITR, (ii) nucleotides 458–969, human CMV enhancer and immediate early promoter, (iii) nucleotides 970–1204, SV40 19S exon and truncated 16/19S intron, (iv) nucleotides 1218–2987, firefly luciferase gene, (v) nucleotides 3018–3131, SV40 tandem polyadenylation signals from the late transcript, (vi) nucleotides 3132–5620, pUC12 sequences including an Asp718 site, and (vii) ampicillin resistance gene in reverse orientation.

Figure 20:
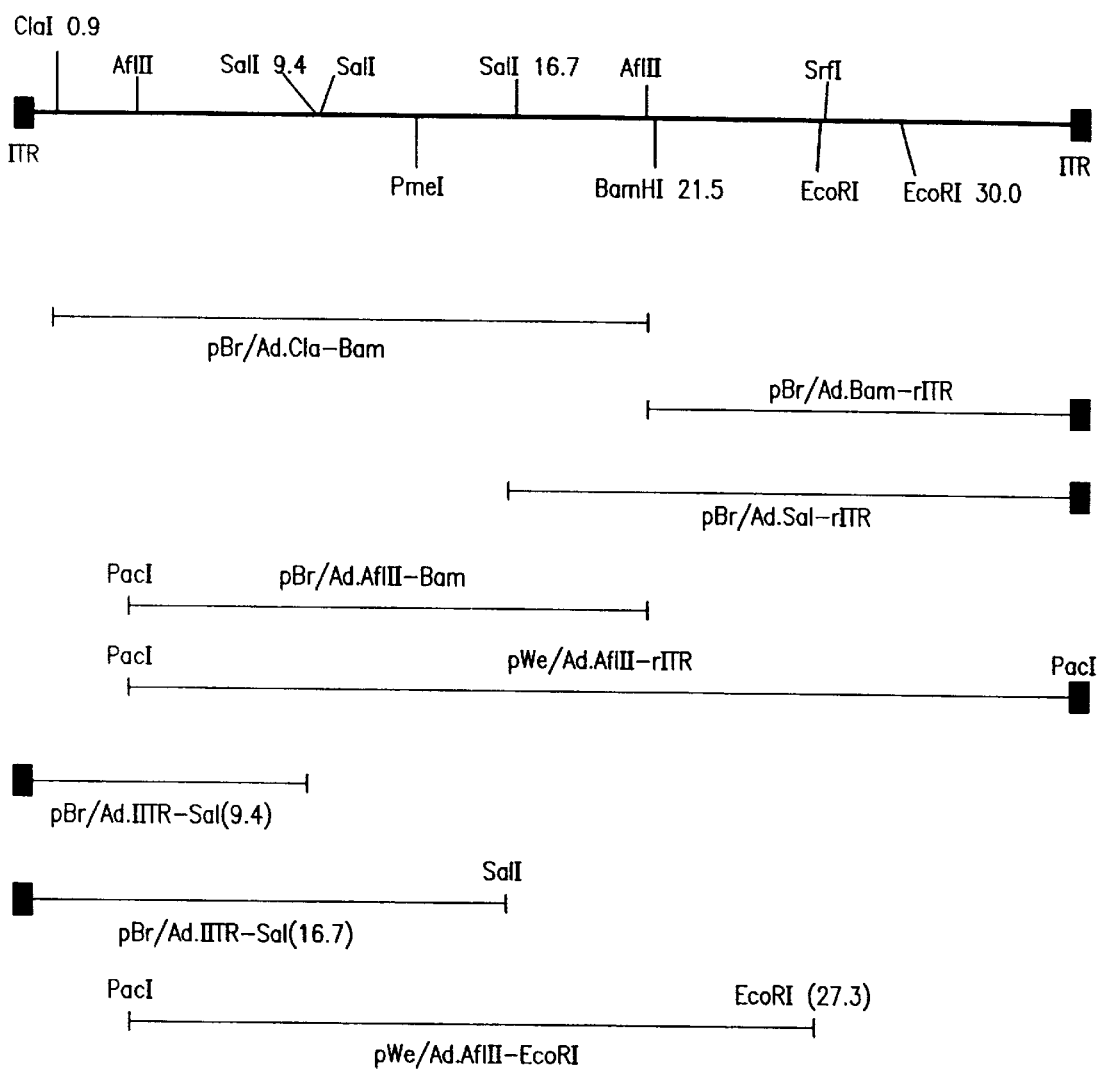

FIG. 20: Shows a schematic overview of the adenovirus fragments cloned in pBr322 (plasmid) or pWE15 (cosmid) derived vectors. The top line depicts the complete adenovirus genome flanked by its ITRs (filled rectangles) and with some restriction sites indicated. Numbers following restriction sites indicate approximate digestion sites (in kb) in the Ad5 genome.

Figure 21:
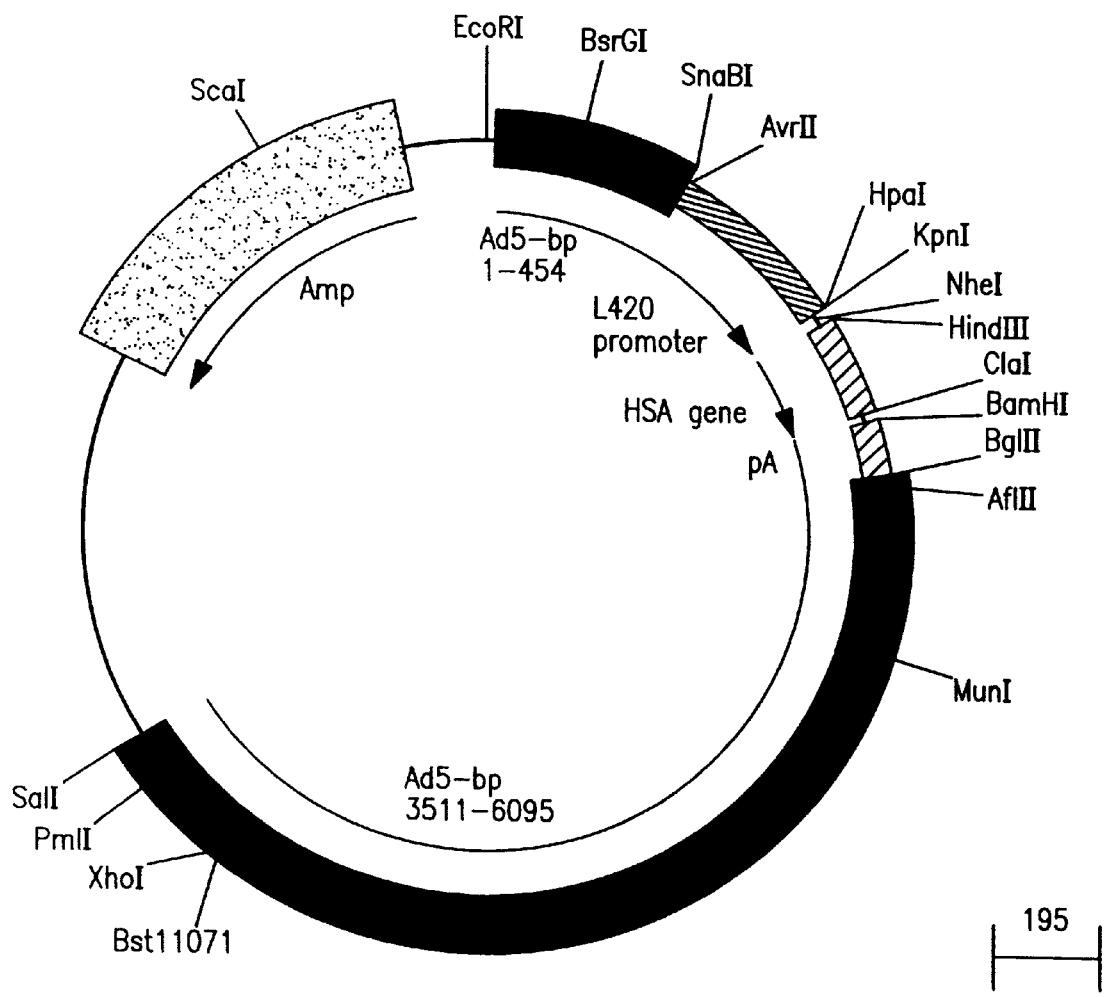

FIG. 21: Drawing of adapter plasmid pAd/L420-HSA

Figure 22:
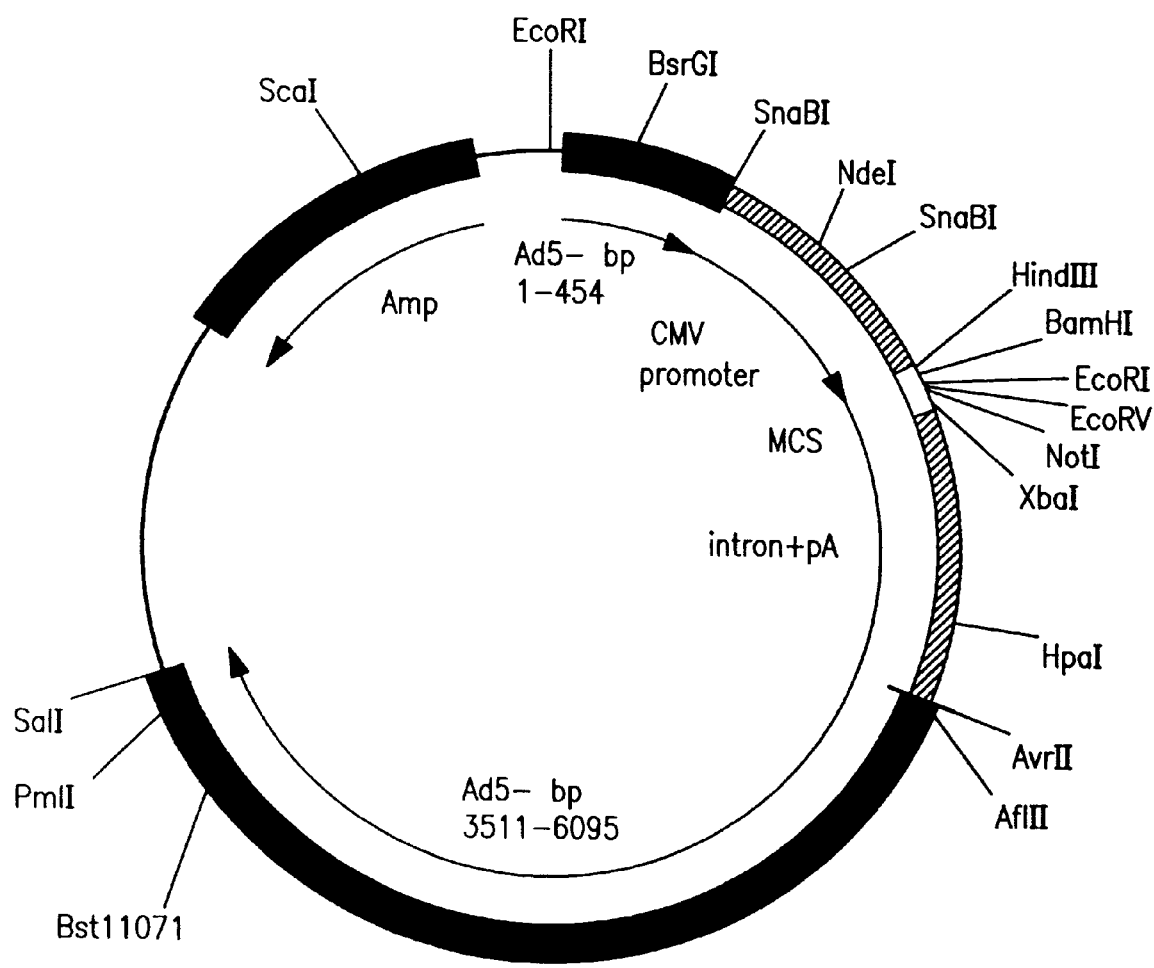

FIG. 22: Drawing of adapter plasmid pAd/Clip

Figure 23:
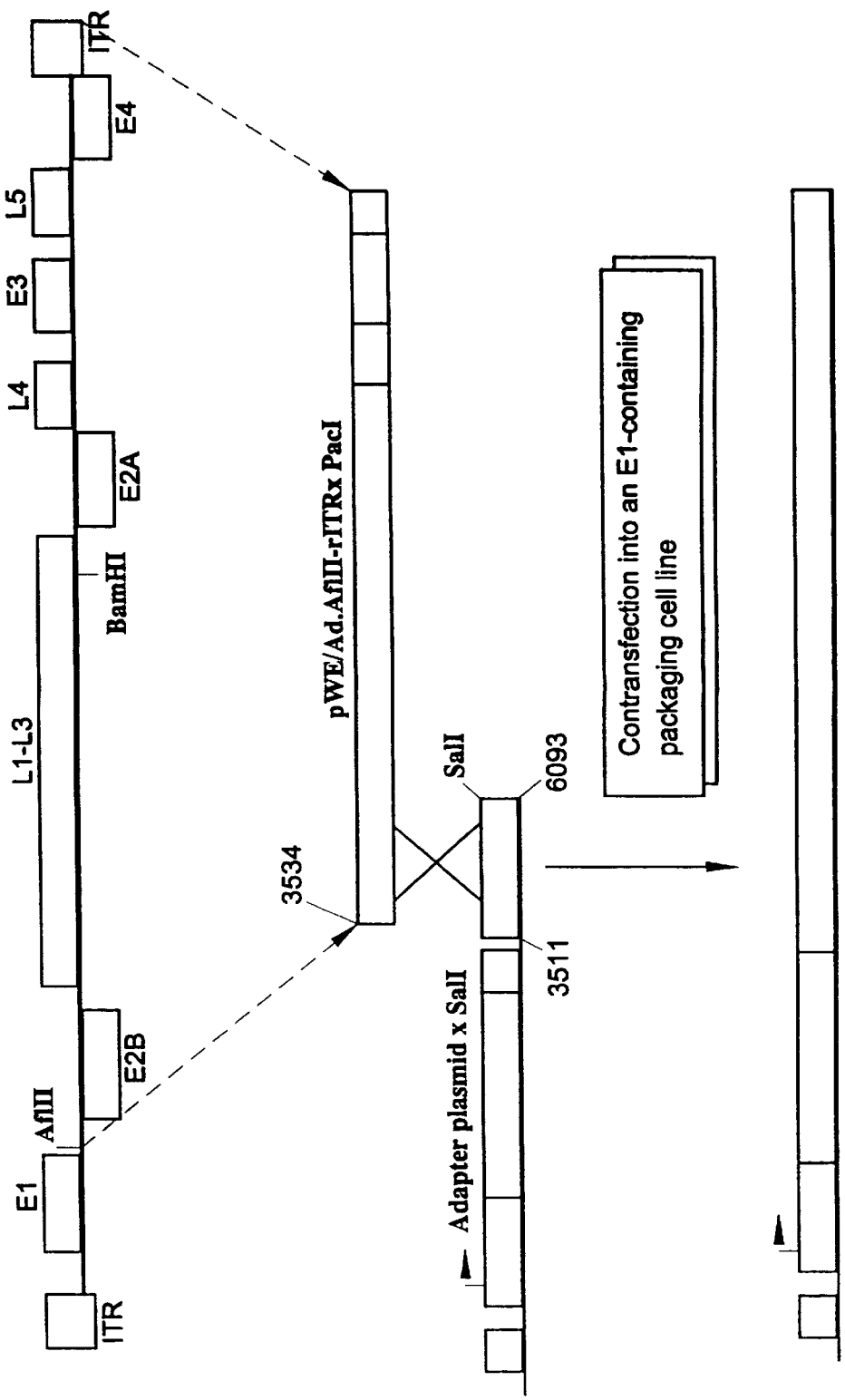

FIG. 23: Schematic presentation of the generation of recombinant adenoviruses using a plasmid-based system. In the top the genome organization of Ad5 is given with filled boxes representing the different early and late transcription regions, and flanking ITRs. The middle presents the two DNAs used for a single homologous recombination and, after transfection into packaging cells, leading to the recombinant virus (represented at the bottom).

Figure 24:
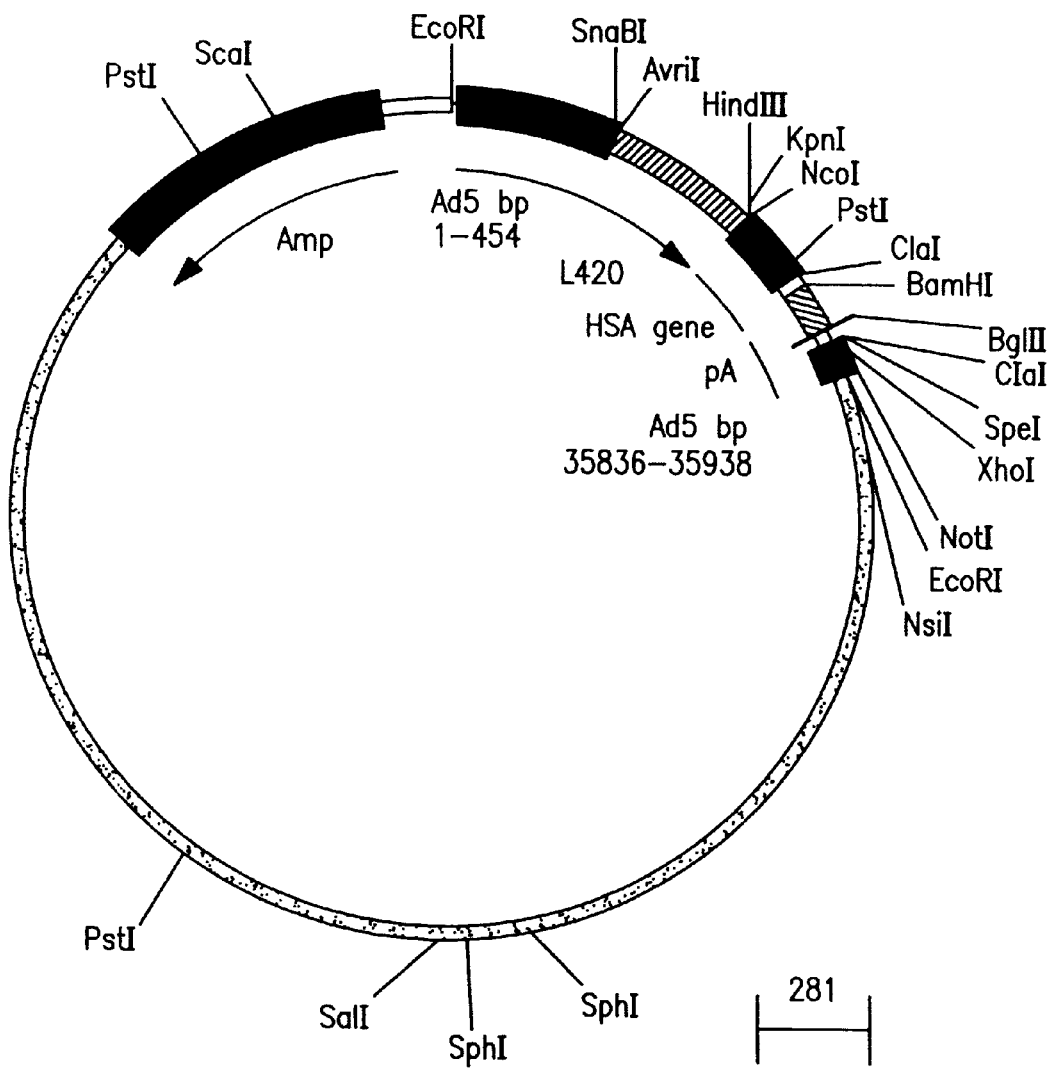

FIG. 24: Drawing of minimal adenoviral vector pMV/L420H

Figure 25:
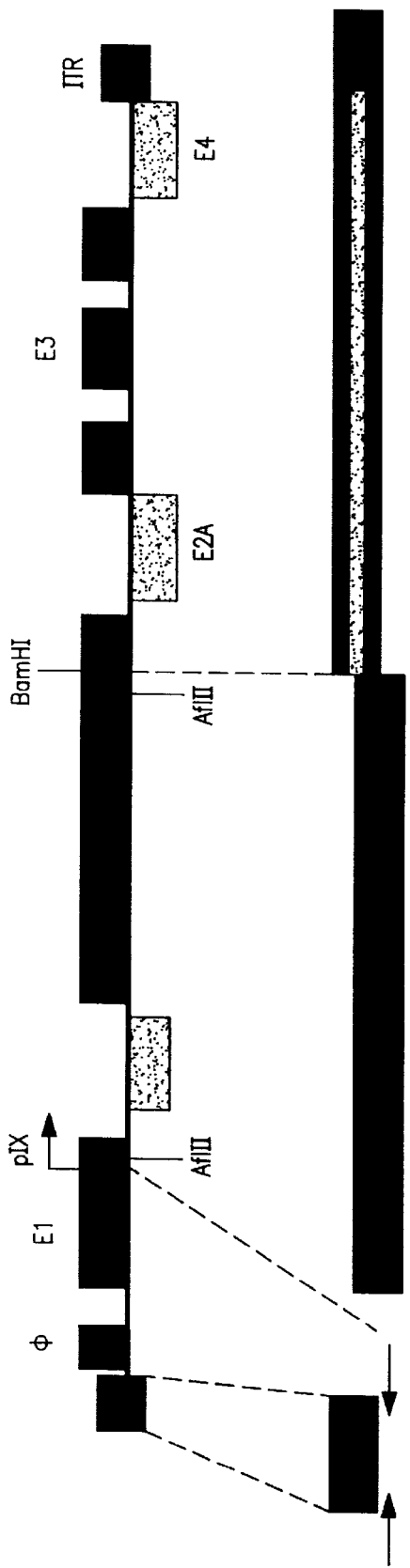

FIG. 25: Helper construct for replication and packaging of minimal adenoviral vectors. Schematic presentation of the cloning steps for the generation of the helper construct pWE/AdΔ5'.

Figure 26A:
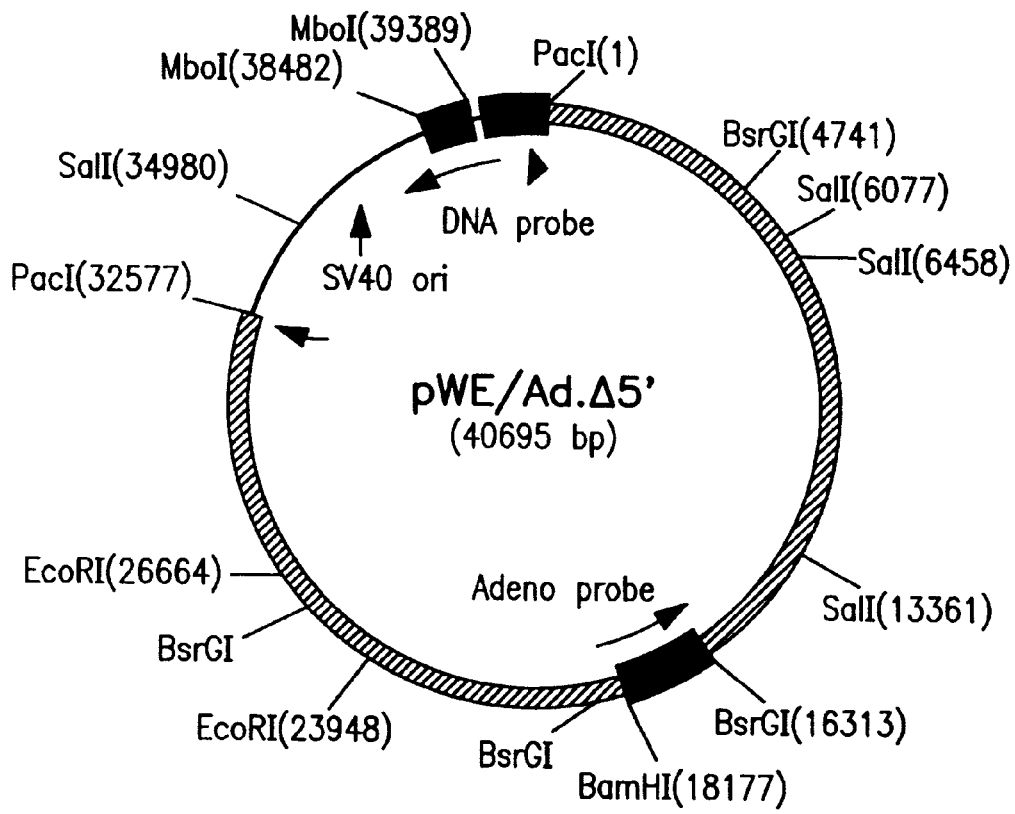
Figure 26B:
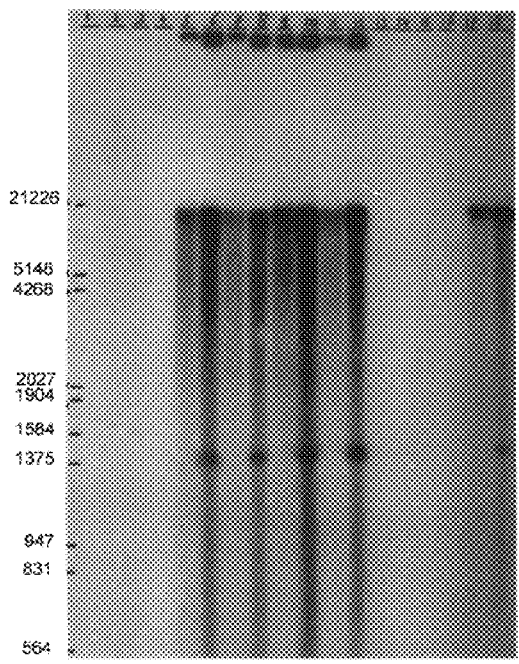
Figure 26C:
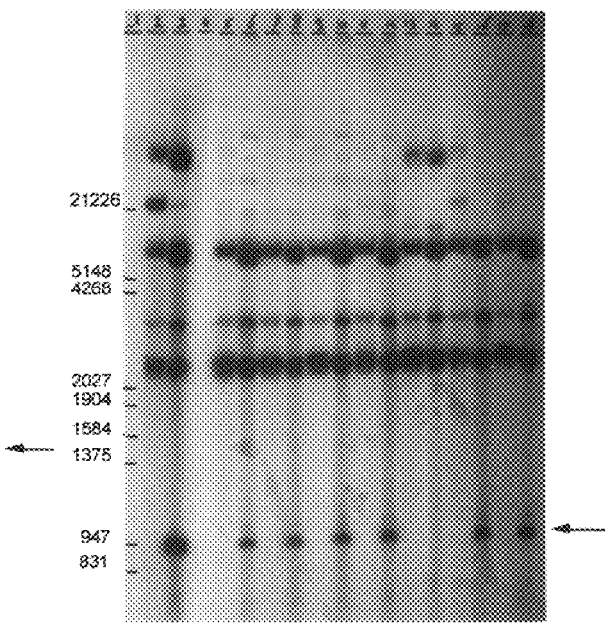

FIG. 26: Evidence for SV40-LargeT/ori mediated replication of large adenoviral constructs in COS-1 cells. FIG. 26A shows a schematic presentation of construct pWE/Ad.Δ5'. The location of the SV40 ori sequence and the fragments used to prepare probes are indicated. Evidence for SV40-LargeT/ori mediated replication of large adenoviral constructs in COS-1 cells. FIG. 26B shows an autoradiogram of the Southern blot hybridized to the adenovirus probe. FIG. 26C shows an autoradiogram of the Southern blot hybridized to the pWE probe. Lanes 1, marker lane: λ DNA digested with EcoRI and HindIII. Lane 4 is empty. Lanes 2, 5, 7, 9, 11, 13, 15 and 17 contain undigested DNA and Lanes 3, 6, 8, 10, 12, 14, 16 and 18 contain MboI digested DNA. All lanes contain DNA from COS-1 cells as described in the text transfected with pWE.pac (lanes 2 and 3), pWE/Ad.Δ5' construct #1 (lanes 5 and 6), #5 (lanes 7 and 8) and #9 (lanes 9 and 10), pWE/Ad.AflII-rITR (lanes 11 and 12), pMV/CMV-LacZ (lanes 13 and 14), pWE.pac digested with PacI (lanes 15 and 16) or pWE/Ad.AflII-rITR digested with PacI (lanes 17 and 18). Arrows point at the expected positive signal of 1416 bp (FIG. 26B) and 887 bp (FIG. 26C).

BRIEF DESCRIPTION OF THE SPECIFIC EMBODIMENTS

The present invention uses high-throughput generation of recombinant adenoviral vector libraries containing of one or more sample nucleic acids followed by high-throughput screening of the adenoviral vector libraries in a host to alter the phenotype of a host as a means of assigning a function to expression product(s) of the sample nucleic acids. Libraries of E1-deleted adenoviruses are generated in a high-throughput setting using nucleic acid constructs and transcomplementary packaging cells. The sample nucleic acid libraries can be a set of distinct defined or undefined sequences or can be a pool of undefined or defined sequences. The first nucleic acid construct is a relatively small and easy to manipulate adapter plasmid containing, in an operable configuration, at least a left ITR, a packaging signal, and an expression cassette with the sample nucleic acids. The second nucleic acid construct contains one or more nucleic acid molecules that partially overlap with each other and/or with sequences in the first construct and contains at least all adenovirus sequences necessary for replication and packaging of a recombinant adenovirus not provided by the adapter plasmid or packaging cells. The second nucleic acid construct is deleted in E1-region sequences and optionally E2B region sequences other than those required for virus generation and/or E2A, E3 and/or E4 region sequences. Cotransfection of the first and second nucleic acid constructs into the packaging cells leads to homologous recombination between overlapping sequences in the first and second nucleic acid constructs and among the second nucleic acid constructs when it is made up of more than one nucleic acid molecule. Generally the overlapping sequences are no more than 5000 bp and encompass E2B region sequences essential for virus production. Recombinant viral DNA is generated with an E1-deletion that is able to replicate and propagate in the E1-complementing packaging cells to produce a recombinant adenovirus vector library. The adenovirus vector library is introduced into a host in a high-throughput setting which is grown to allow sufficient expression of the product(s) encoded by the sample nucleic acids to permit detection and analysis of its biological activity. The host can be cultured cells in vitro or an animal or plant model. Sufficient expression of the product(s) encoded by the sample nucleic acids alters the phenotype of the host. Using any of a variety of in vitro and or in vivo assays for biological activity, the altered phenotype is identified and analyzed and function is thereby assigned to the product(s) of the sample nucleic acids. The plasmid-based adenovirus vector systems described here provides for the creation of large gene-transfer libraries that can be used to screen for novel genes applicable to human diseases. Identification of a useful or beneficial biological effect of a particular adenovirus mediated transduction can result in a useful gene therapeutic product or a target for a small molecule drug for treatment of human diseases.

There are several advantages to the subject invention over currently available techniques. The entire process lends itself to automation especially when implemented in a 96-well or other multi-well format. The high-throughput screening using a number of different in vitro assays provides a means of efficiently obtaining function information in a relatively short period of time. The member(s) of the recombinant adenoviral libraries that exhibit or induce a desired phenotype in a host in vitro or in situ are identified to collapse the libraries to a manageable number of recombinant adenovirus vectors or clones which can be tested in vitro in an animal model.

Another distinct advantage of the subject invention is that the methods produce RCA-free adenovirus libraries. RCA contamination throughout the libraries could become a major obstacle especially if libraries are continuously amplified for use in multiple screening programs. A further advantage of the subject invention is minimization of the number of steps involved in the process. The methods of the subject invention do not require cloning of each individual adenovirus before use in a high throughput screening program. Other systems include one or more steps in *E. coli* to achieve homologous recombination for the various adenoviral plasmids necessary for vector generation (Chartier et al., (1996) *J. Virol.* 70(7):4805–4810; Crouzet et al., (1997) *Proc. Natl. Acad. Sci* 94(4):1414–1419; He et al., (1998) *Proc. Natl. Acad. Sci.* 95(5):2509–2514). Another plasmid system that has been used for adenoviral recombination and adenoviral vector generation and which is based on homologous recombination in human cells is the pBHG series of plasmids. However, this is used in 293 cells, the plasmids have overlap with E1 sequences plus the plasmid pBHG contains two ITRs closely together which leads to instability of the plasmid. All these features are undesirable and lead to RCA production or otherwise erroneous adenovirus vector production (Bett et al., (1994) *Proc. Nati. Acad. Sci. USA* 91(19):8802–8806). The recombinant nucleic acids of the subject invention have been designed to avoid constructions with these undesirable features.

A further advantage of the subject invention is the ability of recombinant adenoviruses to efficiently transfer and express recombinant genes in a variety of mammalian cells and tissues in vitro and in vivo resulting in the high expression of the transferred sample nucleic acids. The ability to productively infect quiescent cells, further expands the utility of the recombinant adenovirus libraries. In addition, high expression levels insure that the product(s) of the sample nucleic acids will be expressed to sufficient levels to induce a change in the phenotype of a host that can be detected and allow the function of the product(s) encoded by the sample nucleic to be determined.

The sample nucleic acids can be genomic DNA, cDNA, previously cloned DNA, genes, ESTs, synthetic double stranded oligonucleotides, or randomized sequences derived from one or multiple related or unrelated sequences and can be directly expressed as a polypeptide, antisense nucleic acid or genetic suppressor element (GSE). The sample nucleic acid sequences can be obtained from any organism including mammals (for example, man, monkey, mouse), fish (for example, zebrafish, pufferfish, salmon), nematodes (for example, *C. elegans*), insects (for example, Drosophila), yeasts, fungi, bacteria, and plants. Alternatively, the sample nucleic acids are prepared as synthetic oligonucleotides using commercially available DNA synthesizers and kits. The strand coding the open reading frame of the polypeptide or product of the sample nucleic acid and the complementary strand are prepared individually and annealed to form double-stranded DNA. Special annealing conditions are not required. The sequences of the sample nucleic acids can be randomized or not through mutagenizing or methodologies promoting recombination. The sample nucleic acids code for a product(s) for which a biological activity is unknown. The phrase "biological activity" is intended to mean an activity which is detectable or measurable either in situ, in vivo or in vitro. Examples of a biological activity include but are not limited to altered viability, morphologic changes, apoptosis induction, DNA synthesis, tumorigenesis, disease or drug susceptibility, chemical responsiveness or secretion, and protein expression.

The sample nucleic acids preferably contain compatible ends to facilitate ligation to the vector in the correct orientation and to operatively link the sample nucleic acids to a promoter. For the example of synthetic double-stranded oligonucleotide ligation, the ends compatible to the vector can be designed into the oligonucleotides. When the sample nucleic acid is ESTS, genomic DNA, cDNA, genes or a previously-cloned DNA, the compatible ends can be formed by restriction enzyme digestion or the ligation of linkers to the DNA containing the appropriate restriction enzyme sites. Alternatively, the vector can be modified by the use of linkers. The restriction enzyme sites are chosen so that transcription of the sample nucleic acid from the vector produces the desired product, i.e., polypeptide, antisense nucleic acid, or GSE.

The vector into which the sample nucleic acids are preferably introduced contains, inoperable configuration, an ITR, at least one cloning site or preferably, a multiple cloning site, for insertion of a library of sample nucleic acids, and transcriptional regulatory elements for delivery and expression of the sample nucleic acid in a host. It generally does not contain E1 region sequences, E2B region sequences other than those required for late gene expression, E2A region sequences, E3 region sequences or E4 region sequences. The E1-deleted delivery vector or adapter plasmid is digested with the appropriate restriction enzymes, either simultaneously or sequentially, to produce the appropriate ends for directional cloning of the sample nucleic acid whether it be synthetic double-stranded oligonucleotides, genomic DNA, cDNA, ESTs, or a previously-cloned DNA. Restriction enzyme digestion is routinely performed using commercially available reagents according to the manufacturer's recommendations and varies according to the restriction enzymes chosen. A distinct set or pool of sample nucleic acids is inserted into E1-deleted adapter plasmid to produce a corresponding set or library of plasmids for the production of adenovirus vectors. An example of an adapter plasmid is pMLPI.TK which is made up of adenovirus nucleotides 1–458, followed by the adenovirus major late promoter, functionally linked to the herpes simplex virus thymidine kinase gene, and followed by adenovirus nucleotides 3511–6095. Other examples of adapter plasmids are pAd/L420-HSA (FIG. 21) and pAd/Clip (FIG. 22). pAd/L420-HSA contains adenovirus nucleotides 1–454, the L420 promoter linked to the murine HSA gene, a poly-A signal followed by adenovirus nucleotides 3511–6095. pAd/CLIP was made from pAd/L420-HSA by replacement of the expression cassette (L420-HSA) with the CMV promoter, a multiple cloning site, an intron and a poly-A signal.

Once digested, the vector and sample nucleic acids are purified by gel electrophoresis. The nucleic acids can be extracted from various gel matrices by, for example, agarase digestion, electroelution, melting, or high salt extraction. In combination with these methods or alternatively, the digested nucleic acids can be purified by chromatography (e.g. Qiagen or equivalent DNA binding resins) or phenol-chloroform extraction and ethanol precipitation. The optimal purification method depends on the size and type of the vector and sample nucleic acids. Both can be used without purification.

Generally, the sample nucleic acids contain 5'-phosphate groups and the vector is treated with alkaline phosphatase to promote nucleic acid-vector ligation and prevent vector-vector ligation. If the sample nucleic acid is a synthetic oligonucleotide, 5'-phosphate groups are added by chemical or enzymatic means. For ligation, molar ratios of sample nucleic acids (insert) to vector DNA range from approximately 10:1 to 0.1:1. The ligation reaction is performed using T4 DNA ligase or any other enzyme that catalyzes double-stranded DNA ligation. Reaction times and temperature can vary from about 5 minutes to 18 hours, to from about 15° C. to room temperature, respectively.

The magnitude of expression can be modulated using promoters (CMV immediately early, promoter, SV40 promoter, retrovirus LTRs) that differ in their transcriptional activity. Operatively linking the sample nucleic acid to a strong promoter such as the CMV immediate early promoter and optionally one or more enhancer element results in higher expression allowing the use of a lower multiplicity of infection to alter the phenotype of a host. The option of using a lower multiplicity of infection increases the number of times a library can be used in situ, in vitro and in vivo. Moreover, the lower the virus library multiplicity of infection and dosages used in screening programs, assays and animal models decreases the chance of eliciting toxic effects in the transduced host, increasing again the reliability of the system subject of this invention. Another way to reduce possible toxic effects relating to expression of the library is to use a regulatable promoter, particularly one which is repressed during virus production, but which can be turned on or is active during functional screenings with the adenoviral library, to provide temporal and/or cell type specific control throughout the screening assay. In this way, sample nucleic acids that are members of the library and which are toxic or inhibitory to the complementing cell line or which in any other way interfere with adenovirus replication and production can still be produced as an adenoviral vector (see WO 97/20943). Examples of this type of promoter are the AP1-dependent promoters which are repressed by adenoviral E1 gene products, resulting in shut off of sample nucleic acid expression during adenoviral library production (see van Dam et al., (1990) *Mol. Cell. Biol.* 10(11):5857–5864). Such a promoter can be made using combinatorial techniques or natural or adapted forms of promoters can be included. Examples of AP1-dependent promoters are promoters from the collagenase, c-myc, monocyte chemoattractant protein (JE or mcp-1/JE) and stromelysin genes (Hagmeyer et al., (1993) EMBO J. 12(9);3559–3572; Offringa et al., (1990) Cell 62(23):527–538; Offringa et al., (1988) *Nucleic Acids Res.* 16(23):10973–10984; van Dam et al., (1989) *Oncogene* 4(10):1207–1212). Alternatively, other more specific but stronger promoters can be used especially when complex in vitro screenings are employed or in vivo models are employed and tissue-regulated expression is desired. Any promoter/enhancer system functional in the chosen host can be used. Examples of tissue-regulated promoters include promoters with specific activity or enhanced activity in liver, such as the albumin promoter (Tronche et al., (1990) *Mol. Biol. Med.* 7(2):173–185). Another approach to enhanced expression is to increase the half-life of the mRNA transcribed from the sample nucleic acids by including stabilizing sequences in the 3' untranslated region. A second nucleic acid construct, a helper plasmid having sequences homologous to sequences in the E1-deleted adapter plasmids, which carries all necessary adenoviral genes necessary for replication and packaging, also is prepared. Preferably, the helper plasmid has no complementing sequences that are expressed by the packaging cells that would lead to production of replication competent adenovirus. In addition, preferably the helper plasmids, adapter plasmid and packaging cell have no sequence overlap that would lead to homologous recombination and RCA formation. The region of sequence overlap shared between the adapter plasmid and the helper plasmid allows homologous recombination and the formation of an E1-deleted, replication-defective recombinant adenovirus genome. Generally the region of overlap encompasses E2B region sequences that are required for late gene expression. The amount of overlap which provides for the best efficiency without appreciably decreasing the size of the library insert can be determined empirically. The sequence overlap is generally 10 bp to 5000 bp, more preferably 2000 to 3000 bp.

The size of the sample nucleic acids or DNA inserts in a desired adenovirus library can vary from several hundred base pairs (e.g., sequences encoding neuropeptides) to more than 30 Kbp (e.g., titin). The cloning capacity of the adenoviral vectors produced using adapter plasmids can be increased by deletion of additional adenoviral gene(s) that are then easily complemented by a derivative of an E1-complementing cell line. As an example, candidate genes for deletion include E2, E3, and/or E4. For example, regions essential for adenovirus replication and packaging are deleted from the adapter and helper plasmids and expressed, for example, by the complementing cell line. For E3 deletions, genes in this region do not need to be complemented in the packaging cell for in vitro models, and for in vivo models, the impact upon immunogenicity of the recombinant virus can be assessed on an ad hoc basis.

The set or library of specific adapter plasmids or pool(s) of adapter plasmids is converted to a set or library of adenoviral vectors. The adapter plasmids containing the sample nucleic acids are linearized and transfected into an E1-complementing cell line preferably seeded in microtiter tissue culture plates with 96, 384, 1,536 or more wells per plate, together with helper plasmids having sequences homologous to sequences in the adapter plasmid and containing all adenoviral genes necessary for replication and packaging. Recombination between the homologous sequences shared by adapter and helper plasmids to generate an E1-deleted, replication-defective adenovirus genome that is replicated and packaged, preferably, in an E1-complementing cell line. If more than one helper plasmid is used, recombination between homologous regions shared among the helper plasmids on the one hand and homologous recombination with the adapter plasmid results in the formation of a replication-defective recombinant adenovirus genome. The regions of sequence overlap between among the adapter and helper plasmids can vary from about a few hundred nucleotides or greater. Recombination efficiency will increase by increasing the size of the overlap.

The E1-functions provided by the transcomplementing packaging cell permits the replication and packaging of the E1-deleted recombinant adenovirus genome. The adapter and/or helper plasmids preferably have no sequence overlap amongst themselves or with the complementing sequences in the packaging cells that can lead to the formation of replication competent adenovirus (RCA). Preferably, at least one of the ITRs on the adapter and helper plasmids is flanked by a restriction enzyme recognition site not present in the adenoviral sequences or expression cassette so that the ITR is freed from vector sequences by digestion of the DNA with that restriction enzyme. In this way, initiation of replication occurs more efficiently. In order to increase the efficiency of recombinant adenovirus generation higher throughput can be obtained by using microtiter tissue culture plates with 96, 384 or 1,536 wells per plate instead of using large tissue culture vials or flasks. E1-complementing cell lines are grown in microtiter plates and co-transfected with the libraries of adapter plasmids and a helper plasmid(s). Automation of the method using, for example, robotics can further increase the number of adenovirus vectors that can be produced (Hawkins et al., (1997) *Science* 276(5320):1887–9, Houston, (1997) *Methods Find. Exp. Clin. Pharmacol.* 19 Suppl. A:43–5).

As an alternative to the adapter plasmids, the sample nucleic acids can be ligated to "minimal" adenovirus vector plasmids. The so-called "minimal" adenovirus vectors according to the present invention retain at least a portion of the viral genome that is required for encapsidation of the genome into virus particles (the encapsidation signal), as well as at least one copy of at least a functional part or a derivative of the Inverted Terminal Repeat (ITR), that is DNA sequences derived from the termini of the linear adenovirus genome that are required for replication. The minimal vectors preferably are used for the generation and production of helper- and RCA-free stocks of recombinant adenovirus vectors and can accommodate up to 38 kb of foreign DNA. The helper functions for the minimal adenovirus vectors are preferably provided in trans by encapsidation-defective, replication-competent DNA molecules that contain all the viral genes encoding the required gene products, with the exception of those genes that are present in the complementing cell, or genes that reside in the vector genome.

Packaging of the "minimal" adenovirus vector is achieved by cotransfection of an E1-complementing cell line with a helper virus or, alternatively, with a packaging deficient replicating helper system. Preferably, the packaging deficient replicating helper is amplified following transfection and expresses the sequences required for replication and packaging of the minimal adenovirus vectors that are not expressed by the packaging cell line. The packaging deficient replicating helper is not packaged into adenovirus particles because its size exceeds the capacity of the adenovirus virion and/or because it lacks a functional encapsidation signal. The packaging deficient replicating helper, the minimal adenovirus vector, and the complementing cell line, preferably, have no region of sequence overlap that permits RCA formation.

The replicating, packaging deficient helper molecule always contains all adenovirus coding sequences that produce proteins necessary for replication and packaging with or without the ones provided by the packaging cell line. Replication of the said helper molecule itself may or may not be mediated by adenovirus proteins and ITRs. Helper molecules that replicate through the activity of adenovirus proteins (that is E2-gene products acting together with cellular proteins) contain at least one ITR derived from adenovirus. The E2-gene products can be expressed by an E1-dependent or an E1-independent promoter. Where only one ITR is derived from an adenovirus, the helper molecule also preferably contains a sequence that anneals in an intramolecular fashion to form a hairpin-like structure.

Following E2-gene product expression, the adenovirus DNA polymerase recognizes the ITR on the helper molecule and produces a single-stranded copy and the 3'-terminus intramolecularly anneals, forming a hairpin-like structure that serves as a primer for reverse strand synthesis. The product of reverse strand synthesis is a double-strand hairpin with an ITR at one end. This ITR is recognized by adenovirus DNA polymerase which produces a double-stranded molecule with an ITR at both termini (see e.g. FIG. 13) and becomes twice as long as the transfected molecule (in our example it duplicates from 35 Kb to 70 Kb). Duplication of the helper DNA enhances the production of sufficient levels of adenovirus proteins. Preferably, the size of the duplicated molecule exceeds the packaging capacity of the adenovirus virion and is, therefore, not packaged into adenovirus particles. The absence of a functional encapsidation signal in the helper molecule further insures that the helper molecule is packaging deficient. The produced adenoviral proteins mediate replication and packaging of the cotransfected or co-infected minimal vectors.

When the replication of the helper molecule is independent of adenovirus E2-proteins, the helper construct preferably contains an origin of replication derived from SV40. Transfection of this DNA together with the minimal adenoviral vector in an E1-containing packaging cell line that also inducibly expresses the SV40 Large T protein, or as much SV40 derived proteins as necessary for efficient replication, leads to replication of the helper construct and expression of adenoviral proteins. These then initiate replication and packaging of the co-transfected or co-infected minimal adenoviral vectors. There are preferably no regions of sequence overlap shared by the replication-deficient packaging constructs, the minimal adenovirus vectors, and the complementing cell lines that may lead to the generation of RCA.

It is to be understood that during propagation of the minimal adenoviral vectors each amplification step on E1-complementing cells is preceded by transfection of any of the described helper molecules since minimal vectors by themselves can not replicate on E1-complementing cells. Alternatively, a cell line that contains all the adenoviral genes necessary for replication and packaging stably integrated in the genome and that can be excised and replicated conditionally can be used. (Valerio and Einerhand PCT/NL9800061).

Transfection of nucleic acid into cells is required for packaging of recombinant vectors into virus particles and can be mediated by a variety of chemicals including liposomes, DEAE-dextran, polybrene, and phosphazenes or phosphazene derivatives (WO97/07226). Liposomes are available from a variety of commercial suppliers and include DOTAP™ (Boehringer-Mannheim), Tfx™-50, Transfectam®, ProFection™ (Promega, Madison, Wis.), and LipofectAmin™, Lipofectin®, LipofectAce™ (GibcoBRL, Gaithersburg, Md.). In solution, the lipids form vesicles that associate with the nucleic acid and facilitate its transfer into cells by fusion of the vesicles with cell membranes or by endocytosis. Other transfection methods include, electroporation, calcium phosphate coprecipitation, and microinjection. If transfection conditions for a given cell line have not been established or are unknown, they can be determined empirically (Maniatis et al., "Molecular Cloning", pages 16.30–16.55).

The yield of recombinant adenovirus virus vectors can be increased by denaturing the double stranded plasmid DNAs before transfection into an E1 complementing cell line. Denaturing can be by melting double-stranded DNAs at, for example, 95–100° C., followed by rapid cooling using various ratios of the adapter and helper plasmids that have overlapping sequences. Also a PER.C6 derivative that stably or transiently expresses E2A (DNA binding protein) and/or E2B gene (pTP-Pol) could be used to increase the adenovirus production per well by increasing the replication rate per cell. Alternatively, cotransfection of recombinase protein(s) or recombinase DNA expression construct(s), i.e. recombinase from *Kluyveromyces waltii*, (Ringrose et al., (1997) *Eur. J. Biochem.* 248(3):903–912), or any other gene or genes encoding factors that can increase homologous recombination efficiency can be used. The inclusion of 0.1–100 mM sodium butyrate during transfection and/or replication on the packaging cells can increase virus production. These improvements will result in improved virus yields per microtiter well and thus the number and type of tests that can be done with one single library will increase and may overcome variability between the various genes or sample nucleic acids in a library.

The cell lines used for the production of adenovirus vectors that do express E1 region products includes, for example, 293 cells, PER.C6 (ECACC 96022940), or 911 cells. Each of these cell lines have been transfected with nucleic acids that encode for the adenovirus E1 region. These cells stably express E1 region gene products and have been shown to package E1-deleted recombinant adenovirus vectors. Yields of recombinant adenovirus obtained on PER.C6 cells are higher than obtained on 293 cells.

Each of these cell lines provide the basis for introduction of e.g. E2B or E2A constructs (e.g. tsl25E2A and/or hrE2A), or E4 etc., that permit the propagation of adenovirus vectors that have mutations, deletions or insertions in the corresponding genes. These cells can be modified to express additional adenovirus gene products by the introduction of recombinant nucleic acids that stably express the appropriate adenovirus genes or recombinant nucleic acids can be introduced that transiently express the appropriate gene(s), for example, the packaging deficient replicating helper molecules or the helper plasmids.

All or nearly all trans complementing cells grown in microtiter plate wells (96, 384, 1,536 or more wells) produce recombinant adenovirus following transfection with either the adapter plasmid or the minimal adenovirus plasmid library and the appropriate helper molecule(s). A large number of adenovirus gene transfer vectors or a library, each expressing a unique gene, can thus be conveniently produced on a scale that allows analysis of the biological activity of the particular gene products both in vitro and in vivo. Due to the wide tissue tropism of adenoviral vectors, a large number of cell and tissue types are transducable with an adenoviral library.

Libraries of genes or sample nucleic acids preferably are converted using the above methods to RCA free adenoviral libraries. The adenoviral libraries of genes or sample nucleic acids with unknown function are then used to perform high-throughput screening involving a number of in vitro assays, such as immunological assays including ELISAs, proliferation assays, drug resistance assays, enzyme activity assays, organ cultures, differentiation assays and cytotoxicity assays. Adenoviral libraries can be tested on tissues or tissue sections or tissue derived primary short-lived cell cultures including primary endothelial and smooth muscle cell cultures (Wijnberg et al., (1997) *Thromb Haemost* 78(2), 880–6), coronary artery bypass graft libraries, (Vassalli et al., (1997) *Cardiovasc Res.* 35(3), 459–69; Fuster and Chesebro, (1985) *Adv. Prostaglandin Thromboxane Leukot Res.* 13, 285–99), umbilical cord tissue including HUVEC (Gimbrone, (1976) *Prog. Hemost. Thromb.* 3, 1–28; Striker et al., (1980) *Methods Cell. Biol.* 21A, 135–51), couplet hepatocytes (Graf et al., (1984) *Proc. Natl. Acad. Sci. USA* 81(20), 6516–20), and epidermal cultures (Fabre, (1991) *Immunol. Lett.* 29(1–2), 161–5; Phillips, (1991) *Transplantation* 51(5), 937–41). Plant cell cultures, including suspension cultures, can also be used as host cells for the adenoviral libraries carrying any DNA sequence, including human derived DNA sequences and plant derived sequences. (de Vries et al., (1994) *Biochem. Soc. Symp.* 60, 43–50; Fukada et al., (1994) *Int. J. Devel. Biol.* 38(2), 287–99; Jones, (1983) *Biochem. Soc. Symp.* 48, 221–32; Kieran et al., (1997) *J. Biotechnol.* 59(1–2), 39–52; Stanley, (1993) *Curr. Opin. Genet. Dev.* 3(1), 91–6; Taticek et al., (1994) *Curr. Opin. Biotechnol.* 5(2), 165–74.

Depending on the size of the initial unselected library, once an adenoviral library of genes has been collapsed by in vitro assays to a reasonable number of candidates, the adenoviruses can be tested in appropriate animal models. Examples of animal models that can be used include models for Alzheimer's disease, arteriosclerosis, transgenic animals which have altered expression of endogenous or exogenous genes including mice with gene(s) that have been inactivated, animals with cancers implanted at specific sites, cancer metastasis models, Parkinson disease models, human bone marrow chimeric mice such as NOD-SCID mice, and the like. As additional testing is required, the stocks of candidate adenoviruses can be expanded by passaging the adenoviruses under the appropriate transcomplementing conditions.

Depending on the animal model used adenoviral vectors or mixtures of pre-selected pools of adenoviral vectors can be instilled or applied or administered at appropriate sites in the desired animal such as lung (Sene et al., (1995) *Hum. Gene Ther.* 6(12): 1587–93) in non-human primates, brain of normal and apoE deficient mice (Robertson et al., (1998) *Neuroscience* 82(1):171–80.) for Alzheimer disease (Walker et al., (1997) *Brain Res. Brain Res. Rev.* 25(1):70–84) and Parkinson disease models (Hockman et al., (1971) *Brain Res.* 35(2):613–8.; Zigmond and Stricker, (1984) *Life Sci.* 35(1):5–18.), injected in the blood stream (e.g. intravenous) for liver disease models including liver failure and Wilson disease (Cuthbert, (1995) *J. Investig. Med.* 43(4):323–36; Karrer et al.,. (1984) *Curr. Surg.* 41(6):464–7) and tumor models including metastases models (Esandi et al., (1997) *Gene Ther.* 4(4):280–7; Vincent et al., (1996) *J. Neurosug.* 85(4):648-54; Vincent et al., (1996) *Hum. Gene Ther.* 7(2): 197–205). Injection of selected adenoviral vectors directly into the bone marrow of human chimeric NOD-SCID mice (Dick et al., (1997) *Stem Cells* 15 Suppl. 1:199–203; Mosier et al., (1988) *Nature* 335(6187):256–9). Finally selected adenovirus can be applied locally in for example the disease vascular tissue of restenosis animal models (Karas et al., (1992) *J. Am. Coll. Cardiol.* 20(2):467–74).

In addition, wet laboratory assays can be complemented by using an electronic version of the sequence database on which the adenoviral library is built. This allows, for example, protein motif searching and thus linking of new members of a family to known members with known function of the same family. The use of "Hidden Markow Models" (HMMs) (Eddy. (1996) *Proc. Natl. Acad. Sci. USA* 94(4):1414–1419) allows the establishment of novel families by distilling out essential features of a family and building a model of what the members should look like. Finally, this can be combined with structural data by using the threading approach using a known structure as the thread and trying to find putative structure without having determined the actual structure of the novel protein (Rastan and Beeley (1997) *Curr. Opin. Genet. Dev.* 7 (6):777–83). Naturally, the functional data obtained using adenoviral libraries made in accordance with the methods disclosed in this application is the foundation of the endeavor to find novel genes with expected or desired functions and will be the core of functional genomics. Finally, once the number of adenovirus vectors is at a level at which animal experiments can be performed, another addition to the method is to grow up the selection of candidate adenovirus vectors carrying the candidate genes. This can then be followed by purification of the clones by, for example, using adenovirus tagged in the Hi loop of the knob domain of the fiber. Alternatively, large scale HPLC analysis can be used in a semipreparative fashion to yield partially purified adenovirus samples for animal experiments or in vitro screenings where more purified adenovirus preparations are desired. Therefore, the described method and reagents allow rapid transfer of a collection of genes to in vivo studies of a limited number of animals which otherwise would be unfeasible. The automation of each of the steps of the procedure using robotics will further enhance the number of genes and sample nucleic acids that can be functionated.

EXAMPLES

Example 1

Generation of Cell Lines Able to Transcomplement E1 Defective Recombinant Adenovirus Vectors 911 Cell Line A cell line that harbors E1 sequences of adenovirus type 5, able to trans-complement E1 deleted recombinant adenovirus has been generated (Fallaux et al, (1996) *Hum. Gene Ther.* 7: 215–222). This cell line was obtained by transfection of human diploid human embryonic retinoblasts (HER)

with pAd5XhoIC, that contains nt. 80-5788 of Ad 5; one of the resulting transformants was designated 911. This cell line has been shown to be useful in the propagation of E1 defective recombinant adenovirus. It was found to be superior to the 293 cells. Unlike 293 cells, 911 cells lack a fully transformed phenotype, which most likely is the cause of performing better as adenovirus packaging line:

- plaque assays can be performed faster (4–5 days instead of 8–14 days on 293)
- monolayers of 911 cells survive better under agar overlay as required for plaque assays
- higher amplification of E1-deleted vectors.

In addition, unlike 293 cells that were transfected with sheared adenoviral DNA, 911 cells were transfected using a defined construct. Transfection efficiencies of 911 cells are comparable to those of 293.

New Packaging Constructs
Source of Adenovirus Sequences

Adenovirus sequences are derived either from pAd5.SalB, containing nt. 80–9460 of human adenovirus type 5 (Bernards et al, (1983) *Virology* 127:45–53) or from wild-type Ad5 DNA. PAd5.SalB was digested with SalI and XhoI and the large fragment was religated and this new clone was named pAd5.X/S. The pTN construct (constructed by Dr. R. Vogels, IntroGene, The Netherlands) was used as a source for the human PGK promoter and the NEO gene.

Human PGK Promoter and NEO$^R$ Gene

Transcription of E1A sequences in the new packaging constructs is driven by the human PGK promoter (Michelson et al, (1983) *Proc. Natl. Acad. Sci. USA* 80:472–476); Singer-Sam et al, (1984) *Gene* 32: 409–417), derived from plasmid pTN (gift of R. Vogels), which uses pUC119 (Vieira et al, (1987) pp. 3–11: *Methods in Enzymology*, Acad. Press Inc.) as a backbone. This plasmid was also used as a source for the NEO gene fused to the Hepatitis B Virus (HBV) poly-adenylation signal.

Figure 1:
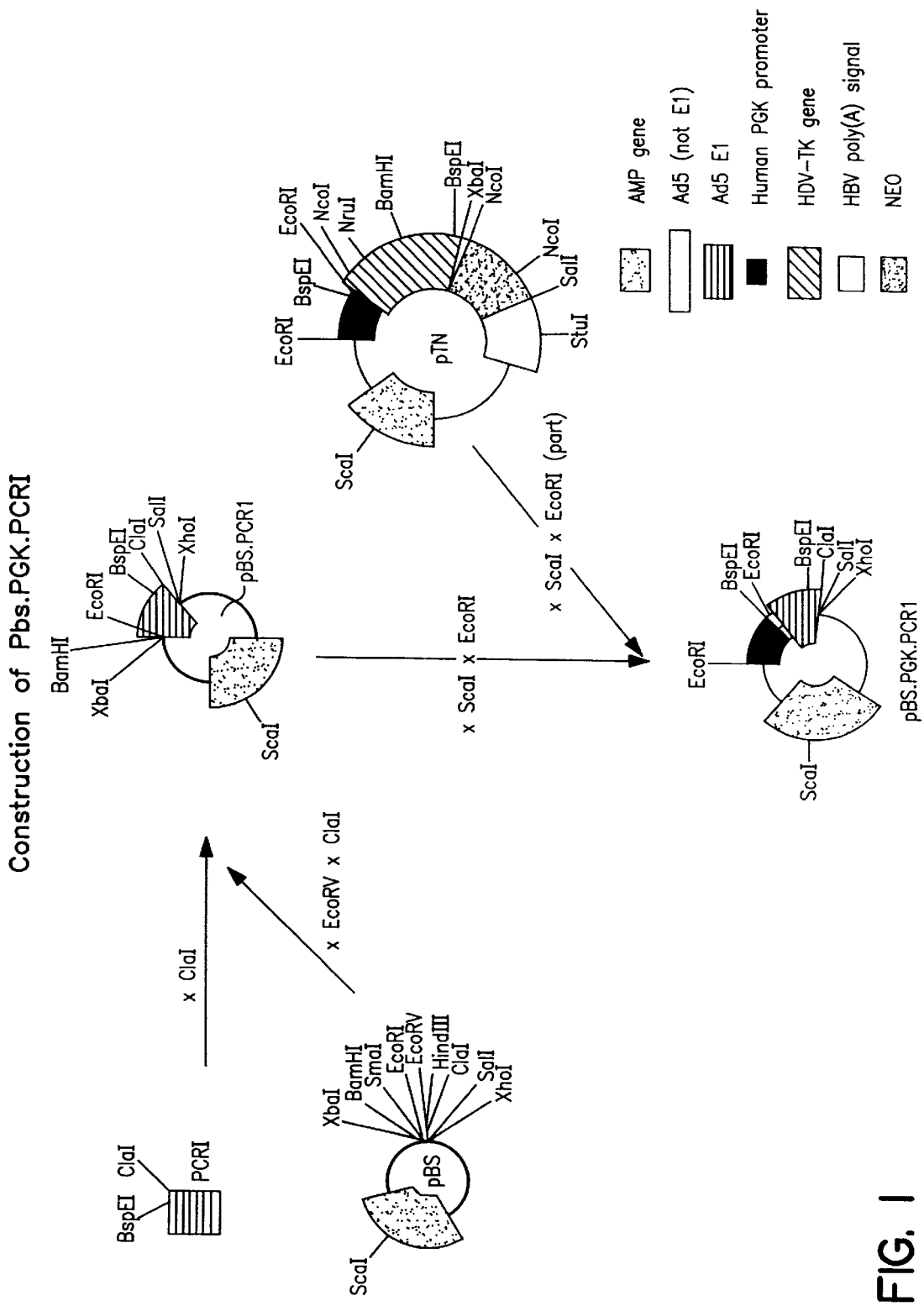
FIG. 1: Construction of pBS.PGK.PCRI.pBS.PGK.PCRI encodes the human phosphoglycerate kinase promoter (PGK) operatively linked to adenovirus 5 (Ad5) E1 nucleotides 459–916. To construct this plasmid, Ad5 nucleotides 459–916 were PCR amplified with primers Ea-1 (SEQ ID NO:27) and Ea-2 (SEQ ID NO:28), digested with Cla I and cloned into the Cla I-EcoR V sites of pBluescript (Stratagene), resulting in pBS.PCRI. The PGK promoter was excised from pTN by complete digestion with Sca I and partial digestion with EcoR I and cloned into the corresponding sites of pBS.PCRI, resulting in pBS.PGK.PCRI.

Fusion of PGK Promoter to E1 Genes (FIG. 1)

In order to replace the E1 sequences of Ad5 (ITR, origin of replication and packaging signal) by heterologous sequences we have amplified E1 sequences (nt.459 to nt.960) of Ad5 by PCR, using primers Ea1 (SEQ ID NO:27) and Ea2 (SEQ ID NO:28) (see Table I). The resulting PCR product was digested with ClaI and ligated into Bluescript (Stratagene), predigested with ClaI and EcoRV, resulting in construct pBS.PCRI.

Vector pTN was digested with restriction enzymes EcoRI (partially) and ScaI, and the DNA fragment containing the PGK promoter sequences was ligated into PBS.PCRI digested with ScaI and EcoRI. The resulting construct PBS.PGK.PCRI contains the human PGK promoter operatively linked to Ad5 E1 sequences from nt.459 to nt.916.

Figure 2:
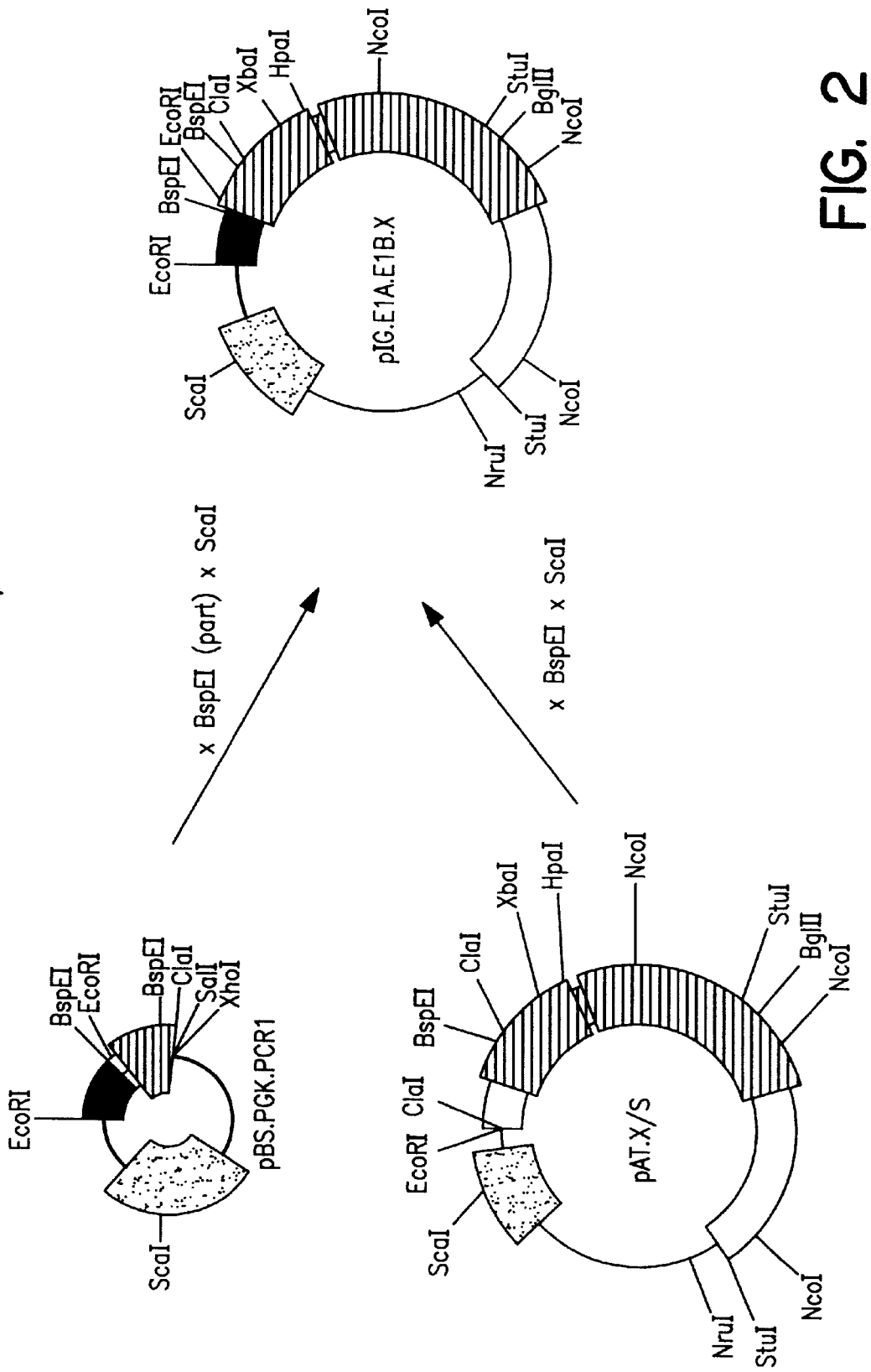
FIG. 2: Construction of pIG.E1A.E1B.X. pIG.E1A.E1B.X encodes Ad5 nucleotides 459–5788 (E1A and E1B regions) operatively linked to the human PGK promoter. pIG.E1A.E1B.X also encodes Ad5 pIX protein. pIG.E1A.E1B.X was constructed by replacing the Sca I-BspE I fragment of pAT-X/S with the corresponding fragment of pBS.PGK.PCRI.

Construction of pIG.E1A.E1B (FIG. 2)

PIG.E1A.E1B.X contains the E1A and E1B coding sequences under the direction of the PGK promoter. As Ad5 sequences from nt.459 to nt.5788 are present in this construct, also pIX protein of adenovirus is encoded by this plasmid. pIG.E1A.E1B.X was made by replacing the ScaI-BspEI fragment of pAT-X/S by the corresponding fragment from PBS.PGK.PCRI (containing the PGK promoter linked to E1A sequences).

Figure 3A:
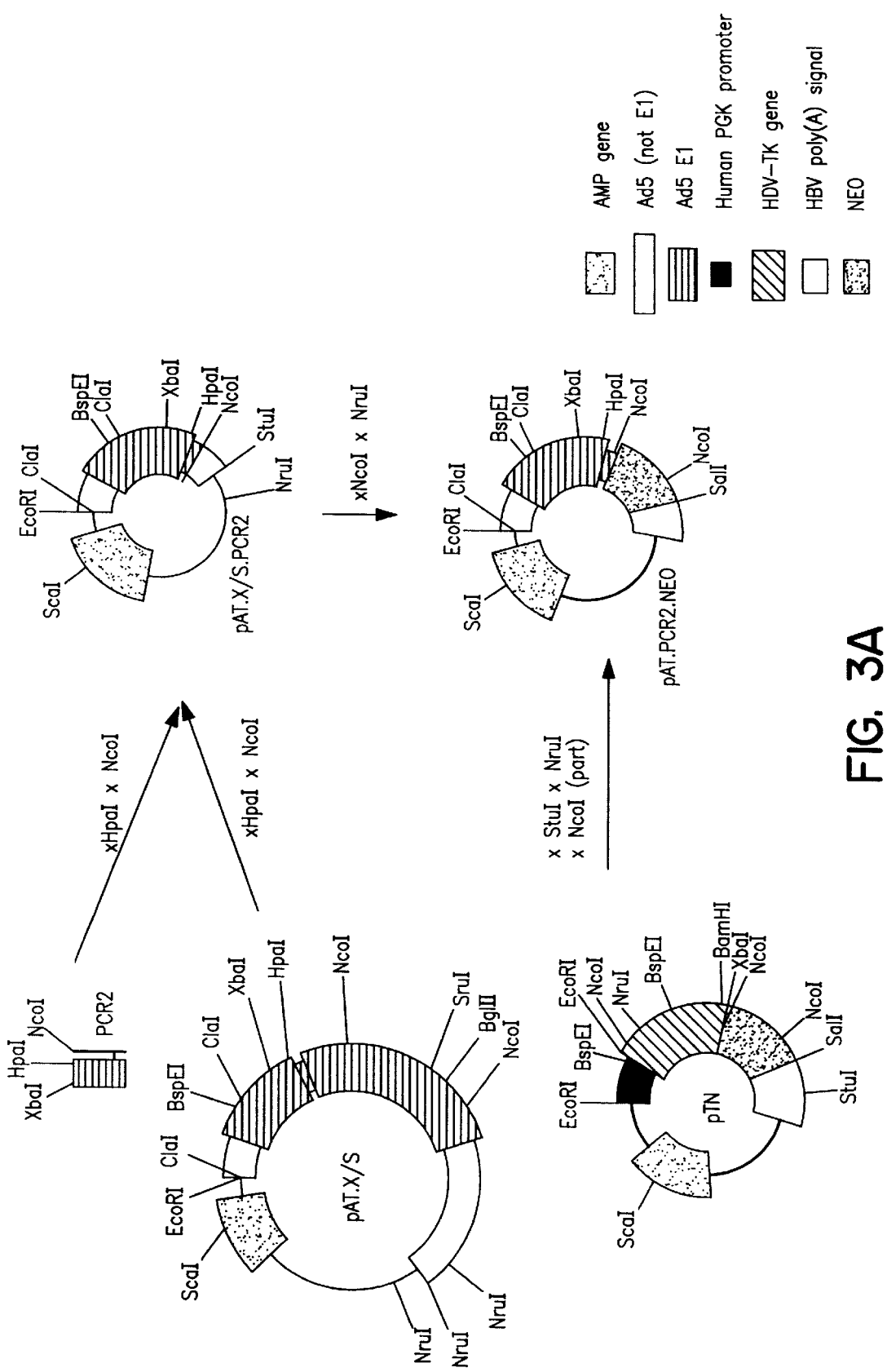
FIG. 3A: Construction of pAT-PCR2-NEO. To construct this plasmid, the E1B promoter and initiation codon (ATG) of the E1B 21 kDa protein were PCR amplified with primers Ea-3 (SEQ ID NO:29) and Ep-2 (SEQ ID NO:30), where Ep-2 introduces an Nco I site (5'-CCATGG) at the 21 kDa protein initiation codon. The PCR product (PCRII) was digested with Hpa I and Nco I and ligated into the corresponding sites of pAT-X/S, producing pAT-X/S-PCR2. The Nco I-Stu I fragment of pTN, containing the Neo$^R$ and a portion of the HBV poly(A) site were ligated into the Nco I-Nru I sites of pAT-X/S-PCR2, producing pAT-PCR2-NEO.

Construction of pIG.EIA.NEO (FIG. 3)

In order to introduce the complete E1B promoter and to fuse this promoter in such a way that the AUG codon of E1B 21 kD exactly functions as the AUG codon of NEO$^R$, the E1B promoter was amplified using primers Ea3 (SEQ ID NO:29) and Ep2 (SEQ ID NO:30), where primer Ep2 introduces a NcoI site in the PCR fragment. The resulting PCR fragment, named PCRII, was digested with HpaI and NcoI and ligated into pAT-X/S, which was predigested with HpaI and with NcoI. The resulting plasmid was designated pAT-X/S-PCR2. The NcoI-StuI fragment of pTN, containing the NEO gene and part of the

TABLE I

Primers used for PCR amplification of DNA fragments used for generation of constructs described in this patent application.

| | | | |
|---|---|---|---|
| Ea-1 | CGTGTAGTGTATTTATACCCG | (SEQ ID NO:27) | PCR amplification Ad5 nt.459 -> |
| Ea-2 | TCGTCACTGGGTGGAAAGCCA | (SEQ ID NO:28) | PCR amplification Ad5 nt.960 <- |
| Ea-3 | TACCCGCCGTCCTAAAATGGC | (SEQ ID NO:29) | nt.1284–1304 of Ad5 genome |
| Ea-5 | TGGACTTGAGCTGTAAACGC | (SEQ ID NO:43) | nt.1514–1533 of Ad5 genome |
| Ep-2 | GCCTCCATGGAGGTCAGATGT | (SEQ ID NO:30) | nt.1721–1702 of Ad5; introduction of NcoI site |
| Eb-1 | GCTTGAGCCCGAGACATGTC | (SEQ ID NO:31) | nt.3269–3289 of Ad5 genome |
| Eb-2 | CCCCTCGAGCTCAATCTGTATCTT | (SEQ ID NO:32) | nt.3508-3496 of Ad5 genome; introduction of XhoI site |
| SV40-1 | GGGGGATCCGAACTTGTTTATTGCAGC | (SEQ ID NO:33) | introduction BamHI site(nt.2182-2199 of pMLP.TK) adaption of recombinant adenoviruses |
| SV40-2 | GGGAGATCTAGACATGATAAGATAC | (SEQ ID NO:34) | introduction BglII site (nt.2312-2297 of pMLP.TK) |
| Ad5-1 | GGGAGATCTGTACTGAAATGTGTGGGC | (SEQ ID NO:35) | introduction Blg111 site (nt.2496-2514 of pMLP.TK) |
| Ad5-2 | GGAGGCTGCAGTCTCCAACGGCGT | (SEQ ID NO:36) | nt.2779-2756 of pMLP.TK |
| ITR1 | GGGGGATCCTCAAATCGTCACTTCCGT | (SEQ ID NO:44) | nt.35737–35757 of Ad5 (introduction of BamHI site) |
| ITR2 | GGGGTCTAGACATCATCAATAATATAC | (SEQ ID NO:45) | nt.35935-35919 of Ad5 (introduction of XbaI site) |
| PCR primer sets to be used to create the SalI and Asp718 sites juxtaposed to the ITR sequences. | | | |
| PCR/MLP1 GGCGAATTCGTCGACATCATCAATAATATACC | | (SEQ ID NO:37) | (Ad5 nt.10–18) |
| PCR/MLP2 GGCGAATTCGGTACCATCATCAATAATATACC | | (SEQ ID NO:46) | (Ad5 nt.10–18) |
| PCR/MLP3 CTGTGTACACCGGCGCA | | (SEQ ID NO:38) | (Ad5 nt.200-184) |
| Synthetic oligonucleotide pair used to generate a synthetic hairpin, recreates an Asp718 site at one of the termini if inserted in Asp718 site: | | | |
| HP/asp1 5'-GTACACTGACCTAGTGCCGCCCGGGCAAAGCCCGGGCGGCACTAGGTCAG | | (SEQ ID NO:39) | |
| HP/asp2 5'-GTACCTGACCTAGTGCCGCCCGGGCTTTGCCCGGGCGGCACTAGGTCAGT | | (SEQ ID NO:40) | |
| Synthetic oligonucleotide pair used to generate a synthetic hairpin, contains the ClaI recognition site to be used for hairpin formation. | | | |
| HP/cla1 5'-GTACATTGACCTAGTGCCGCCCGGGCAAAGCCCGGGCGGCACTAGGTCAATCGAT | | (SEQ ID NO:41) | |
| HP/cla2 5'-GTACATCGATTGACCTAGTGCCGCCCGGGCTTTGCCCGGGCGGCACTAGGTCAAT | | (SEQ ID NO:42) | |

Hepatitis B Virus (HBV) poly-adenylation signal, was cloned into pAT-X/S-PCR2 which had been digested with NcoI and NruI). The resulting construct was pAT-PCR2-NEO. The poly-adenylation signal was completed by replacing the ScaI-SalI fragment of pAT-PCR2.NEO with the corresponding fragment of pTN, resulting in pAT.PCR2.NEO.p (A). The ScaI-XbaI of pAT.PCR2.NEO.p (A) was replaced with the corresponding fragment of pIG.E1A.E1B-X, containing the PGK promoter linked to E1A genes. The resulting construct was named pIG.E1A.NEO, and thus contains Ad5 E1 sequences (nt.459 to nt.1713) under the control of the human PGK promoter.

Figure 4:
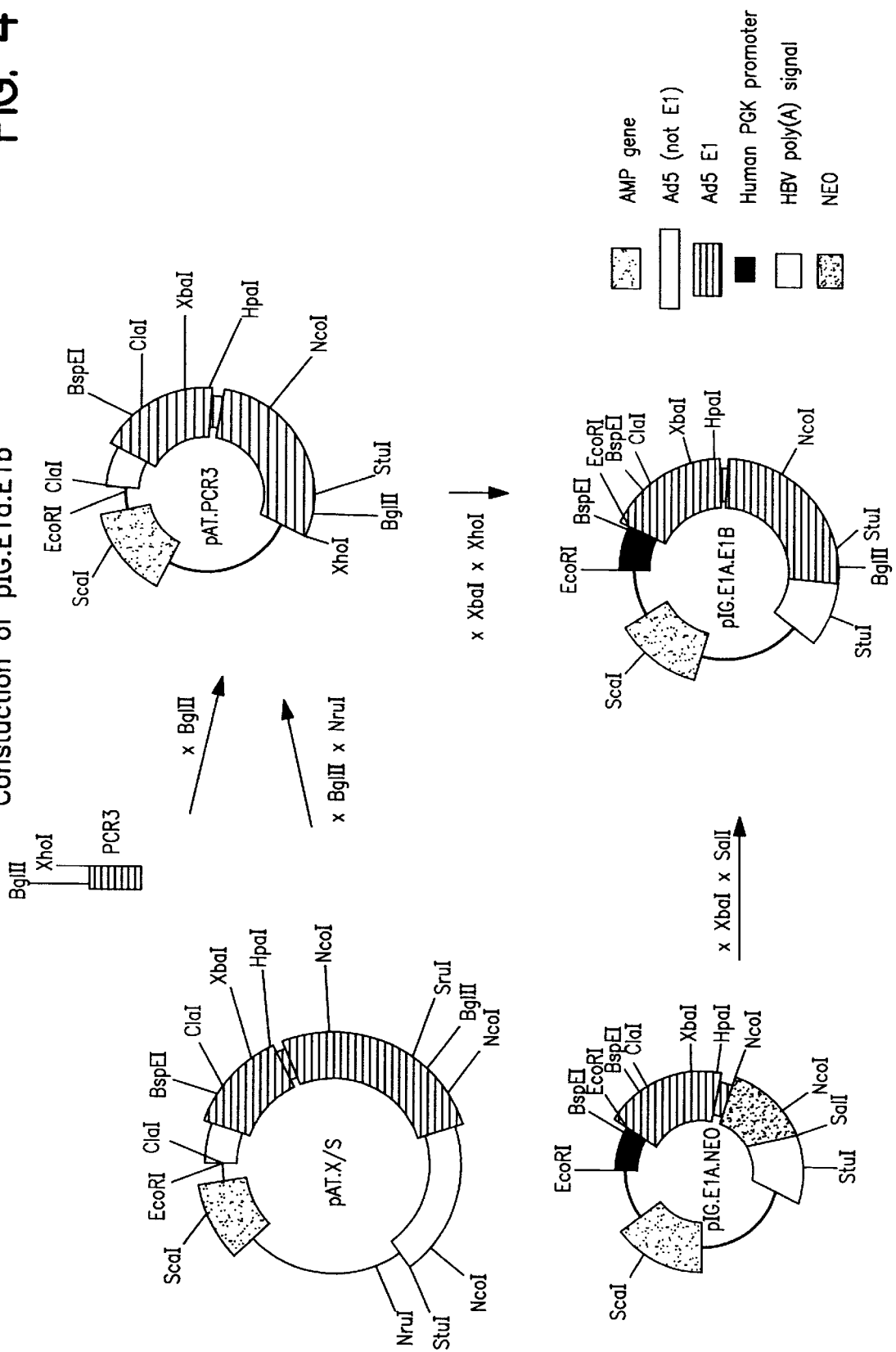
FIG. 4: Construction of pIG.E1A.E1B. pIG.E1A.E1B contains the Ad5 nucleotides 459–3510 (E1A and E1B proteins) operatively linked to the PGK promoter and HBV poly(A) signal. This plasmid was constructed by PCR amplification of the N-terminal amino acids of the E1B 55 kD protein with primers Eb-1 (SEQ ID NO:31) and Eb-2 (SEQ ID NO:32), which introduces an Xho I site, digested with Bgl II and cloned into the Bgl II-Nru I sites of pAT-X/S, producing pAT-PCR3. The Xba I-Xho I fragment of pAT-PCR3 was replaced with the Xba I-Sal I fragment (containing the HBV poly(A) site) of pIG.E1A.NEO to produce pIG.E1A.E1B.

Construction of pIG.E1A.E1B (FIG. 4)

pIG.E1A.E1B contains nt.459 to nt.3510 of Ad5, that encode the E1A and E1B proteins. The E1B sequences are terminated at the splice acceptor at nt.3511. No pIX sequences are present in this construct.

pIG.E1A.E1B was made as follows: The sequences encoding the N-terminal amino acids of E1B 55kd were amplified using primers Eb1 (SEQ ID NO:31) and Eb2 (SEQ ID NO:32) which introduces a XhoI site. The resulting PCR fragment was digested with BglII and cloned into BlII/NruI of pAT-X/S, thereby obtaining pAT-PCR3. The HBV poly (A) sequences of pIG.E1A.NEO were introduced downstream of the E1B sequences of pAT-PCR3 by exchange of the Xba-SalI fragment of pIG.E1A.NEO and the XbaI XhoI fragment of pAT.PCR3.

Figure 5:
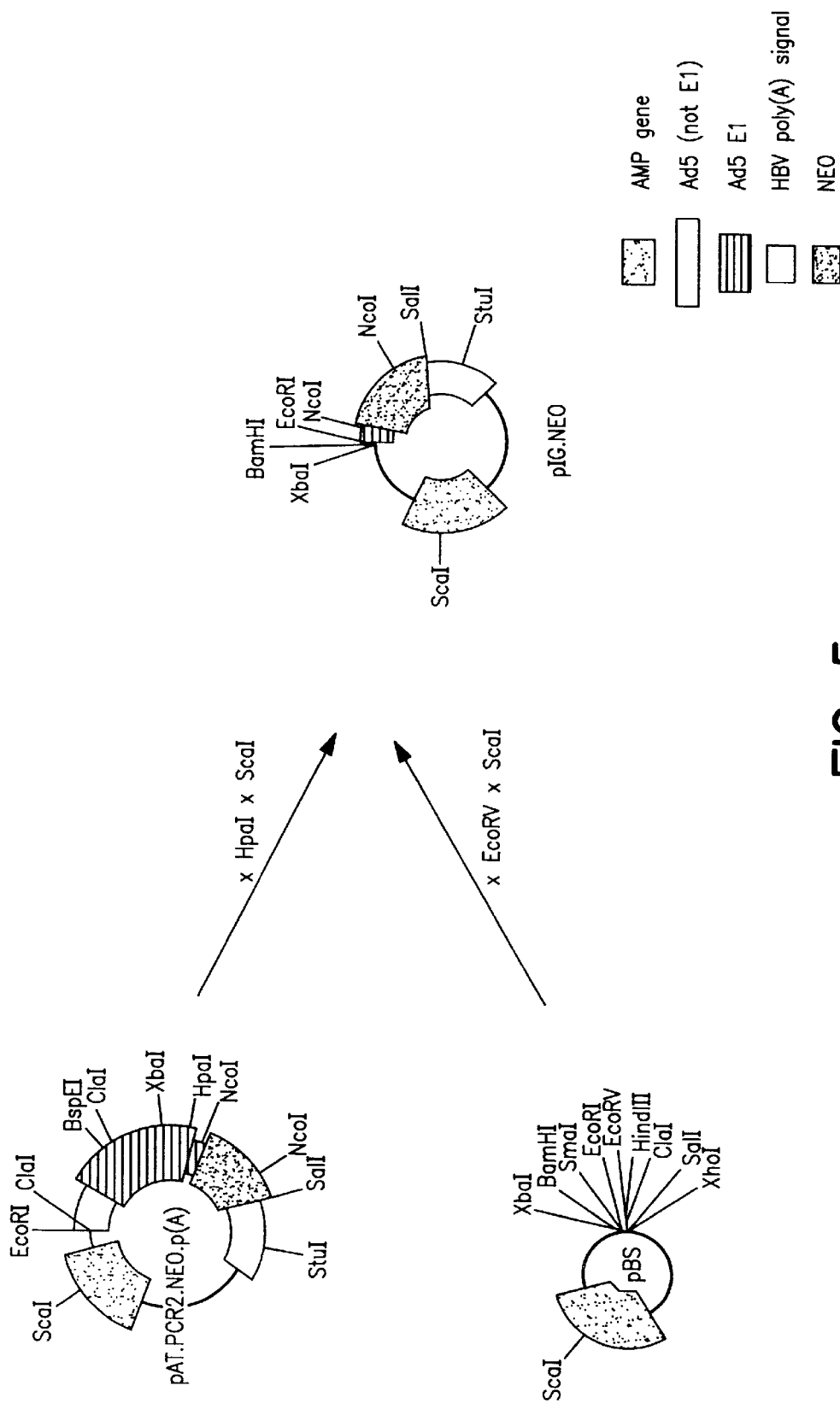
FIG. 5: Construction of pIG.NEO. pIG.NEO contains the Neo$^R$ operatively linked to the E1B promoter. pIG.NEO was constructed by ligating the Hpa I-Sca I fragment of pAT.PCR2.NEO.p(A) or pIG.E1A.NEO which contains the E1B promoter and Neo$^R$ into the EcoR V-Sca I sites of pBS.

Construction of pIG.NEO (FIG. 5)

This construct is of use when established cells are transfected with E1A.E1B constructs and NEO selection is required. Because NEO expression is directed by the E1B promoter, NEO resistant cells are expected to co-express. E1A, which also is advantageous for maintaining high levels of expression of E1A during long-term culture of the cells. pIG.NEO was generated by cloning the HpaI-ScaI fragment of pAT.PCR2.NEO.p(A) or pIG.EIA.NEO, containing the NEO gene under the control of the Ad5 E1B promoter, into pBS digested with EcoRV and ScaI.

Testing of Constructs

The integrity of the constructs pIG.E1A.NEO, pIG.E1A.E1B.X and pIG.E1A.E1B was assessed by restriction enzyme mapping; furthermore, parts of the constructs that were obtained by PCR analysis were confirmed by sequence analysis. No changes in the nucleotide sequence were found.

The constructs were transfected into primary BRK (Baby Rat Kidney) cells and tested for their ability to immortalize (pIG.E1A.NEO) or fully transform (pAd5.XhoIC, pIG.E1A.E1B.X and pIG.E1A.E1B) these cells. Kidneys of 6-day old WAG-Rij rats were isolated, homogenized and trypsinized. Subconfluent dishes (diameter 5 cm) of the BRK cell cultures were transfected with 1 or 5 lg of pIG.NEO, pIG.E1A.NEO, pIG. E1A.E1B, pIG/E1A.E1B.X, pAd5XhiIC, or with pIG.E1A.NEO together with PDC26 (Elsen et al, (1983) Virology 128:377–390), carrying the Ad5.E1B gene under control of the SV40 early promoter. Three weeks post-transfection, when foci were visible, the dishes were fixed, Giemsa stained and the foci counted.

Figure 6:
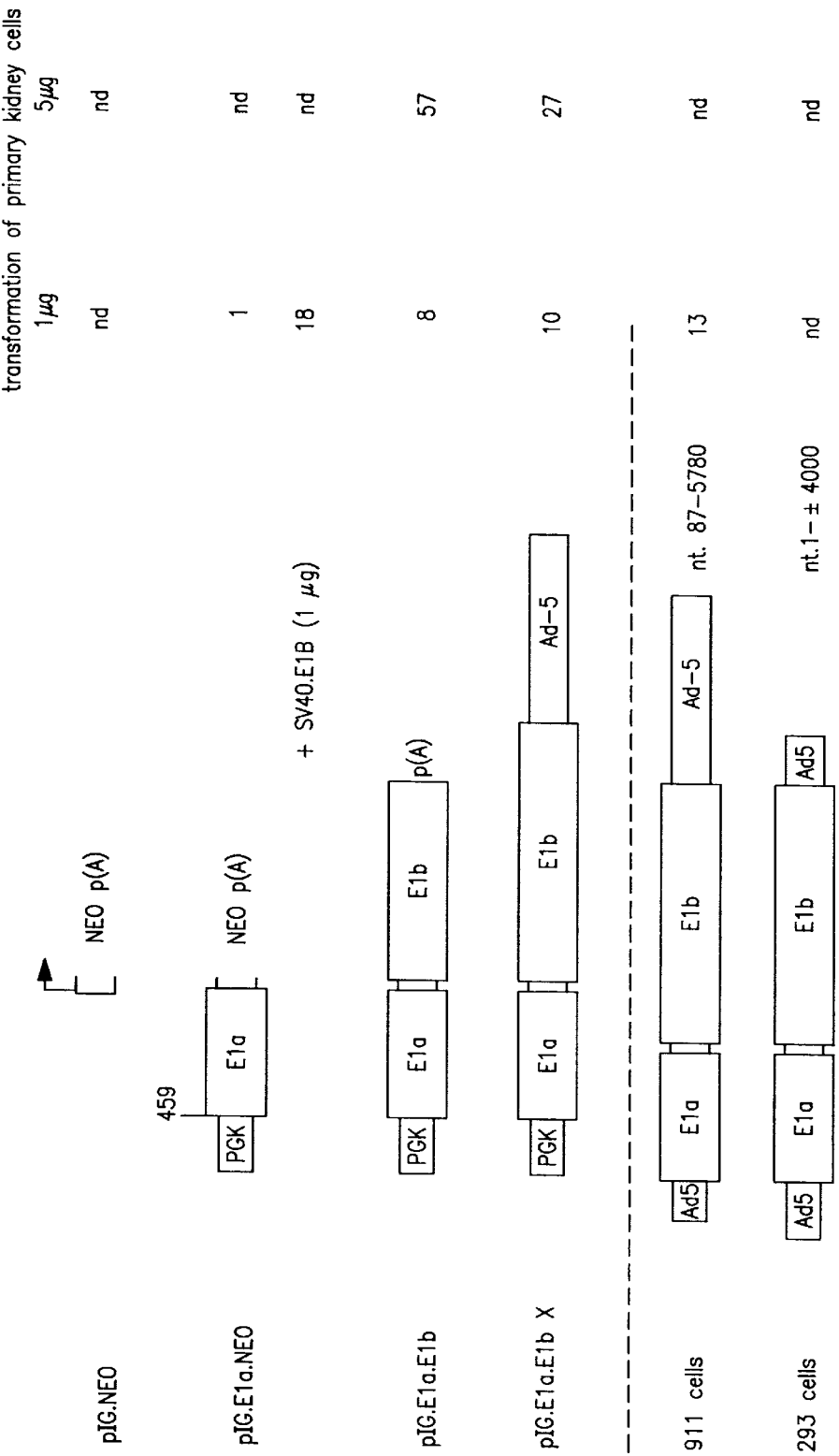
FIG. 6: Transformation of primary baby rat kidney (BRK) cells by adenovirus packaging constructs. Subconfluent dishes of BRK cells were transfected with 1 or 5 µg of either pIG.NEO, pIG.E1A.NEO, pIG.E1A.E1B, pIG.E1A.E1B.X, pAd5XhoIC, or pIG.E1A.NEO plus pDC26, which expresses the Ad5 E1B gene under control of the SV40 early promoter. Three weeks post-transfection, foci were visible, cells were fixed, Giemsa stained and the foci counted. The results shown are the average number of foci per 5 replicate dishes.

An overview of the generated adenovirus packaging constructs, and their ability to transform BRK, is presented in FIG. 6. The results indicate that the constructs pIG.E1A.E1B and pIG.E1A.E1B.X are able to transform BRK cells in a dose-dependent manner. The efficiency of transformation is similar for both constructs and is comparable to what was found with the construct that was used to make 911 cells, namely pAd5.XhoIC.

As expected, pIG.E1A.NEO was hardly able to immortalize BRK. However, co-transfection of an E1B expression construct (PDC26) did result in a significant increase of the number of transformants (18 versus 1), indicating that the E1A encoded by pIG.E1A.NEO is functional. We conclude therefore, that the newly generated packaging constructs are suitable for the generation of new adenovirus packaging lines.

Generation of Cell Lines with New Packaging Constructs
Cell Lines and Cell Culture Human A549 bronchial carcinoma cells (Shapiro et al, (1978) Biochem. Biophys.Acta 530:197–207), human embryonic retinoblasts (HER), Ad5-E1-transformed human embryonic kidney (HEK) cells (293; Graham et al, (1977) J. Gen. Virol. 36: 59–72) and Ad5-transformed HER cells (911; Fallaux et al, (1996). Hum. Gene Ther. 7: 215–222) and PER cells were grown in Dulbecco's Modified Eagle Medium (DMEM) supplemented with 10% Fetal Calf Serum (FCS) and antibiotics in a 5% CO2 atmosphere at 37° C. Cell culture media, reagents and sera were purchased from Gibco Laboratories (Grand Island, N.Y.). Culture plastics were purchased from Greiner (Nuirtingen, Germany) and Corning (Corning, N.Y.).

Viruses and Virus Techniques

The construction of recombinant adenoviral vectors IG.Ad.MLP.nls.lacZ, IG.Ad.MLP.luc, IG.Ad.MLP.TK and IG.Ad.CMV.TK is described in detail in patent application EP 95202213. The recombinant adenoviral vector IG.Ad. MLP.nls.lacZ contains the E. coli lazZ gene, encoding p-galactosidase, under control of the Ad2 major late promoter (MLP), IG.Ad.MLP.luc contains the firefly luciferase gene drive by the Ad2 MLP, and adenoviral vectors IG.Ad. MLP.TK and IG.Ad.CMV.TK contain the Herpes Simplex Virus thymidine kinase (TK) gene under the control of the Ad2 MLP and the Cytomegalovirus (CMV) enhancer/promoter, respectively.

Transfections

All transfections were performed by calcium-phosphate precipitation DNA (Graham et al, (1973) Virology 52: 456–467) with the GIBCO Calcium Phosphate Transfection System (GIBCO BRL Life Technologies, Inc., Gaithersburg, USA), according to the manufacturer's protocol.

Western blotting

Subconfluent cultures of exponentially growing 293, 911 and Ad5-E1-transformed A549 and PER cells were washed with PBS and scraped in Fos-RIPA buffer (10 mM Tris (pH 7,5), 150 mM NaCl, 1% NP40,01 % sodium dodecyl sulfate (SDS), 1% NA-DOC, 0,5 mM phenyl methyl sulfonyl fluoride (PMSF), 0,5 mM trypsin inhibitor, 50 mM NaF and 1 mM sodium vanadate). After 10 min. at room temperature, lysates were cleared by centrifugation. Protein concentrations were measured with the BioRad protein assay kit, and 25 $\mu$g total cellular protein was loaded on a 12.5% SDS-PAA gel. After electrophoresis, proteins were transferred to nitrocellulose (1 h at 300 mA). Prestained standards (Sigma, USA) were run in parallel. Filters were blocked with 1 % bovine serum albumin (BSA) in TBST (10 mM Tris, pH 8, 15 mM NaCl, and 0.05% Tween-20) for 1 hour. First antibodies were the mouse monoclonal anti-Ad5-E1B-55-kDA antibody A1C6 (Zantema et al, unpublished), the rat monoclonal anti-Ad5-E1B-221 -kDa antibody C1G11 (Zantema et al, (1985) Virology 142:44–58). The second antibody was a horseradish peroxidase-labeled goat anti-mouse antibody (Promega). Signals were visualized by enhanced chemoluminescence (Amersham Corp. UK).

Southern Blot Analysis

High molecular weight DNA was isolated and 10 $\mu$g was digested to completion and fractionated on a 0.7% agarose gel. Southern blot transfer to Hybond N+ (Amersham, UK)

was performed with a 0.4 M NAOH, 0.6 M NaCl transfer solution (Church and Gilbert, 1984). Hybridization was performed with a 2463-nt SspI-HindIII fragment from pAd5.SalB (Bernards et al, (1983) *Virology* 127:45–53). This fragment consists of Ad5 bp. 342–2805. The fragment was radiolabeled with $\alpha^{-32p}$=dCTP with the use of random hexanucleotide primers and Kelnow DNA polymerase. The southern blots were exposed to a Kodak XAR-5 film at –80° C. and to a Phospho-Imager screen which was analyzed by B&L systems Molecular Dynamics Software.

A549

AdS-E1-transformed A549 human bronchial carcinoma cell lines were generated by transfection with pIG.E1A.NEO and selection for G418 resistance. Thirty-one G418 resistant clones were established. Co-transfection of pIG.E1A.E1B with pIG.NEO yielded seven G418 resistant cell lines.

PER

Ad5-E1-transformed human embryonic retina (HER) cells were generated by transfection of primary HER cells with plasmid pIG.E1A.E1B. Transformed cell lines were established from well-separated foci. We were able to establish seven clonal cell lines, which we called PER.Cl, PER.C3, PER.C4, PER.C5, PER.C6, PER.C8 and PER. C9. One of the PER clones, namely PER. C6, has been deposited at the ECACC under number 96022940.

Expression of Ad5 E1A and E1B Genes in Transformed A549 and PER Cells

Figure 7:
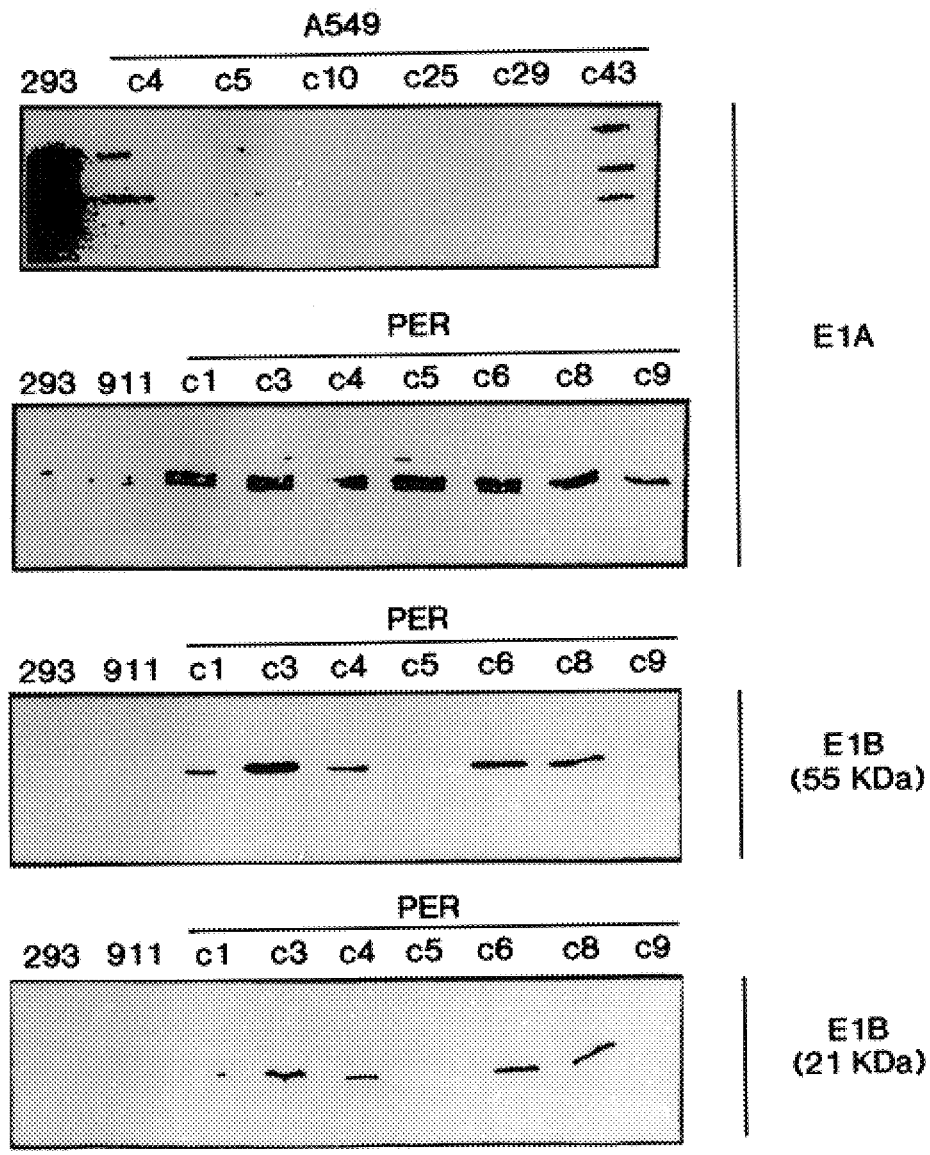
FIG. 7: Western blot analysis of A549 clones transfected with pIG.E1A.NEO and human embryonic retinoblasts (HER cells) transfected with pIG.E1A.E1B (PER clones). Expression of Ad5 E1A and E1B 55 kD and 21 kD proteins in transfected A549 cells and PER cells was determined by Western blot with mouse monoclonal antibodies (Mab) M73 which recognizes E1A gene products and Mabs AIC6 and C1G11, which recognize the E1B 55 kDa and 21 kDa proteins, respectively. Mab binding was visualized using horseradish peroxidase-labeled goat anti-mouse antibody and enhanced chemiluminesence. 293 and 911 cells served as controls.

Expression of the Ad5 E1A and the 55-kDa and 21 kDa E1B proteins in the established A549 and PER cells was studied by means of Western blotting, with the use of monoclonal antibodies (mAb). mAb M73 recognizes the E1A products, whereas Mabs AIC6 and C1G11 are directed against the 55-kDa and 21 kDa E1B proteins, respectively. The antibodies did not recognize proteins in extracts from the parental A549 or the primary HER cells (data not shown). None of the A549 clones that were generated by co-transfection of pIG.NEO and pIG.E1A.E1B expressed detectable levels of E1A or E1B proteins (not shown). Some of the A549 clones that were generated by transfection with pIG.E1A.NEO expressed the Ad5 E1A proteins (FIG. 7), but the levels were much lower than those detected in protein lysates from 293 cells. The steady state E1A levels detected in protein extracts from PER cells were much higher than those detected in extracts from A549-derived cells. All PER cell lines expressed similar levels of E1A proteins (FIG. 7). The expression of the E1B proteins, particularly in the case of E1B 55 kDa, was more variable. Compared to 911 and 293, the majority of the PER clones express high levels of E1B 55 kDa and 2 kDa. The steady state level of E1B 21 kDa was the highest in PER.C3. None of the PER clones lost expression of the Ad5 E1 genes upon serial passage of the cells (not shown). We found that the level of E1 expression in PER cells remained stable for at least 100 population doublings. We decided to characterize the PER clones in more detail.

Southern Analysis of PER Clones

Figure 8:
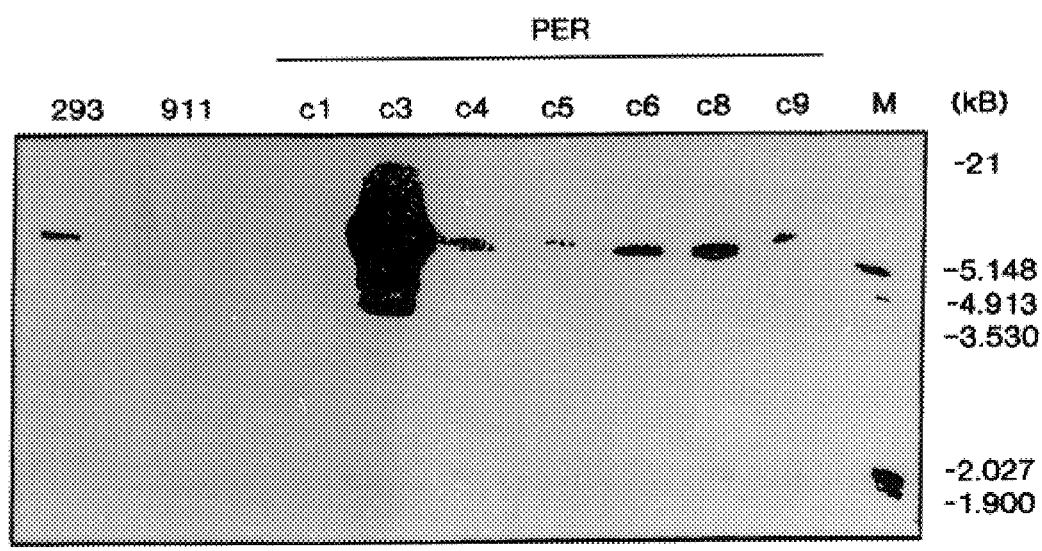
FIG. 8: Southern blot analysis of 293, 911 and PER cell lines. Cellular DNA was extracted, Hind III digested, electrophoresed and transferred to Hybond N+ membranes (Amersham). Membranes were hybridized to radiolabeled probes generated by random priming of the Ssp I-Hind III fragment of pAd5.SalB (Ad5 nucleotides 342–2805).

To study the arrangement of the Ad5-E1 encoding sequences in the PER clones we performed Southern analyses. Cellular DNA was extracted from all PER clones, and from 293 and 911 cells. The DNA was digested with HindIII, which cuts once in the Ad5 E1 region. Southern hybridization on HindIll-digested DNA, using a radiolabeled Ad5-E1-specific probe revealed the presence of several integrated copies of pIG.E1A.E1B in the genome of the PER clones. FIG. 8 shows the distribution pattern of E1 sequences in the high molecular weight DNA of the different PER cell lines. The copies are concentrated in a single band, which suggests that they are integrated as tandem repeats. In the case of PER.C3, C5, C6 and C9 we found additional hybridizing bands of low molecular weight that indicate the presence of truncated copies of pIG.E1A.E1B. The number of copies was determined with the use of a Phospho-Imager. We estimated that PER.C1, C3, C4, C5, C6, C8 and C9 contain 2, 88, 5, 4, 5, 5, and 3 copies of the Ad5 E1 coding region, respectively, and that 911 and 293 cells contain 1 and 4 copies of the Ad5 E1 sequences, respectively.

Transfection Efficiency

Figure 9:
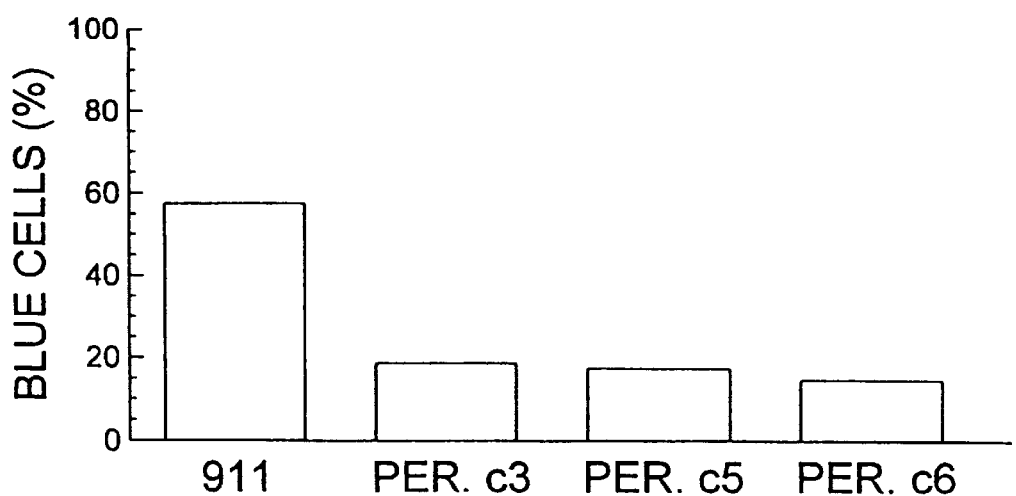
FIG. 9: Transfection efficiency of PER.C3, PER.C5, PER.C6 and 911 cells.

Recombinant adenovectors are generated by co-transfection of adaptor plasmids and the large ClaI fragment of Ad5 into 293 cells (EP application 95202213). The recombinant virus DNA is formed by homologous recombination between the homologous viral sequences that are present in the plasmid and the adenovirus DNA. The efficacy of this method, as well as that of alternative strategies, is highly dependent on the transfectability of the helper cells. Therefore, we compared the transfection efficiencies of some of the PER clones with 911 cells, using the *E. coli* β-galactosidase-encoding lacZ gene as a reporter (FIG. 9).

Production of Recombinant Adenovirus

Yields of recombinant adenovirus obtained after inoculation of 293, 911, PER. C3, PER.C5 and PER.C6 with different adenovirus vectors are presented in Table II.

The results indicate that the recombinant adenovirus vector yields obtained with PER cells are at least as high as those obtained with the existing cell lines. In addition, the yields of the novel adenovirus vector IG.Ad.MLPI.TK are similar or higher than the yields obtained for the other viral vectors on all cell lines tested.

Generation of New Adenovirus Vectors (FIG. 10)

The recombinant adenovirus vectors used (see patent application EP 95202213) are deleted for E1 sequences from 459 to nt. 3328. As construct pE1A.E1B contains AdS sequences 459 to nt. 3510 there is a sequence overlap of 183 nt. between E1B sequences in the packaging construct pIG.E1A.E1B and recombinant adenoviruses, such as for example IG.Ad.MLP.TK. The overlapping sequences were deleted from the new adenovirus vectors. In addition, non-coding sequences derived from lacZ, that are present in the original constructs, were deleted as well. This was achieved (see FIG. 10) by PCR amplification of the SV40 poly (A) sequences from pMLP.TK using primers SV40-1 (SEQ ID NO: 33) (introduces a BamHI site) and SV40-2 (SEQ ID NO: 34) (introduces a BglII site). In addition, Ad5 sequences present in this construct were amplified from nt. 2496 (Ad5, introduces a BglII site) to nt. 2779 (Ad5-2). Both PCR fragments were digested with BglII and were ligated. The ligation product was PCR amplified using primers SV40-1 and Ad5-2 (SEQ ID NO:36). The PCR product obtained was cut with BamHI and AflII and was ligated into pMLP.TK predigested with the same enzymes. The resulting construct, named pMLPI.TK, contains a deletion in adenovirus E1 sequences from nt. 459 to nt. 3510.

Packaging System

The combination of the new packaging construct pIG.E1A.E1B and the recombinant

TABLE II

Production of recombinant adenoviral vector
or different packages, cell lines.

| | | Yields × $10^{-8}$ pfu/T175 flask.[1] | | | | |
|---|---|---|---|---|---|---|
| Cell | Passage Number | IG.Ad.CMV.lacZ | IG.Ad.CMV.TK | IG.Ad.MLPI.TK | d1313 | Producer Mean |
| 293 | | 6.0 | 5.8 | 24 | 34 | 17.5 |
| 911 | | 8 | 14 | 34 | 180 | 59.5 |
| PER.C3 | 17 | 8 | 11 | 44 | 40 | 25.8 |
| PER.C5 | 15 | 6 | 17 | 36 | 200 | 64.7 |
| PER C6 | 36 | 10 | 22 | 58 | 320 | 102 |

[1]The yields are the mean of two different experiments. IG.Ad.CMV.lacZ and IG.Ad.CMV.TK are described in patent application EP 95 20 2213. The construction of IG.Ad.MLPI.TK is described in this patent application. Yields of virus per T80 flask were determined by plaque assay on 911 cells, as described (Fallaux et al (1996) Hum. Gene Ther. 7: 215–222). #1493).

adenovirus pMLPI.TK, which do not have any sequence overlap, are presented in FIG. 11. In this figure, also the original situation is presented, where the sequence overlap is indicated. The absence of overlapping sequences between pIG.E1A.E1B and pMLPI.TK (FIG. 11a) excludes the possibility of homologous recombination between the packaging construct and the recombinant virus, and is therefore a significant improvement for production of recombinant adenovirus as compared to the original situation.

In FIG. 11b the situation is depicted for pIG.E1A.NEO and IG.Ad.MLPI.TK. pIG.E1A.NEO when transfected into established cells, is expected to be sufficient to support propagation of E1-deleted recombinant adenovirus. This combination does not have any sequence overlap, preventing generation of RCA by homologous recombination. In addition, this convenient packaging system allows the propagation of recombinant adenoviruses that are deleted just for E1A sequences and not for E1B sequences.

Recombinant adenoviruses expressing E1B in the absence of E1A are attractive, as the E1B protein, in particular E1B 19 kD, is able to prevent infected human cells from lysis by Tumor Necrosis Factor (TNF) Gooding et al, (1991) *J. Virol.* 65: 3083–3094).

Generation of Recombinant Adenovirus Derived from pMLPI.TK

Recombinant adenovirus was generated by co-transfection of 293 cells with SalI linearized pMLPI.TK DNA and ClaI linearized Ad5 wt DNA. The procedure is schematically represented in FIG. 12.

Example 2

Plasmid-based System for Rapid RCA-free Generation of Recombinant Adenoviral Vectors Construction of Adenovirus Clones pBr/Ad.Bam-rITR (ECACC deposit P97082122)

In order to facilitate blunt end cloning of the ITR sequences, wild-type human adenovirus type 5 (Ad5) DNA was treated with Klenow enzyme in the presence of excess dNTPs. After inactivation of the Klenow enzyme and purification by phenol/chloroform extraction followed by ethanol precipitation, the DNA was digested with BamHI. This DNA preparation was used without further purification in a ligation reaction with pBr322 derived vector DNA prepared as follows: pBr322 DNA was digested with EcoRV and BamHI, dephosphorylated by treatment with TSAP enzyme (Life Technologies) and purified on LMP agarose gel (SeaPlaque GTG). After transformation into competent *E. coli* DH5α (Life Techn.) and analysis of ampicillin resistant colonies, one clone was selected that showed a digestion pattern as expected for an insert extending from the BamHI site in Ad5 to the right ITR. Sequence analysis of the cloning border at the right ITR revealed that the most 3' G residue of the ITR was missing, the remainder of the ITR was found to be correct. Said missing G residue is complemented by the other ITR during replication.

pBr/Ad.Sal-rITR (ECACC deposit P97082119)

pBr/Ad.Bam-rITR was digested with BamHl and SalI. The vector fragment including the adenovirus insert was isolated in LMP agarose (SeaPlaque GTG) and ligated to a 4.8 kb SalI-BamHI fragment obtained from wt Ad5 DNA and purified with the Geneclean II kit (Bio 101, Inc.). One clone was chosen and the integrity of the Ad5 sequences was determined by restriction enzyme analysis. Clone pBr/Ad.Sal-rITR contains adeno type 5 sequences from the SalI site at bp 16746 up to and including the rITR (missing the most 3' G residue).

pBr/Ad.Cla-Bam (ECACC deposit P97082117)

wt Adeno type 5 DNA was digested with ClaI and BamHI, and the 20.6 kb fragment was isolated from gel by electroelution. pBr322 was digested with the same enzymes and purified from agarose gel by Geneclean. Both fragments were ligated and transformed into competent DH5α. The resulting clone pBr/Ad.Cla-Bam was analyzed by restriction enzyme digestion and shown to contain an insert with adenovirus sequences from bp 919 to 21566.

pBr/Ad.AflII-Bam (ECACC deposit P97082114)

Clone pBr/Ad.Cla-Bam was linearized with EcoRi (in pBr322) and partially digested with AflIII. After heat inactivation of AflII for 20 minutes at 65° C., the fragment ends were filled in with Klenow enzyme. The DNA was then ligated to a blunt double stranded oligo linker containing a PacI site (5'-AATTGTCTTAATTAACCGCTTAA-3') (SEQ ID NO: 1). This linker was made by annealing the following two oligonucleotides: 5'-AATTGTCTTAATTAACCGC-3' (SEQ ID NO:2) and 5'-AATTGCGGTTAATTAAGAC-3' (SEQ ID NO:3), followed by blunting with Kienow enzyme. After precipitation of the ligated DNA to change buffer, the ligations were digested with an excess PacI enzyme to remove concatameres of the oligo. The 22016 bp partial fragment containing Ad5 sequences from bp 3534 up to 21566 and the vector sequences, was isolated in LMP agarose (SeaPlaque GTG), religated and transformed into competent DH5α. One clone that was found to contain the PacI site and that had retained the large adeno fragment was selected and sequenced at the 5' end to verify correct insertion of the PacI linker in the (lost) AflII site.

pBr/Ad.Bam-rlTRpac#2 (ECACC deposit P97082120) and pBr/Ad.Bam-rITR#8 (ECACC deposit P97082121)

To allow insertion of a PacI site near the ITR of Ad5 in clone pBr.Ad.Bam-rITR about 190 nucleotides were removed between the ClaI site in the pBr322 backbone and the start of the ITR sequences. This was done as follows: pBr/Ad.Bam-rITR was digested with ClaI and treated with nuclease Bal31 for varying lengths of time (2', 5', 10' and 15'). The extent of nucleotide removal was followed by separate reactions on pBr322 DNA (also digested at the ClaI site), using identical buffers and conditions. Bal31 enzyme was inactivated by incubation at 75° C. for 10 minutes, the DNA was precipitated and resuspended in a smaller volume TE buffer. To ensure blunt ends, DNAs were further treated with T4 DNA polymerase in the presence of excess dNTPs. After digestion of the (control) pBr322 DNA with SaiI, satisfactory degradation (~150 bp) was observed in the samples treated for 10 minutes or 15 minutes. The 10 minutes or 15 minutes treated pBr/Ad.Bam-rITR samples were then ligated to the above described blunted PacI linkers (see pBr/Ad.AflII-Bam). Ligations were purified by precipitation, digested with excess PacI and separated from the linkers on an LMP agarose gel. After relegation, DNAs were transformed into competent DH5α and colonies analyzed. Ten clones were selected that showed a deletion of approximately the desired length and these were further analyzed by T-track sequencing (T7 sequencing kit, Pharmacia Biotech). Two clones were found with the PacI linker inserted just downstream of the rITR. After digestion with PacI, clone #2 has 28 bp and clone #8 has 27 bp attached to the ITR.

pWE/Ad.AflII-rITR (ECACC deposit P97082116)

Cosmid vector pWE15 (Clontech) was used to clone larger Ad5 inserts. First, a linker containing a unique PacI site was inserted in the EcoRI sites of pWE15 creating pWE.pac. To this end, the double stranded PacI oligo as described for pBr/Ad.AflII-BamHI was used but now with its EcoRI protruding ends. The following fragments were then isolated by electro-elution from agarose gel: pWE.pac digested with PacI, pBr/AflII-Bam digested with PacI and BamHI and pBr/Ad.Bam-rITR#2 digested with BamHI and PacI. These fragments were ligated together and packaged using λ phage packaging extracts (Stratagene) according to the manufacturer's protocol. After infection into host bacteria, colonies were grown on plates and analyzed for presence of the complete insert. pWE/Ad.AflII-rITR contains all adenovirus type 5 sequences from bp 3534 (AflII site) up to and including the right ITR (missing the most 3' G residue).

Adeno 5 wt DNA was treated with Klenow enzyme in the presence of excess dNTPs and subsequently digested with SaiI. Two of the resulting fragments, designated left ITR-Sal(9.4) and Sal(16.7)-right ITR, respectively, were isolated in LMP agarose (Seaplaque GTG). pBr322 DNA was digested with EcoRV and SalI and treated with phosphatase (Life Technologies). The vector fragment was isolated using the Geneclean method (BIO 101, Inc.) and ligated to the Ad5 SalI fragments. Only the ligation with the 9.4 kb fragment gave colonies with an insert. After analysis and sequencing of the cloning border a clone was chosen that contained the full ITR sequence and extended to the SalI site at bp 9462.

pBr/Ad.lITR-Sal(16.7) (ECACC deposit P97082118)

pBr/Ad.lITR-Sal(9.4) is digested with SalI and dephosphorylated (TSAP, Life Technologies). To extend this clone up to the third SalIsite in Ad5, pBr/Ad.Cla-Bam was linearized with BamHI and partially digested with SalI. A 7.3 kb SalI fragment containing adenovirus sequences from 9462–16746 was isolated in LMP agarose gel and ligated to the SalI-digested pBr/Ad.lITR-Sal(9.4) vector fragment.

pWE/Ad.Afl-EcoRI pWE.pac was digested with ClaI and the 5' protruding ends were filled in using Klenow enzyme. The DNA was then digested with PacI and isolated from agarose gel. pWE/AflII-rITR was digested with EcoRI and after treatment with Klenow enzyme digested with PacI. The large 24 kb fragment containing the adenoviral sequences was isolated from agarose gel and ligated to the ClaI-digested and blunted pWE.pac vector using the Ligation Express™ kit from Clontech. After transformation of Ultracompetent XL10-Gold cells from Stratagene, clones were identified that contained the expected insert. pWE/AflII-EcoRI contains Ad5 sequences from bp 3534–27336.

Construction of New Adapter Plasmids

The absence of sequence overlap between the recombinant adenovirus and E1 sequences in the packaging cell line is essential for safe, RCA-free generation and propagation of new recombinant viruses. The adapter plasmid pMLPI.TK (FIG. 10) is an example of an adapter plasmid designed for use according to the invention in combination with the improved packaging cell lines of the invention. This plasmid was used as the starting material to make a new vector in which nucleic acid molecules comprising specific promoter and gene sequences can be easily exchanged.

First, a PCR fragment was generated from pZipΔMo+ PyF101(N⁻) template DNA (described in PCT/NL96/00195) with the following primers: LTR-1: 5'-CTG TAC GTA CCA GTG CAC TGG CCT AGG CAT GGA AAA ATA CAT AAC TG-3' (SEQ ID NO:4) and LTR-2: 5'-GCG GAT CCT TCG AAC CAT GGT AAG CTT GGT ACC GCT AGC GTT AAC CGG GCG ACT CAG TCA ATC G-3' (SEQ ID NO:5). Pwo DNA polymerase (Boehringer Mannheim) was used according to the manufacturer's protocol with the following temperature cycles: once 5 minutes at 95° C.; 3 minutes at 55° C.; and 1 minute at 72° C., and 30 cycles of 1 minute at 95° C., 1 minute at 60° C., 1 minute at 72° C., followed by once 10 minutes at 72° C. The PCR product was then digested with BamHI and ligated into a pMLP10 (Levrero et al, (1991) *Gene* 101:195–202) vector digested with PvuII and BamHI, thereby generating vector pLTR10. This vector contains adenoviral sequences from bp 1 up to bp 454 followed by a promoter which includes part of the Mo-MuLV LTR in which the wild-type enhancer sequences are replaced by the enhancer from a mutant polyoma virus (PyF101). The promoter fragment was designated L420.

Next, the coding region of the murine HSA gene was inserted. pLTR10 was digested with BstBI followed by Klenow treatment and digestion with NcoI. The HSA gene was obtained by PCR amplification on pUC18-HSA (Kay et al, (1990) *J. Immunol.* 145:1952–1959) using the following primers: HSA1, 5'-GCG CCA CCA TGG GCA GAG CGA TGG TGG C-3' (SEQ ID NO:6) and HSA2, 5'-GTT AGA TCT AAG CTT GTC GAC ATC GAT CTA CTA ACA GTA GAG ATG TAG AA-3' (SEQ ID NO:7). The 269 bp amplified fragment was subcloned in a shuttle vector using the NcoI and BglII sites. Sequencing confirmed incorporation of the correct coding sequence of the HSA gene, but with an extra TAG insertion directly following the TAG stop codon. The coding region of the HSA gene, including the TAG duplication was then excised as a NcoI(sticky)-SalI(blunt) fragment and cloned into the 3.5 kb NcoI(sticky)/BstBI (blunt) fragment from pLTR10, resulting in pLTR-HSA10.

Finally, pLTR-HSA10 was digested with EcoRI and BamHI after which the fragment containing the left ITR, packaging signal, L420 promoter and HSA gene was inserted into vector pMLPI.TK digested with the same enzymes, thereby replacing the promoter and the gene sequences. This resulted in the new adapter plasmid pAd/L420-HSA (FIG. 19) that contains convenient recognition sites for various restriction enzymes around the promoter and gene sequences. SnaBI and AvrII can be combined with HpaI, NheI, KpnI, HindIII to exchange promoter sequences, while the latter sites can be combined with the ClaI or BamHI sites 3' from the HSA coding region to replace genes in this construct.

Another adapter plasmid that was designed to allow easy exchange of nucleic acid molecules was made by replacing the promoter, gene and poly A sequences in pAd/L420-HSA with the CMV promoter, a multiple cloning site, an intron and a poly-A signal. For this purpose, pAd/L420-HSA was digested with AvrII and BglII, followed by treatment with Klenow to obtain blunt ends. The 5.1 kb fragment with pBr322 vector and adenoviral sequences was isolated and ligated to a blunt 1570 bp fragment from pcDNA1/amp (Invitrogen) obtained by digestion with HhaI and AvrII followed by treatment with T4 DNA polymerase. This adapter plasmid was named pCLIP (FIG. 20).

Generation of Recombinant Adenoviruses

E1-deleted Recombinant Adenoviruses with wt E3 Sequences

To generate E1 deleted recombinant adenoviruses with the new plasmid-based system, the following constructs were prepared: an adapter construct containing the expression cassette with the gene of interest linearized with a restriction enzyme that cuts at the 3' side of the overlapping adenoviral genome fragment, preferably not containing any pBr322 vector sequences; and a complementing adenoviral genome construct pWE/Ad.AflII-rITR digested with PacI.

These two DNA molecules are further purified by phenol/chloroform extraction and EtOH precipitation. Co-transfection of these plasmids into an adenovirus packaging cell line, preferably a cell line according to the invention, generates recombinant replication deficient adenoviruses by a one-step homologous recombination between the adapter and the complementing construct (FIG. 21). Alternatively, instead of pWE/Ad.AflII-rITR other fragments can be used, e.g., pBr/Ad.Cla-Bam digested with EcoRI and BamHI or pBr/Ad.AflII-BamHII digested with PacI and BamHI can be combined with pBr/Ad.Sal-rITR digested with SalI. In this case, three plasmids are combined and two homologous recombinations are needed to obtain a recombinant adenovirus (FIG. 22). It is to be understood that those skilled in the art may use other combinations of adapter and complementing plasmids without departing from the present invention.

A general protocol as outlined below and meant as a non-limiting example of the present invention has been performed to produce several recombinant adenoviruses using various adapter plasmids and the Ad.AflII-rITR fragment. Adenovirus packaging cells (PER.C6) were seeded in ~25 cm$^2$ flasks and the next day when they were at ~80% confluency, were transfected with a mixture of DNA and lipofectamine agent (Life Techn.) as described by the manufacturer. Routinely, 40 µl lipofectamine, 4 µg adapter plasmid and 4 µg of the complementing adenovirus genome fragment AflII-rITR (or 2 µg of all three plasmids for the double homologous recombination) were used. Under these conditions transient transfection efficiencies of ~50% (48 hrs post transfection) were obtained as determined with control transfections using a pAd/CMV-LacZ adapter. Two days later, cells were passaged to ~80 cm$^2$ flasks and further cultured. Approximately five (for the single homologous recombination) to eleven days (for the double homologous recombination) later a cytopathic effect (CPE) was seen, indicating that functional adenovirus has formed. Cells and medium are harvested upon full CPE and recombinant virus is released by freeze-thawing. An extra amplification step in a 80 cm$^2$ flask was routinely performed to increase the yield since at the initial stage the titers was found to be variable despite the occurrence of full CPE. After amplification, viruses was harvested and plaque purified on PER.C6 cells. Individual plaques was tested for viruses with active transgenes.

Four different recombinant adenoviruses, containing the human interleukin-3 gene (see FIG. 1, WO88/04691), the human endothelial nitric oxide gene (Janssens et al, (1992) *J. Biol. Chem.* 267:14519–14522), the Tc1A transposase gene (Vos et al, (1993) *Genes Dev.* 7:1244–1253), or the bacterial LacZ gene (Kalderon et al, (1984) *Cell* 39:499–509, have been produced using this protocol. In all cases, functional adenovirus was formed and all isolated plaques contained viruses with an active transgene.

E1-deleted Recombinant Adenoviruses with Modifications in the E3 or E4 Regions

Besides replacements in the E1 region it is possible to delete the E3 region or replace part of the E3 region in the adenovirus because E3 functions are not necessary for the replication, packaging and infection of a recombinant virus. This creates the opportunity to use a larger insert or to insert more than one gene without exceeding the maximum packagable size (approximately 105% of wt genome length). This can be done, for example, by deleting part of the E3 region in the pBr/Ad.Bam-rITR clone by digestion with XbaI and religation. This removes Ad5 wt sequences 28592–30470 including all known E3 coding regions. Another example is the precise replacement of the coding region of gp19K in the E3 region with a polylinker allowing insertion of new sequences. This leaves all other coding regions intact, obviates the need for a heterologous promoter since the transgene is driven by the E3 promoter and pA sequences, leaving more space for coding sequences and results in very high transgene expression, at least as good as in a control E1 replacement vector.

To this end, the 2.7 kb EcoRI fragment from wt Ad5 containing the 5' part of the E3 region was cloned into the EcoRI site of pBluescript (KS$^-$) (Stratagene). Next, the HindIII site in the polylinker was removed by digestion with EcoRV and HincII and subsequent religation. The resulting clone pBS.Eco-Eco/ad5ΔHIII was used to delete the gp19K coding region. Primers 1 (5'-GGG TAT TAG GCC AAAGGCGCA-3') (SEQ ID NO:8) and 2 (5'-GAT CCC ATG GAA GCT TGG GTG GCG ACC CCA GCG-3') (SEQ ID NO:9) were used to amplify a sequence from pBS.Eco-Eco/ad5ΔHIII corresponding to sequences 28511 to 28734 in wt Ad5 DNA. Primers 3 (5'-GAT CCC ATG GGG ATC CTT TAC TAA GTT ACA AAG CTA-3') (SEQ ID NO: 10) and 4 (5'-GTC GCT GTA GTT GGA CTG G-3') (SEQ ID NO: 11) were used on the same DNA to amplify Ad5 sequences from 29217 to 29476. The two resulting PCR fragments were ligated together by virtue of the newly introduced NcoI site and subsequently digested with XbaI and MunI. This fragment was then ligated into a pBS.Eco-Eco/ad5ΔHIII vector that had been partially digested with XbaI and MunI, generating pBS.Eco-Eco/ad5ΔHIII.Agp19K.

To allow insertion of foreign genes into the HindIII and BamHI site, an XbaI deletion was made in pBS.Eco-Eco/ad5ΔHIII.Agp19K to remove the BamHI sites in the Bluescript polylinker. The resulting plasmid pBS.Eco-Eco/ad5ΔHIIIΔgp19KΔXbaI, contains unique HindIII and BamHI sites corresponding to sequences 28733 (HindIII) and 29218 (BamHI) in Ad5. After introduction of a foreign gene into these sites, either the deleted XbaI fragment is re-introduced, or the insert is recloned into pBS.Eco-Eco/ ad5ΔHIII.Δgp19K using HindIII and, for example MunI. Using this procedure, we have generated plasmids expressing HSV-TK (McKnight (1980) *Nucl. Acid. Res.* 8:5949–5964 and Vincent et al (1996) *Hum. Gene Ther.* 7:197–205), hIL-1α (Esandi et al, (1998) *Gene Therapy* 5:xxx-yyy), rat IL-3β (Esandi et al, (1998) *Gene* 11242:xxx-yyy), luciferase (DeWit et al, (1987) *Mol. Cell Biol.* 7:725–737) or LacZ. The unique SrfI and NotI sites in the pBS.Eco-Eco/ad5ΔHIII.Δgp19K plasmid (with or without an inserted gene of interest) are used to transfer the region containing the gene of interest into the corresponding region of pBr/Ad.Bam-rITR, yielding construct pBr/Ad.Bam-rITRΔgp19K (with or without an inserted gene of interest). This construct is used as described supra to produce recombinant adenoviruses. In the viral context, expression of inserted genes is driven by the adenovirus E3 promoter.

Recombinant viruses that are both E1 and E3 deleted are generated by a double homologous recombination procedure as described above for E1-replacement vectors using a plasmid-based system which includes: an adapter plasmid for E1 replacement according to the invention, with or without insertion of a first gene of interest, the pWE/Ad.AflII-EcoRI fragment, and the pBr/Ad.Bam-rITRΔgp19K plasmid with or without insertion of a second gene of interest.

In a non-limiting example we describe the generation and functionality of a recombinant adenovirus containing the murine HSA gene in the E1 region and the firefly luciferase gene in the gp19K region. The luciferase gene was excised from pAd/MLP-Luc (described in EP 0707071) as a HindIII-BamHI construct and cloned into the HindIII-BamHI sites of pBS.Eco-Eco/ad5ΔHIIIΔgp19KΔXbaI. Then the MscI-MunI fragment containing the luciferse gene was cloned into the corresponding sites of pBS.Eco-Eco/ad5Δgp19K generating pBS.Eco-Eco/ad5Δgp19K.luc. This restores the Eco-Eco fragment, but now with the luciferase gene in the place of gp19K.

To simplify further manipulation, the internal EcoRI sites in the luciferase insert were mutated without making changes to the amino acid sequence of the luciferase gene. One EcoRI site flanked the HindIII site in the 5' non-coding region of the luciferase insert and the other one was located 588 bp 3' from the starting ATG. A 695 bp PCR product was generated with the following primers: 5'-CGA TAA GCT TAA TTC CTT TGT GTT T-3' (SEQ ID NO: 12) and 5'-CTT AGG TAA CCC AGT AGA TCC AGA GGA GTT CAT-3' (SEQ ID NO: 13) and digested with HindIII and BstEII. This fragment was then ligated to HindIII-BstEII digested pBS.Eco-Eco/ad5Δgp19K.luc, replacing the corresponding insert in this vector. The resulting construct is named pBS.Eco-Eco/ad5Δgp19K.luc². The luciferase gene and part of the E3 region was then excised from this clone with SrfI and NotI and introduced in the corresponding sites in pBr/Ad.Bam-rITR generating clone pBr/Ad.Bam-rITRΔgp19K/luc².

The adapter plasmid pAd5/S1800HSA used for the replacement of E1 in the double insert virus contains the murine HSA gene driven by a retrovirus LTR-based promoter. This adapter plasmid was generated from the pAd5/L420-HSA construct described infra by replacement of the promoter sequence. First a PCR product was generated on a retroviral vector based on the MFG-S vector described in WO 95/34669 using the same primers as for the amplification of the L420 promoter fragment (described infra). This PCR amplifies the sequences corresponding to bp 453–877 in the MFG-S vector. The L420 promoter in pAd5/L420-HSA (FIG. 21) was then exchanged for the PCR fragment using the unique AvrII and HindIII sites. The resulting construct, pAd5/S430-HSA, was then digested with NheI and ScaI and the 4504 bp fragment containing the HSA gene, pA sequences, Ad5 sequences and vector sequences to the ScaI site in the ampicillin gene was isolated.

The construct pAd5/S430-HSA also was digested with XbaI and ScaI and the 1252 bp fragment (containing the remainder of the ampicillin gene, the left ITR and packaging signal from adenovirus and the 5' part of the S430 promoter) was isolated. A third fragment of 1576 bp was isolated from the MFG-S-based retroviral vector following an XbaI digestion and contains MFG-S sequences corresponding to bp 695–2271.

The adapter plasmid pAd5/S1800-HSA was constructed by ligating the three isolated fragments. The double insert virus Ad5/S1800-HSA.E3luc was generated (as described above) by transfection of the following DNA fragments into PER.C6 cells: pAd5/S1800-HSA digested with EcoRI and SalI(2 μg). At occurrence of CPE, the virus was harvested and amplified by serial passages on PER.C6 cells. The activity of this HSA-luc virus was compared to single insert ΔE1 viruses containing either the S1800-HSA or the CMV-luc transcription units in the E1 region. A549 cells were seeded at $2 \times 10^5$ cells/well and infected 5 hrs later with different amounts of the virus. Two days later transgene expression was measured. Luciferase activity was measured using a luciferase assay system (Promega) and expression of the murine HSA gene was measured with an α-HSA antibody (M1/69, Pharmingen). The results are listed in Table III.

This experiment shows that using the plasmid-based recombination system, double insert viruses can be made and that both inserts are functional. Furthermore, the luciferase activity of the double insert viruses is comparable to the CMV-driven luciferase activity of the control virus. Therefore, we conclude that the E3 promoter is highly active in A549 cells, even in the absence of E1A proteins.

In addition to manipulations in the E3 region, changes of (parts of) the E4 region can be accomplished easily in pBr/Ad.Bam-rITR. Generation and propagation of such a

TABLE III

Double insert viruses with different transgenes replacing the
E1 and E3/gp19K regions express both transgenes in human A549 cells.

| Virus[1] | Amount | % of cells with HSA expression | luciferase activity (light units) |
|---|---|---|---|
| IGAd/CMV-luc | $5 \times 10^7$ i.u. | ND | 25,726,074 |
|  | $2.5 \times 10^7$ i.u. | ND | 7,996,542 |
| IGAd/S1800-HSA | 100 μl ccl | 88% | ND |
|  | 50 μl ccl | 82% | ND |

TABLE III-continued

Double insert viruses with different transgenes replacing the
E1 and E3/gp19K regions express both transgenes in human A549 cells.

| Virus[1] | Amount | % of cells with HSA expression | luciferase activity (light units) |
|---|---|---|---|
| IGAd/S1800-HSA.E3luc | 1.2 × 10$^8$ i.u. | 97% | 32,451,300 |
|  | 6 × 10$^7$ i.u. | 97% | 24,716,586 |
|  | 1.2 × 10$^8$ i.u. | 100% | 13,294,321 |

[1]Note: All virus preps were clarified crude cell lysates (ccl). A clarified crude cell lysate was made by harvesting cells with medium at full CPE followed by three freeze/thaw cycles. pAd/S1800-HSA was not titrated.

virus, however, in some cases demands complementation in trans.

Example 3

Demonstration of the Competence of a Synthetic DNA Sequence, that is Capable of Forming a Hairpin Structure, to Serve as a Primer for Reverse Strand Synthesis for the Generation of Double-stranded DNA Molecules in Cells that Contain and Express Adenovirus Genes Name convention of the plasmids used:

| | |
|---|---|
| p | plasmid |
| I | ITR (Adenovirus Inverted Terminal Repeat) |
| C | Cytomegalovirus (CMV) Enhancer/Promoter Combination |
| L | Firefly Luciferase Coding Sequence | hac, haw Potential hairpin that can be formed after digestion with restriction endonuclease Asp718 in both the correct and in the reverse orientation, respectively (FIG. 15)

The naming convention is exemplified as follows. pICLhaw is a plasmid that contains the adenovirus ITR followed by the CMV-driven luciferase gene and the Asp718 hairpin in the reverse (non-functional) orientation.

Plasmids pICLhac, pICLhaw, pICLI and pICL were generated using standard techniques. The schematic representation of these plasmids is shown in FIGS. 16–19.

Plasmid pICL is derived from the following plasmids:

| | | |
|---|---|---|
| nt.1 | 457 | pMLP10 (Levrero et al, (1991) Gene 101:195–202) |
| nt.458 | 1218 | pCMVβ (Clontech, EMBL Bank No. U02451) |
| nt.1219 | 3016 | pMLP.luc (IntroGene, unpublished) |
| nt.3017 | 5620 | pBLCAT5 (Stein et al, (1989) Mol. Cell Biol. 9:4531–4). |

The plasmid has been constructed as follows:

The tet gene of plasmid pMLP10 has been inactivated by deletion of the BamHI-SalI fragment, to generate pBLP10ΔSB. Using primer set PCR/MLP1 (SEQ ID NO:37) and PCR/MLP3 (SEQ ID NO:38) a 210 bp fragment containing the Ad5-ITR, flanked by a synthetic SalI restriction site was amplified using pMLP10 DNA as the template. The PCR product was digested with the enzymes EcoRI and SgrAI to generate a 196 bp fragment. Plasmid pMLP10ΔSB was digested with EcoRI and SgrAI to remove the ITR. This fragment was replaced by the EcoRI-SgrAI-treated PCR fragment to generate pMLP/SAL.

Plasmid pCMV-Luc was digested with PvuII to completion and recirculated to remove the SV40-derived poly- adenylation signal and Ad5 sequences with exception of the Ad5 left-terminus. In the resulting plasmid, pCMV-lucΔAd, the Ad5 ITR was replaced by the Sal-site-flanked ITR from plasmid pMLP/SAL by exchanging the XmnI-SacII fragments. The resulting plasmid, pCMV-lucΔAd/SAL, the Ad5 left terminus and the CMV-driven luciferase gene were isolated as a SafI-SmaI fragment and inserted in the SalI and HpaI digested plasmid pBLCATS, to form plasmid pICL. Plasmid pICL is represented in FIG. 19; its sequence is presented in FIG. 20.

Plasmid pICL contains the following features:
- nt.1–457 Ad5 left terminus (Sequence 14–457 of human adenovirus type 5)
- nt.458–969 Human cytomegalovirus enhancer and immediate early promoter (Boshart et al, (1985) Cell 41:521–530) (from plasmid pCMVβ, Clontech, Palo Alto, USA)
- nt.970–1204 SV40 19S exon and truncated 16/19S intron (from plasmid pCMVβ)
- nt. 1218–2987 Firefly luciferase gene (from pMLP.luc)
- nt.3018–3131 SV40 tandem poly-adenylation signals from late transcript, derived from plasmid pBLCAT5)
- nt.3132–5620 pUC12 backbone (derived from plasmid pBLCAT5)
- nt.4337–5191 β-lactamase gene (Amp-resistance gene, reverse orientation)

Plasmids pICLhac and pICLhaw

Plasmids pICLhac and pICLhaw were derived from plasmid pICL by digestion of pICL with the restriction enzyme Asp718. The linearized plasmid was treated with Calf-Intestine Alkaline Phosphatase to remove the 51 phosphate groups. The partially complementary synthetic single-stranded oligonucleotides Hp/asp1 (SEQ ID NO:39) and Hp/asp2 (SEQ ID NO:40) were annealed and phosphorylated on their 5' ends using T4-polynucleotide kinase.

The phosphorylated double-stranded oligomers were mixed with the dephosphorylated pICL fragment and ligated. Clones containing a single copy of the synthetic oligonucleotide inserted into the plasmid were isolated and characterized using restriction enzyme digests. Insertion of the oligonucleotide into the Asp718 site will at one junction recreate an Asp718 recognition site, whereas at the other junction the recognition site will be disrupted. The orientation and the integrity of the inserted oligonucleotide was verified in selected clones by sequence analyses. A clone containing the oligonucleotide in the correct orientation (the Asp718 site close to the 3205 EcoRI site) was denoted pICLhac. A clone with the oligonucleotide in the reverse orientation (the Asp718 site close to the SV40 derived poly signal) was designated pICLhaw. Plasmids pICLhac and pICLhaw are represented in FIGS. 16 and 17.

Plasmid pICLI was created from plasmid pICL by insertion of the SalI-SgrAI fragment from pICL, containing the Ad5-ITR into the Asp718 site of pICL. The 194 bp SalI-SgrAI fragment was isolated from pICL, and the cohesive ends were converted to blunt ends using E. coli DNA polymerase I (Klenow fragment) and dNTP's. The Asp718 cohesive ends were converted to blunt ends by treatment with mungbean nuclease. By ligation clones were generated that contain the ITR in the Asp718 site of plasmid pICL. A clone that contained the ITR fragment in the correct orientation was designated pICLI (FIG. 18).

Generation of adenovirus Ad-CMV-hcTK. Recombinant adenovirus was constructed according to the method described in Patent application 95202213. Two components are required to generate a recombinant adenovirus. First, an adaptor-plasmid containing the left terminus of the adenovirus genome containing the ITR and the packaging signal, an expression cassette with the gene of interest, and a portion of the adenovirus genome which can be used for homologous recombination. In addition, adenovirus DNA is needed for recombination with the aforementioned adaptor plasmid. In the case of Ad-CMV-hcTK, the plasmid PCM-V.TK was used as a basis. This plasmid contains nt. 1–455 of the adenovirus type 5 genome, nt. 456–1204 derived from pCMVβ (Clontech, the PstI-StuI fragment that contains the CMV enhancer promoter and the 16S/19S intron from simian Virus 40), the Herpes Simplex Virus thymidine kinase gene (described in EP patent application 95202213.5), the SV40-derived polyadenylation signal (nt. 2533–2668 of the SV40 sequence), followed by the BglII-ScaI fragment of Ad5 (nt. 3328–6092 of the Ad5 sequence). These fragments are present in a pMLP10-derived (Levrero et al, (1991) Gene 101: 195–202) backbone. To generate plasmid pAD-CMVhc-TK, plasmid pCMV.TK was digested with ClaI (the unique ClaI-site is located just upstream of the TK open reading frame) and dephosphorylated with Calf-Intestine Alkaline Phosphate. To generate a hairpin-structure, the synthetic oligonucleotides HP/cla1 (SEQ ID NO:41) and HP/cla2 (SEQ ID NO:42) were annealed and phosphorylated on their 5'—OH groups with T4-polynucleotide kinase and ATP. The double-stranded oligonucleotide was ligated with the linearized vector fragment and used to transform E. coli strain "Sure". Insertion of the oligonucleotide into the ClaI site will disrupt the ClaI recognition sites. The oligonucleotide contains a new ClaI site near one of its termini. In selected clones, the orientation and the integrity of the inserted oligonucleotide was verified by sequence analyses. A clone containing the oligonucleotide in the correct orientation (the ClaI site at the ITR side) was denoted pAd-CMV-hcTK. This plasmid was co-transfected with ClaI-digested wild-type adenovirus-type5 DNA into 911 cells. A recombinant adenovirus in which the CMV-hcTK expression cassette replaces the E1 sequences was isolated and propagated using standard procedures.

To study whether the hairpin can be used as a primer for reverse strand synthesis on the displaced strand after replication has started at the ITR, the plasmid pICLhac was introduced into 911 cells, i.e. human embryonic retinoblasts transformed with the adenovirus E1 region. The plasmid pICLhaw served as a control: it contains the oligonucleotide pair HP/asp 1 (SEQ ID NO:39) and 2 (SEQ ID NO:40) in the reverse orientation but is otherwise completely identical to plasmid pICLhac. Also included in these studies were plasmids pICLI and pICL. In the plasmid pICLI the hairpin is replaced by an adenovirus ITR. Plasmid pICL contains neither a hairpin nor an ITR sequence. These plasmids served as controls to determine the efficiency of replication by virtue of the terminal hairpin structure. To provide the viral products other than the E1 proteins (these are produced by the 911 cells) required for DNA replication the cultures were infected with the virus IG.Ad.MLPI.TK after transfection. Several parameters were being studied to demonstrate proper replication of the transfected DNA molecules. First, DNA extracted from the cell cultures transfected with the aforementioned plasmids and infected with IG.Ad.ML-PI.TK virus was analyzed by Southern blotting for the presence of the expected replication intermediates, as well as for the presence of the duplicated genomes. Furthermore, from the transfected and IG.Ad.MLPI.TK infected cell populations, virus was isolated that can transfer a luciferase marker gene into luciferase negative cells and express it.

Plasmid DNA of plasmids pICLhac, pCLhaw, pICLI and pICL were digested with restriction endonuclease SalIand treated with mungbean nuclease to remove the 4 nucleotide single-stranded extension of the resulting DNA fragment. In this manner a natural adenovirus 5' ITR terminus on the DNA fragment was created. Subsequently, both the pICLhac and pICLhaw plasmids were digested with restriction endonuclease Asp718 to generate the terminus capable of forming a hairpin structure. The digested plasmids were introduced into 911 cells, using the standard calcium phosphate co-precipitation technique, four dishes for each plasmid. During the transfection, for each plasmid two of the cultures were infected with the IG.Ad.MLPI.TK virus using 5 infectious IG.Ad.MLPI.TK particles per cell. At twenty-hours post transfection and forty hours post-transfection one Ad.tk-virus-infected and one uninfected culture were used to isolate low molecular-weight DNA using the procedure devised by Hirt (as described in Einerhand et al, (1995) Gene Therapy 2:336–343). Aliquots of isolated DNA were used for Southern analysis. After digestion of the samples with restriction endonuclease EcoRI using the luciferase gene as a probe a hybridizing fragment of approx. 2.6 kb were detected in only the samples from the adenovirus-infected cells transfected with plasmid pICLhac. The size of this fragment was consistent with the anticipated duplication of the luciferase marker gene. This supports the conclusion that the inserted hairpin is capable of serving as a primer for reverse strand synthesis. The hybridizing fragment was absent if the IG.Ad.MLPI.TK virus was omitted, or if the hairpin oligonucleotide was inserted in the reverse orientation.

The restriction endoculease DpnI recognizes the tetra-nucleotide sequence 5'-GATC-3', but cleaves only methylated DNA, (that is, only plasmid DNA propagated in, and derived, from E. coli, not DNA that has been replicated in mammalian cells). The restriction endonuclease MboI recognizes the same sequences, but cleaves only unmethylated DNA (namely, DNA propagated in mammalian cells). DNA samples isolated from the transfected cells are incubated with MboI and DpnI and analyzed with Southern blots. These results demonstrated that only in the cells transfected with the pICLhac and the pICLI plasmids large DpnI-resistant fragments were present, that were absent in the MboI treated samples. These data demonstrate that only after transfection of plasmids pICLI and pICLhac replication and duplication of the fragments occur.

These data demonstrate that in adenovirus-infected cells linear DNA fragments that have on one terminus an adenovirus-derived inverted terminal repeat (ITR) and at the other terminus a nucleotide sequence that can anneal to sequences on the same strand, when present in single-stranded form thereby generate a hairpin structure, and will be converted to structures that have inverted terminal repeat sequences on both ends. The resulting DNA molecules will replicate by the same mechanism as the wild-type adenovirus genomes.

Example 4

Demonstration that the DNA Molecules that Contain a Luciferase Marker Gene, a Single Copy of the ITR, the Encapsidation Signal and a Synthetic DNA Sequence, that is Capable of Forming a Hairpin Structure, are Sufficient to Generate DNA Molecules that can be Encapsidated into Virions To demonstrate that the DNA molecules, generated in Example 3, containing two copies of the CMV-luc marker gene can be encapsidated into virions, virus was harvested lo from the remaining two cultures via three cycles of freeze-thaw crushing and was used to infect murine fibroblasts. Forty-eight hours after infection the infected cells are assayed for luciferase activity. To exclude the possibility that the luciferase activity has been induced by transfer of free DNA, rather than via virus particles, virus stocks were treated with DNaseI to remove DNA contaminants. Furthermore, as an additional control, aliquots of the virus stocks were incubated for 60 minutes at 56° C. The heat treatment does not affect the contaminating DNA, but does inactivate the viruses. Significant luciferase activity was only found in the cells after infection with the virus stocks derived from IG.Ad.MLPI.TK-infected cells transfected with the pICLhc and pICLI plasmids. Neither in the non-infected cells, nor in the infected cells transfected with the pICLhw and pICL was significant luciferase activity demonstrated. Heat inactivation, but not DNaseI treatment, completely eliminated luciferase expression, demonstrating that adenovirus particles, and not free (contaminating) DNA fragments were responsible for transfer of the luciferase reporter gene.

These results demonstrate that these small viral genomes can be encapsidated into adenovirus particles and suggest that the ITR and the encapsidation signal are sufficient for encapsidation of linear DNA fragments into adenovirus particles. These adenovirus particles can be used for efficient gene transfer. When introduced into cells that contain and express at least some of the adenovirus genes (namely E1, E2, E4, and L, and VA), recombinant DNA molecules that include at least one ITR, at least part of the encapsidation signal as well as a synthetic DNA sequence, that is capable of forming a hairpin structure, have the intrinsic capacity to autonomously generate recombinant genomes which can be encapsidated into virions. Such genomes and vector system can be used for gene transfer.

Example 5

Demonstration that DNA Molecules Which Contain Nucleotides 3510–35953 (namely 9.7–100 map units) of the Adenovirus Type 5 Genome (thus lack the E1 protein-coding regions, the right-hand ITR and the encapsidation sequences) and a Terminal DNA Sequence that is Complementary to a Portion of the Same Strand of the DNA Molecule When Present in Single-stranded Form Other than the ITR, and as a result is Capable of Forming a Hairpin Structure, can Replicate in 911 Cells In order to develop a replicating DNA molecule that can provide the adenovirus products required to allow the above-mentioned ICLhac vector genome and alike minimal adenovectors to be encapsidated into adenovirus particles by helper cells, the Ad-CMV-hcTK adenoviral vector was developed. Between the CMV enhancer/promoter region and the thymidine kinase gene, the annealed oligonucleotide pair (Table I) HP/cla 1 and 2 was inserted. The vector Ad-CMV-hcTK was propagated and produced in 911 cell using standard procedures. This vector was grown and propagated exclusively as a source of DNA used for transfection. DNA of the adenovirus Ad-CMV-hcTK was isolated from virus particles that had been purified using CsC1 density-gradient centrifugation by standard techniques. The virus DNA was digested with restriction endonuclease ClaI. The digested DNA was size-fractionated on an 0.7% agarose gel and the large fragment was isolated and used for further experiments. Cultures of 911 cells were transfected with the large ClaI-fragment of the Ad-CMV-hcTK DNA using standard calcium phosphate co-precipitation techniques. Much like in the previous experiments with plasmid pICLhac, the Ad-CMV-hc replicates starting at the right-hand ITR. Once the 1-strand is displaced, a hairpin can be formed at the left-hand terminus of the fragment. This facilitates DNA polymerase elongation of the chain towards the right-hand side. The process proceeds until the displaced strand is completely converted to its double-stranded form. Finally, the right-hand ITR is recreated, and in this location, normal adenovirus replication-initiation and elongation occur. The polymerase reads through the hairpin, thereby duplicating the molecule. The input DNA molecule of 33250 bp, that had on one side an adenovirus ITR sequence and at the other side a DNA sequence that had the capacity to form a hairpin structure is duplicated so that both ends contain an ITR sequence. The resulting DNA molecule consists of a palindromic structure of approximately 66500 bp.

This structure is detected in low-molecular weight DNA extracted from transfected cells using Southern analysis. The palindromic nature of the DNA fragment can be demonstrated by digestion of the low-molecular weight DNA with suitable restriction endonucleases and Southern blotting with the HSV-TK gene as the probe. This molecule can replicate itself in the transfected cells by virtue of the adenovirus gene products that are present in the cells. In part, the adenovirus genes are expressed from templates that are integrated in the genome of the target cells (namely, the E1 gene products), the other genes reside in the replicating DNA fragment itself. This linear DNA fragment cannot be encapsidated into virions. Not only does it lack all the DNA sequences required for encapsidation, but its size also is much too large to be encapsidated.

Example 6

Demonstration that DNA Molecules Which Contain Nucleotides 3503–35953 (viz. 9.7–100 map units) of the Adenovirus Type 5 Genome (thus lack the E1 protein-coding regions, the right-hand ITR and the encapsidation sequences) and a Terminal DNA Sequence that is Complementary to a Portion the Same Strand of the DNA Molecule Other than the ITR, and as a Result is Capable of Forming a Hairpin Structure, can Replicate in 911 Cells and can Provide the Helper Functions Required to Encapsidate the pICLI and pICLhac Derived DNA Fragments The purpose of the next series of experiments is to demonstrate that the DNA molecule described in Example 5 can be used to encapsidate the minimal adenovectors described in Examples 3 and 4.

The large fragment isolated after endonuclease ClaI-digestion of Ad-CMV-hcTK DNA was introduced into 911 cells (as described in Example 5) together with endonuclease SalI, mungbean nuclease, endonuclease Asp718-treated plasmid pICLhac, or as a control similarly treated plasmid pICLhaw. After 48 hours virus was isolated by freeze-thaw crushing of the transfected cell population. The virus preparation was treated with DNaseI to remove contaminating free DNA. The virus was used subsequently to infect Rat2 fibroblasts. Forty-eight hours post infection the cells were assayed for luciferase activity. Only in the cells infected with virus isolated from the cells transfected with the pICLhac plasmid, and not with the pICLhaw plasmid, was significant luciferase activity demonstrated. Heat inactivation of the virus prior to infection completely abolished the luciferase activity, indicating that the luciferase gene was transferred by a viral particle. Infection of 911 cell with the virus stock did not result in any cytopathological effects, demonstrating that pICLhac was produced without any infectious helper virus being propagated on 911 cells. These results demonstrate that the proposed method can be used to produce stocks of minimal-adenoviral vectors, that are completely devoid of infectious helper viruses that are able to replicate autonomously on adenovirus-transformed human cells or on non-adenovirus transformed human cells.

Example 7

Construction of Plasmids for the Generation and Production of Minimal Adenoviral Vectors A minimal adenovirus vector contains as operably linked components the adenovirus-derived cis elements necessary for replication and packaging, with or without foreign nucleic acid molecules to be transferred. Recently, the lower limit for efficient packaging of adenoviral vectors has been determined at 75% of the genome length (Parks and Graham, 1997 [need cite]). To allow flexible incorporation of various lengths of stuffer fragments, a multiple cloning site (MCS) was introduced into a minimal adenoviral vector. To obtain a minimal adenoviral vector according to the invention, the following constructs were made: pAd/L420-HSA (FIG. 19) was digested with BglII and SalI and the vector-containing fragment was isolated. This fragment contains the left ITR and packaging signal from Ad5 and the murine HSA gene driven by a modified retroviral LTR. The right ITR of adenovirus was amplified by PCR on pBr/Ad.BamnHI-rITR template DNA using the following primers: PolyL-ITR: 5'-AAC-TGC-AGA-TCT-ATC-GAT-ACT-AGT-CAA-TTG-CTC-GAG-TCT-AGA-CTA-CGT-CAC-CCG-CCC-CGT-TCC-3' (SEQ ID NO: 14) and ITR-BSN: 5'-CGG-GAT-CCG-TCG-ACG-CGG-CCG-CAT-CAT-CAA-TAA-TAT-ACC-3' (SEQ ID NO: 15). The amplified fragment was digested with PstI and BamHI and cloned into pUC119 digested with the same enzymes. After sequence confirmation of correct amplification of the ITR and the MCS, a BglII-SalI fragment was isolated and cloned into the BglII/SalI-digested pAd/L420-HSA fragment described above. The resulting clone was named pAd/L420-HSA.ITR. To be able to manipulate constructs of lengths exceeding 30 kb, the minimal adenoviral vector pAd/L420-HSA.ITR was subcloned in a cosmid vector background. To this end, the cosmid vector pWE15 was modified to remove restriction sites in the backbone. pWE15 was digested with PstI and fragments of 4 kb and 2,36 kb were isolated from agarose gel and ligated together. The resulting clone, stripped of the SV40 ori/early promoter and neomycine resistance coding sequence, was named pWE20. Then, pWE20 was digested with ClaI and HindIII and the sticky ends were filled in with Klenow enzyme. A 6354 bp blunt fragment was ligated to a phosphorylated NsiI linker with the following sequence: 5'-CGATGCATCG-3' (SEQ ID NO: 16). The ligated DNA was phenol/chloroform extracted, precipitated with EtOH to change buffers, and digested with excess NsiI. Digested DNA was separated from the linkers by electrophoresis, isolated and religated. The resulting clone was named pWE25. Correct insertion of the NsiI linker was confirmed by restriction enzyme digestion and sequencing. To construct the minimal adenoviral vector, pAd/L420-HSA.ITR was digested with ScaI and NotI and the 2 kb fragment containing part of the ampicillin gene and the adeno ITRs was cloned into pWE25 digested with ScaI and NotI. The resulting clone was named pMV/L420H (FIG. 24). This clone allows easy manipulation to exchange the promoter and/or gene, and also allows insertion of DNA fragments of lengths not easily cloned into normal plasmid backbones.

Plasmid pMV/CMV-LacZ was made by exchanging the L420-HSA fragment (SnaBI-BamHI) for a fragment from pcDNA3-nlsLacZ (NruI-BamHI) containing the CMV promoter and LacZ coding sequences. pcDNA3-nlsLacZ was constructed by insertion of a KpnI-BamHI fragment obtained after PCR amplification of the nlsLacZ coding sequences into pcDNA3 (Invitrogen) digested with KpnI and BamHI. The PCR reaction was performed on a pMLP-.nlsLacZ template DNA using the primers 1: 5'-GGG-GTG-GCC-AGG-GTA-CCT-CTA-GGC-TTT-TGC-AA-3'(SEQ ID NO:17) and 2: 5'-GGG-GGG-ATC-CAT-AAA-CAA-GTT-CAG-AAT-CC-3'(SEQ ID NO: 18). Correct amplification and cloning were confirmed by assaying β-galactosidase expression in a transient transfection experiment on 911 cells.

The vector pAd/MLPnlsLacZ was made as follows: pMLP10 (Levrero et al, (1991) *Gene* 101: 195–202) was digested with HindIII and BamHI and ligated, in a three-part ligation, to a 3.3 kb AvrII-BamHI fragment from L7RHβgal (Kalderon et al, (1984) *Cell* 499–509), and a synthetic linker with HindIII and XbaI overhang. The linker was made by annealing two oligonucleotides of sequence 5'-AGC TTG AAT TCC CGG GTA CCT-3' (SEQ ID NO:19) and 5'-CTA GAG GTA CCC GGG AAT TCA-3' (SEQ ID NO:20). The resulting clone was named pMLP.nlsLacZ/-Ad. Next, pMLP.nlsLacZ/-Ad was digested with BamHI and NruI and the vector containing fragment was ligated to a 2766 bp BglII-ScaI fragment from pAd5SalB (Bernards et al, (1982) *Virology* 120:422–432). This resulted in the adapter plasmid pMLP.nlsLacZ (described in EP 0 707 071).

Propagation of a minimal adenoviral vector can only be achieved by expression of adenovirus gene products. Expression of adenovirus gene products, at levels high enough to sustain production of large quantities of virus, requires replication of the coding nucleic acid molecule. Usually, therefore, replicating helper viruses are used to complement the minimal adenoviral vectors. The present invention, however, provides packaging systems for minimal adenoviral vectors without the use of helper viruses. One of the methods of the invention makes use of a replicating DNA molecule that contains the 5'-ITR and all adenoviral sequences between bp 3510 and 35938, i.e., the complete adenoviral genome except for the E1 region and the packaging signal. Construct pWE/Ad.Δ5' (FIG. 23) is an example of a replicating molecule according to the invention that contains two adenoviral ITRs. pWE/Ad.Δ5'. It has been made in a cosmid vector background from three fragments. First, the 5' ITR from Ad5 was amplified using the following primers: ITR-EPH: 5'-CGG-AAT-TCT-TAA-TTA-AGT-TAA-CAT-CAT-CAA-TAA-TAT-ACC-3' (SEQ ID NO:21) and ITR-pIX: 5'-ACG-GCG-CGC-CTT-AAG-CCA-CGC- CCA-CAC-ATT-TCA-GTA-CGT-ACT-AGT-CTA-CGT-CAC-CCG-CCC-CGT-TCC-3'(SEQ ID NO:22). The resulting PCR fragment was digested with EcoRI and AscI and cloned into vector pNEB193 (New England Biolabs) digested with the same enzymes. The resulting construct was named pNEB/ITR-pIX. Sequencing confirmed correct amplification of the Ad5 sequences in the left ITR (Ad5 sequences 1 to 103) linked to the pIX promoter (Ad5 sequences 3511 to 3538) except for a single mismatch with the expected sequence according to GenBank (Accession no.: M73260/M29978), i.e., an extra C-residue was found just upstream of the AflII site. This ITR-pIX fragment was isolated with EcoRI and AflII and ligated to a EcoRI-AflII vector fragment containing Ad5 sequences 3539–21567. The latter fragment was obtained by digestion of pBr/Ad.Cla-Bam (supra) with EcoRI and partially with AflII. The resulting clone was named pAd/LITR(Δ5')-BamHI. The final construct pWE/Ad.Δ5' was made by ligating cosmid vector pWE15.Pac (supra) digested with PacI to pAd/LITR (Δ5')-BamHI digested with PacIlBamHI and pBr/Ad.Bam-rITR.pac#2 (supra) digested with PacI/BamHI (FIG. 23).

An alternative method to produce packaging systems for minimal adenoviral vectors without the use of helper viruses according to the invention is to use a replicating DNA molecule that contains the complete adenoviral genome except for the E1 region and the packaging signal and in which one of the ITRs is replaced by a fragment containing a DNA sequence complementary to a portion of the same strand other than the ITR and that therefore is able to form a hairpin structure (FIG. 10). In a non-limiting example, said DNA sequence complementary to a portion of the same strand other than the ITR is derived from the adeno-associated virus (AAV) terminal repeat. Such a replicating DNA molecule is made following the same cloning strategy as described for pWE/Ad.Δ5', but now starting with the AAV terminal repeat linked to part of the adenoviral pIX promoter. To this end, the adenoviral ITR sequences between the HpaI and SpeI sites in construct pNEB/ITR-pIX were exchanged for the AAV ITR by introducing the PvuIIlXbaI fragment from psub201(+) containing the AAV ITR (Samulski et al, (1989) J. Virol. 63:3822–3828). This results in construct pWE/AAV.Δ5' that replicates in an E1 complementing cell line.

Another alternative packaging system for minimal adenoviral vectors is described infra and makes use of the replication system of SV40. A functional helper molecule according to this method contains at least the adenoviral sequences necessary to sustain packaging of a minimal construct but not the E1 sequences and packaging signal, and preferably also lacking ITRs. This adenovirus-derived entity has to be present on a vector that contains, besides the sequences needed for propagation in bacteria, an origin of replication from SV40 virus. Transfection of such a molecule together with the minimal adenoviral vector, described supra, into a packaging cell line (e.g. PER.C6) expressing, besides the E1 proteins, SV40 derived Large T antigen proteins, results in Large T-dependent replication of the adenovirus-derived helper construct. This replication leads to high levels of adenoviral proteins necessary for replication of the minimal adenoviral vector and packaging into virus particles. In this way, there is no sequence overlap that leads to homologous recombination between the minimal adenoviral vector construct and the helper molecule. In addition, there is no sequence overlap that leads to homologous recombination between the helper molecule and minimal adenoviral vector on the one side and the E1 sequence in the packaging cell on the other side.

Replication of a 40 kb adenoviral construct was investigated in cells expressing SV40 Large T proteins. Hereto, $2\times10^6$Cos-1 cells were transfected in a T25 flask with the following constructs complexed with lipofectamine reagent (Life techn.): the 8 kb cosmid vector pWE.pac, the 40.5 kb construct pWE/Ad.AflII-rITR and three clones (#1, #5 and #9) of the 40.6 kb construct pWE/Ad.Δ5' (described infra). Control transfections were carried out with the constructs pWE.pac and pWE1Ad.AflII-rITR digested with PacI enzyme and a CMV-LacZ expression vector without the SV40 ori sequence. Transfection efficiency was 50% as determined by a separate transfection using the CMV-LacZ vector and X-gal staining after 48 hrs. All cells were harvested 48 hrs. following transfection and DNA was extracted according to the Hirt procedure (as described in Einerhand et al, (1995) Gene Therapy 2:336–343). Final pellets were resuspended in 50μl TE+RNase (20 μg/ml) and 10 μl samples were digested with MboI (35 units overnight at 37° C.). Undigested samples (5 μl) and MboI digested samples were run on a 0.8% agarose gel, transferred to a nylon filter (Amersham) and hybridized to radioactive probes according to standard procedures. One probe was derived from an 887 bp DpnI fragment from the cosmid vector pWE.pac and one was derived from a 1864 bp Bsi(I-BamHI fragment from adenoviral sequences. These probes hybridize to a 887 bp band and a 1416 bp respectively in MboI digested material. Input DNA from bacterial origin is methylated and therefore not digested with MboI. In this way it is possible to specifically detect DNA that is replicated in eukaryotic cells. FIG. 26A shows a schematic presentation of the construct pWE/Ad.Δ5' and the locations of the SV40 origin of replication, the pWE-derived probe and the adenovirus-derived probe. The lower part presents the autoradiograms of the Southern blots hybridized to the adenovirus probe (B) and the pWE probe (C). See legends for explanation of sample loading. These experiments show that all lanes that contain material from Cos-1 cells that are transfected with plasmids harbouring an SV40 ori contain MboI sensitive DNA and show a specific band of the expected length. The bands specific for replication in the lanes with Cos-1 cells transfected with PacI digested material (lanes B17/18 and C 15–18) probably result from incomplete PacI digestion. From these experiments it can be concluded that it is possible to replicate large DNA fragments with the SV40 LargeT/ori system in eukaryotic cells.

Example 8

A functional adenovirus helper molecule lacking ITR sequences was constructed starting with the clone pWE/Ad.D5' described supra. pWE/Ad.D5' was digested with Bst1107I and the 17.5 kb vector-containing fragment was religated to give pWE/Ad.D5'-Bst1107I. This clone was then used to amplify the 3' part of the adenovirus genome sequences without the right ITR. A 2645 bp PCR fragment was generated using the primers Ad3'/Forw: 5'-CGG AAT TCA TCA GGA TAG GGC GGT GG-3' (SEQ ID NO:23) and Ad3'/Rev: 5'-CGG GAT CCT ATC GAT ATT TAA ATG TTT TAG GGC GGA GTA ACT TG-3' (SEQ ID NO:24). The amplified fragment was digested with EcoRI and BamHI and subcloned in pBr322 digested with the same enzymes. After confirmation of correct amplification by sequencing, the 2558 bp SbfI-ClaI fragment of this clone was recloned in pWE/Ad.D5'-Bst1107I digested with the same enzymes. The resulting construct lacks the right ITR and is named pWE/ΔrI-Bst11071. Next, in this clone the left ITR was replaced by a linker with a PacI and AflII overhang made up by annealing the following primers: PA-pIX1

5'-TAA GCC ACT AGT ACG TAC TGA AAT GTG TGG GCG TGG C-3' (SEQ ID NO:25) and PA-pIX2 5'-TTA AGC CAC GCC CAC ACA TTT CAG TAC GTA CTA GTGOGCT TAA T-3' (SEQ ID NO:26). This removed the left ITR and restored correct sequence of the pIX promoter. The clone is named pWE/ΔITR-Bst1107I. Correct insertion of the double stranded linker was confirmed by sequencing. The deleted Bst1107I fragment was then cloned back into pWE/ΔITR-Bst1107I and the correct orientation was checked by restriction digestion. The resulting clone is named pWE/Ad-H. Following transfection of this DNA molecule into packaging cells that express adenoviral E1 proteins and the SV40 Large T antigen, replication of that molecule takes place resulting in high levels of adenoviral proteins encoded by the adenoviral entity on that molecule.

Example 9

Miniaturized, Multiwell Production of Recombinant Adenoviral Vectors

A 96-well microtiter tissue culture plate (plate 1) (Greiner, The Netherlands, catalogue #6555180) was first coated with poly-L-lysine (PLL, 0.1 mg/ml) (Sigma) dissolved in sterile water by incubating each well for 20–120 minutes at room temperature. Alternatively, precoated 96-well plates can be used (Becton and Dickinson). After the incubation with PLL, each well was washed two times with 100 μl sterile water and dried at room temperature for at least two hours. The day before transfection PER.C6 cells were harvested using trypsin-EDTA and counted. The cells were then diluted to a suspension of 45,000 cells per 100 μl followed by seeding 100 μl per well of the PLL coated 96-well plates. The next day 2.6 μl of Sal I linearized pAd/CMV-LacZ and 2.6 μl of PacI linearized pWE-Ad.AflII-rITR plasmid DNA (both 1 μg/μl) and 95 μl serum free Dulbecco's Modified Eagles Medium (DMEM) were mixed with 25.6 μl lipofectamine diluted in 74.4 μl serum free DMEM by adding the lipofectamine to the DNA mix. The DNA/lipofectamine mixture was left at room temperature for 30 minutes after which 1.3 ml serum free media was added. The latter mixture was then added (30 μl per well) to PER.C6 seeded wells that were washed with 200 μl DMEM prior to transfection. After 3 hours in a humidified $CO_2$ incubator (37° C., 10% $CO_2$) 200 μl DMEM with 10% fetal calf serum 10 mM $MgCl_2$ was added to each well and the plates were returned to the humidified $CO_2$ incubator (37° C., 10% $CO_2$). The next day the medium of each well was replaced with 200 μl DMEM, 10% FCS, 10 mM $MgCl_2$. The plates were then left in the humidified $CO_2$ incubator for an additional three days after which the wells were subjected to freezing at −20° C. for at least 1 hour followed by thawing and resuspension by repeated pipetting. Transfection efficiency was determined using lacZ staining in additional plates and found to be approximately 40% for each transfected well of PER.C6 cells. An aliquot of 100 μl of freeze/thawed transfected cells was transferred to each well of a plate with new PER.C6 cells seeded as described above without PLL coated plates (plate 2). The second 96-well plate with PER.C6 cells incubated with freeze/thaw cell lysate of the first transfected plate was checked for CPE. At least 5% of the wells showed clear CPE after 2 days. Four days after infection with the lysate from plate 1 the plate was subjected to one freeze-thaw cycle and 10 μl from each lysed well was added to wells of a plate seeded with A549 cells ($1 \times 10^4$ cells per well seeded in 100 μl in DMEM, 10% FCS the day before). Two days after infection the wells were stained for lacZ activity. Of the infected wells 96% were infected and stained blue. All wells stained and a large number of wells showed 100% blue staining and thus transduction of all cells with adenoviral vector carrying lacZ. Extrapolated from MOI experiments in tissue culture flasks the adenoviral titer of well-produced virus is around $10^6$–$10^7$ infectious units per ml.

The subject invention discloses methods and compositions for the high throughput delivery and expression in a host of sample nucleic acid(s) encoding product(s) of unknown function. Methods are described for the construction of complementing cell lines, libraries of adenovirus derived plasmids containing sample nucleic acids, packaging the adenovirus-derived plasmids into adenovirus vectors, infecting a host with the adenovirus vectors that express the product(s) of the sample nucleic acid(s) in the host, identifying an altered phenotype induced in the host by the product(s) of the sample nucleic acids, and thereby assigning a function to the product(s) encoded by the sample nucleic acids. The sample nucleic acids can be, for example, synthetic oligonucleotides, DNAs, cDNAs and can encode, for example, polypeptides, antisense nucleic acids, or GSEs. The methods can be fully automated and performed in a multiwell format to allow for convenient high throughput analysis sample nucleic acid libraries.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. A method of producing a recombinant adenoviral vector library consisting of distinct recombinant adenoviral vectors, wherein each distinct vector contains an unique nucleic acid, by:

growing a plurality of cell cultures, each said cell culture containing at least one cell comprising adenoviral nucleic acid sequences consisting essentially of adenoviral E1-complementing sequences, and transfecting, into said at least one cell of each said cell culture, an adapter plasmid and a recombinant nucleic acid, under conditions such that said recombinant adenoviral vector library is produced, wherein (A) i) said adapter plasmid comprises adenoviral nucleic acid sequence but does not comprise E1 region sequences that overlap with E1 region sequences in said at least one cell and E1 region sequences that overlap with E1 region sequences in said recombinant nucleic acid, wherein said overlap would otherwise result in generation of replication competent adenovirus in said at least one cell, (A) ii) said adapter plasmid further does not comprise E2B region sequences other than essential E2B sequences, E2A region sequences, E3 region sequences and E4 region sequences, (A) iii) said adapter plasmid further comprises, in operable configuration, a nucleic acid sequence coding for a functional Inverted Terminal Repeat, a functional encapsidation signal, and sufficient adenoviral sequences to allow for homologous recombination with said recombinant nucleic acid, and a promoter and a unique nucleic acid sequence operatively linked to said promoter; and wherein (B) said recombinant nucleic acid comprises, in operable configuration, a sequence for a functional Inverted Terminal Repeat and adenoviral sequence sufficient for replication, wherein said recombinant nucleic acid sequence partially overlaps with sequence of said adapter plasmid to allow for homologous recombination resulting in replication-defective, recombinant adenoviral vector.

2. The method according to claim 1 wherein at least one of said adapter plasmids and said recombinant nucleic acid is heat denatured prior to transfecting said plurality of cells or ancestors of said plurality of cells.

3. The method according to claim 1 wherein said adenoviral E1-complementing sequences, said adapter plasmid and said recombinant nucleic acid contain no overlapping sequence which allows for homologous recombination resulting in replication competent adenovirus in a cell transfected therewith.

4. A method of producing a recombinant adenovirus vector library consisting essentially of a plurality of cell cultures containing distinct recombinant adenoviral vectors each containing a unique nucleic acid, by:

growing a plurality of cell cultures, each said cell culture containing at least one cell, said at least one cell comprising adenoviral E1-complementing sequences; and transfecting, under conditions whereby said recombinant adenovirus vector library is produced, said at least one cell with i) a first recombinant nucleic acid comprising adenoviral sequence coding, in operable configuration, for one functional Inverted Terminal Repeat, and sequence coding for a promoter and a unique nucleic acid operatively linked to said promoter; and ii) a second recombinant nucleic acid comprising adenoviral sequence coding, in operable configuration, for one functional Inverted Terminal Repeat and sufficient for replication, wherein said second recombinant nucleic acid does not comprise the adenoviral E1 region, wherein one of said first or second recombinant nucleic acids comprises a functional encapsidation signal.

5. The method according to claim 4, wherein at least one of said plurality of cell cultures is in a multiwell format.

6. The method according to claim 4 wherein said adenovirus E1-complementing sequences, said first recombinant nucleic acid and said second recombinant nucleic acid contain no overlapping sequence which allows for homologous recombination resulting in replication competent adenovirus in a cell transfected therewith.

7. The method according to claim 4 wherein at least one of said plurality of cell cultures is a PER.C6 cell culture.

8. The method according to claim 4 wherein at least one of said plurality of cell cultures is grown in a medium containing sodium butyrate in an amount sufficient to enhance production of said recombinant adenovirus vector.

9. The method according to claim 4 wherein said at least one cell further comprises at least one of an adenovirus preterminal protein and a polymerase complementing sequence.

10. The method according claim 4 wherein said at least one cell further comprises an adenovirus E2 complementing sequence.

11. The method according to claim 10 wherein said E2 complementing sequence is selected from the group consisting of an E2A complementing sequence and an E2B complementing sequence.

12. The method according to claim 1 wherein said at least one cell further comprises a recombinase protein, whereby said homologous recombination resulting in replication-defective, recombinant adenovirus is enhanced.

13. The method according to claim 12 wherein said recombinase protein is a *Kluyveromyces waltii* recombinase.

14. The method according to claim 1 wherein said at least one cell further comprises a nucleotide sequence coding for a recombinase protein.

15. The method according to claim 14 wherein said recombinase protein is *Kluyveromyces waltii* recombinase.

16. The method according to claim 4 wherein each cell culture consists essentially of cells containing said recombinant adenovirus vectors, comprising said unique nucleic acids that are identical.

17. The method according claim 4 wherein said promoter is an inducible promoter.

18. The method according to claim 4 wherein said promoter is repressed or down modulated by an adenovirus E1 gene product.

19. The method according to claim 18 wherein said promoter comprises an AP1 dependent promoter.

20. The method according to claim 19 wherein said AP1 dependent promoter is derived from a collagenase, a c-myc, a monocyte chemoattractant protein or a stromelysin gene.

21. The method according to claim 4 wherein said unique nucleic acid sequence encodes a product of unknown function.

22. The method according to claim 4 wherein said nucleic acid sequence is selected from the group consisting of synthetic oligonucleotides, DNAs, cDNAs, genes, ESTs, antisense nucleic acids and genetic suppressor elements.

23. The method according to claim 4 wherein said method is automated.

24. A method of producing a recombinant adenovirus vector library consisting essentially of distinct recombinant adenoviral vectors each distinct vector containing a unique nucleic acid, said method comprising:

growing a plurality of cell cultures containing at least one cell, said one cell expressing adenoviral sequence consisting essentially of E1-region sequences and expressing one or more functional gene products encoded by at least one adenoviral region selected from an E2A region and an E4 region; and transfecting, under conditions whereby said recombinant adenovirus vector library is produced, said at least one cell in each of said plurality of cell cultures with i) an adapter plasmid comprising adenoviral sequence coding, in operable configuration, for a functional Inverted Terminal Repeat, a functional encapsidation signal, and sequences sufficient to allow for homologous recombination with a first recombinant nucleic acid, and not coding for E1 region sequences which overlap with E1 region sequences in said at least one cell, for E1 region sequences which overlap with E1 region sequences in a first recombinant nucleic acid, for E2B region sequences other than essential E2B sequences, for E2A region sequences, for E3 region sequences and for E4 region sequences, and further comprises a unique nucleic acid sequence and promoter operatively linked to said unique nucleic acid sequence; and ii) a first recombinant nucleic acid comprising adenoviral sequence coding, in operable configuration, for a functional adenoviral Inverted Terminal Repeat and for sequences sufficient for replication in said at least one cell, but not comprising adenoviral E1 region sequences which overlap with E1 sequences in said at least one cell, and not comprising E2A region sequences or E4 region sequences expressed in said plurality of cells which would otherwise lead to production of replication competent adenovirus wherein said first recombinant nucleic acid has sufficient overlap with said adapter plasmid to provide for homologous recombination resulting in production of recombinant adenovirus in said at least one cell.

25. The method according to claim 24 wherein said first recombinant nucleic acid further comprises no E3 region sequences.

26. The method according to claim 24 wherein said at least one cell expresses at least one functional E2A gene product.

27. The method according to claim 26 wherein said at least one functional E2A gene product is a mutated gene product.

28. The method according to claim 27 wherein said mutated gene product is temperature sensitive.

29. The method according to claim 24 wherein at least one of said adapter plasmids and said first recombinant nucleic acids is heat denatured prior to transfecting said at least one cell or ancestor of said at least one cell.

30. The method according to claim 24 wherein said at least one cell expresses one or more functional gene product encoded by E2B region sequences and wherein said first recombinant nucleic acid comprises E2B region sequences required for adenoviral generation but does not comprise E2B region sequences coding for said functional E2B region gene products.

31. The method according to claim 30 wherein said at least one cell expresses all gene products encoded by E2B region sequences, and said adapter plasmid does not comprise E2B gene region sequences.

32. The method according to claim 24 wherein said at least one cell is a PER.C6 cell culture.

33. The method according to claim 24 wherein said promoter is an inducible promoter.

34. A plurality of cell cultures containing a recombinant replication-defective adenoviral vector library consisting essentially of distinct recombinant adenoviral vectors each distinct vector containing a unique nucleic acid, wherein said recombinant replication-defective adenoviral vector library is produced according to the method of claim 24.

35. The plurality of cultures of claim 34 wherein said at least one cell is a PER.C6 cell.

36. The method according to claim 24 wherein said method is automated.

* * * * *

SEQUENCE LISTING (1) GENERAL INFORMATION:

(iii) NUMBER OF SEQUENCES: 47

(2) INFORMATION FOR SEQ ID NO:1:

(i) SEQUENCE CHARACTERISTICS:
      (A) LENGTH: 23 base pairs
      (B) TYPE: nucleic acid
      (C) STRANDEDNESS: double

```
        (D) TOPOLOGY: linear (ii) MOLECULE TYPE: other nucleic acid (xi) SEQUENCE DESCRIPTION: SEQ ID NO:1:

AATTGTCTTA ATTAACCGCT TAA                                              23

(2) INFORMATION FOR SEQ ID NO:2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:2:

AATTGTCTTA ATTAACCGC                                                   19

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

AATTGCGGTT AATTAAGAC                                                   19

(2) INFORMATION FOR SEQ ID NO:4:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

CTGTACGTAC CAGTGCACTG GCCTAGGCAT GGAAAAATAC ATAACTG                    47

(2) INFORMATION FOR SEQ ID NO:5:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

GCGGATCCTT CGAACCATGG TAAGCTTGGT ACCGCTAGCG TTAACCGGGC GACTCAGTCA      60

ATCG                                                                   64

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear
```

(ii) MOLECULE TYPE: other nucleic acid (xi) SEQUENCE DESCRIPTION: SEQ ID NO:6:

GCGCCACCAT GGGCAGAGCG ATGGTGGC                                    28

(2) INFORMATION FOR SEQ ID NO:7:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:7:

GTTAGATCTA AGCTTGTCGA CATCGATCTA CTAACAGTAG AGATGTAGAA            50

(2) INFORMATION FOR SEQ ID NO:8:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:8:

GGGTATTAGG CCAAAGGCGC A                                           21

(2) INFORMATION FOR SEQ ID NO:9:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:9:

GATCCCATGG AAGCTTGGGT GGCGACCCCA GCG                              33

(2) INFORMATION FOR SEQ ID NO:10:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:10:

GATCCCATGG GGATCCTTTA CTAAGTTACA AAGCTA                           36

(2) INFORMATION FOR SEQ ID NO:11:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:11:

```
GTCGCTGTAG TTGGACTGG                                                19

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

CGATAAGCTT AATTCCTTTG TGTTT                                         25

(2) INFORMATION FOR SEQ ID NO:13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:13:

CTTAGGTAAC CCAGTAGATC CAGAGGAGTT CAT                                33

(2) INFORMATION FOR SEQ ID NO:14:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:14:

AACTGCAGAT CTATCGATAC TAGTCAATTG CTCGAGTCTA GACTACGTCA CCCGCCCCGT   60

TCC                                                                 63

(2) INFORMATION FOR SEQ ID NO:15:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:15:

CGGGATCCGT CGACGCGGCC GCATCATCAA TAATATACC                          39

(2) INFORMATION FOR SEQ ID NO:16:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:16:

CGATGCATCG                                                          10
```

(2) INFORMATION FOR SEQ ID NO:17:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:17:

GGGGTGGCCA GGGTACCTCT AGGCTTTTGC AA                            32

(2) INFORMATION FOR SEQ ID NO:18:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:18:

GGGGGGATCC ATAAACAAGT TCAGAATCC                               29

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:19:

AGCTTGAATT CCCGGGTACC T                                       21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:20:

CTAGAGGTAC CCGGGAATTC A                                       21

(2) INFORMATION FOR SEQ ID NO:21:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:21:

CGGAATTCTT AATTAAGTTA ACATCATCAA TAATATACC                     39

(2) INFORMATION FOR SEQ ID NO:22:

(i) SEQUENCE CHARACTERISTICS:

(A) LENGTH: 66 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:22:

ACGGCGCGCC TTAAGCCACG CCCACACATT TCAGTACGTA CTAGTCTACG TCACCCGCCC    60

CGTTCC    66

(2) INFORMATION FOR SEQ ID NO:23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:23:

CGGAATTCAT CAGGATAGGG CGGTGG    26

(2) INFORMATION FOR SEQ ID NO:24:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:24:

CGGGATCCTA TCGATATTTA AATGTTTTAG GGCGGAGTAA CTTG    44

(2) INFORMATION FOR SEQ ID NO:25:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:25:

TAAGCCACTA GTACGTACTG AAATGTGTGG GCGTGGC    37

(2) INFORMATION FOR SEQ ID NO:26:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:26:

TTAAGCCACG CCCACACATT TCAGTACGTA CTAGTGGCTT AAT    43

(2) INFORMATION FOR SEQ ID NO:27:

(i) SEQUENCE CHARACTERISTICS:
        (A) LENGTH: 21 base pairs
        (B) TYPE: nucleic acid (C) STRANDEDNESS: single
        (D) TOPOLOGY: linear (ii) MOLECULE TYPE: other nucleic acid (xi) SEQUENCE DESCRIPTION: SEQ ID NO:27:

CGTGTAGTGT ATTTATACCC G                                          21

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:28:

TCGTCACTGG GTGGAAAGCC A                                          21

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:29:

TACCCGCCGT CCTAAAATGG C                                          21

(2) INFORMATION FOR SEQ ID NO:30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:30:

GCCTCCATGG AGGTCAGATG T                                          21

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:31:

GCTTGAGCCC GAGACATGTC                                            20

(2) INFORMATION FOR SEQ ID NO:32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:32:

CCCCTCGAGC TCAATCTGTA TCTT                                       24

(2) INFORMATION FOR SEQ ID NO:33:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:33:

GGGGGATCCG AACTTGTTTA TTGCAGC                                    27

(2) INFORMATION FOR SEQ ID NO:34:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:34:

GGGAGATCTA GACATGATAA GATAC                                      25

(2) INFORMATION FOR SEQ ID NO:35:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:35:

GGGAGATCTG TACTGAAATG TGTGGGC                                    27

(2) INFORMATION FOR SEQ ID NO:36:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:36:

GGAGGCTGCA GTCTCCAACG GCGT                                       24

(2) INFORMATION FOR SEQ ID NO:37:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:37:

GGCGAATTCG TCGACATCAT CAATAATATA CC                              32

(2) INFORMATION FOR SEQ ID NO:38:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:38:

CTGTGTACAC CGGCGCA                                      17

(2) INFORMATION FOR SEQ ID NO:39:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:39:

GTACACTGAC CTAGTGCCGC CCGGGCAAAG CCCGGGCGGC ACTAGGTCAG        50

(2) INFORMATION FOR SEQ ID NO:40:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:40:

GTACCTGACC TAGTGCCGCC CGGGCTTTGC CCGGGCGGCA CTAGGTCAGT        50

(2) INFORMATION FOR SEQ ID NO:41:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:41:

GTACATTGAC CTAGTGCCGC CCGGGCAAAG CCCGGGCGGC ACTAGGTCAA TCGAT        55

(2) INFORMATION FOR SEQ ID NO:42:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:42:

GTACATCGAT TGACCTAGTG CCGCCCGGGC TTTGCCCGGG CGGCACTAGG TCAAT        55

(2) INFORMATION FOR SEQ ID NO:43:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:43:

TGGACTTGAG CTGTAAACGC                                              20

(2) INFORMATION FOR SEQ ID NO:44:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:44:

GGGGGATCCT CAAATCGTCA CTTCCGT                                      27

(2) INFORMATION FOR SEQ ID NO:45:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:45:

GGGGTCTAGA CATCATCAAT AATATAC                                      27

(2) INFORMATION FOR SEQ ID NO:46:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:46:

GGCGAATTCG GTACCATCAT CAATAATATA CC                                32

(2) INFORMATION FOR SEQ ID NO:47:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:47:

GTACACTGAC CTAGTGCCGC CCGGGCAAAG CCCGGGCGGC ACTAG                   45
```